(12) United States Patent
Andersen et al.

(10) Patent No.: US 7,601,821 B2
(45) Date of Patent: Oct. 13, 2009

(54) ENCODING AND DECODING REACTIONS FOR DETERMINING TARGET MOLECULES

(75) Inventors: Mark R. Andersen, Carlsbad, CA (US); Kenneth J. Livak, San Jose, CA (US); Adam Broomer, Foster City, CA (US); Caifu Chen, Palo Alto, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 292 days.

(21) Appl. No.: 11/090,830

(22) Filed: Mar. 24, 2005

(65) Prior Publication Data

US 2005/0260640 A1    Nov. 24, 2005

Related U.S. Application Data

(60) Provisional application No. 60/556,157, filed on Mar. 24, 2004, provisional application No. 60/630,681, filed on Nov. 24, 2004, provisional application No. 60/556,224, filed on Mar. 24, 2004, provisional application No. 60/556,162, filed on Mar. 24, 2004, provisional application No. 60/556,163, filed on Mar. 24, 2004.

(51) Int. Cl.
*C07H 21/04* (2006.01)
*C12Q 1/68* (2006.01)

(52) U.S. Cl. ............................. 536/22.1; 435/6

(58) Field of Classification Search ............... 435/6, 435/91.2; 536/24.31, 24.32, 24.33, 22.1
See application file for complete search history.

(56) References Cited

U.S. PATENT DOCUMENTS

| | | | |
|---|---|---|---|
| 4,988,617 A | 1/1991 | Landegren et al. | |
| 5,830,711 A | 11/1998 | Barany et al. | |
| 6,027,889 A | 2/2000 | Barany et al. | |
| 6,270,967 B1 | 8/2001 | Whitcombe et al. | |
| 6,331,393 B1 | 12/2001 | Laird et al. | |
| 6,759,202 B2 | 7/2004 | Grossman et al. | |
| 6,797,470 B2 | 9/2004 | Barany et al. | |
| 7,014,994 B1 * | 3/2006 | Barany et al. ................. | 435/6 |
| 2003/0190646 A1 * | 10/2003 | Wenz et al. ................... | 435/6 |
| 2004/0110134 A1 | 6/2004 | Wenz et al. | |
| 2004/0121371 A1 | 6/2004 | Andersen et al. | |
| 2004/0214196 A1 | 10/2004 | Aydin | |
| 2004/0235005 A1 | 11/2004 | Friedlander et al. | |

FOREIGN PATENT DOCUMENTS

| | | |
|---|---|---|
| EP | 1319718 A1 | 6/2003 |
| WO | WO 96/15271 | 5/1996 |
| WO | WO 9615271 A1 * | 5/1996 |
| WO | WO 03/054511 | 7/2003 |
| WO | WO 2005/026389 A2 | 3/2005 |
| WO | WO 2005/094532 A2 | 10/2005 |

OTHER PUBLICATIONS

International Search Report and Written Opinion issued in International Application No. PCT/US2005/010184 dated Dec. 14, 2005.

* cited by examiner

*Primary Examiner*—Suryaprabha Chunduru
(74) *Attorney, Agent, or Firm*—Lin Sun-Hoffman

(57) ABSTRACT

The present invention is directed to methods, reagents, and kits for detecting the presence or absence of (or quantifying) target polynucleotide sequences and proteins in at least one sample using encoding and decoding reactions. When a particular target polynucleotide is present in a sample for example, a reaction product is formed in the encoding reaction that includes addressable primer portions. At least one labeling probe and at least one address primer can be employed in the decoding amplification reaction thereby providing a detectable signal value depending upon whether a sequence is present or absent. In some embodiments, the encoding comprises a ligation reaction with linker probes, and single nucleotide polymorphisms (SNPs) are analyzed.

7 Claims, 28 Drawing Sheets

Analysis of 2 targets in a single sample. Oligonucleotides are ligated in a single reaction. A portion of this reaction is evaluated in singleplex quantitative PCR.

Analysis of a single target in 2 samples. Oligonucleotides containing sample-encoding sequences are ligated together in a single reaction. The ligation reactions are combined and a portion of this combination is evaluated in a single quantitative PCR.

Second Encoding Ligation Reaction

FIG. 17A

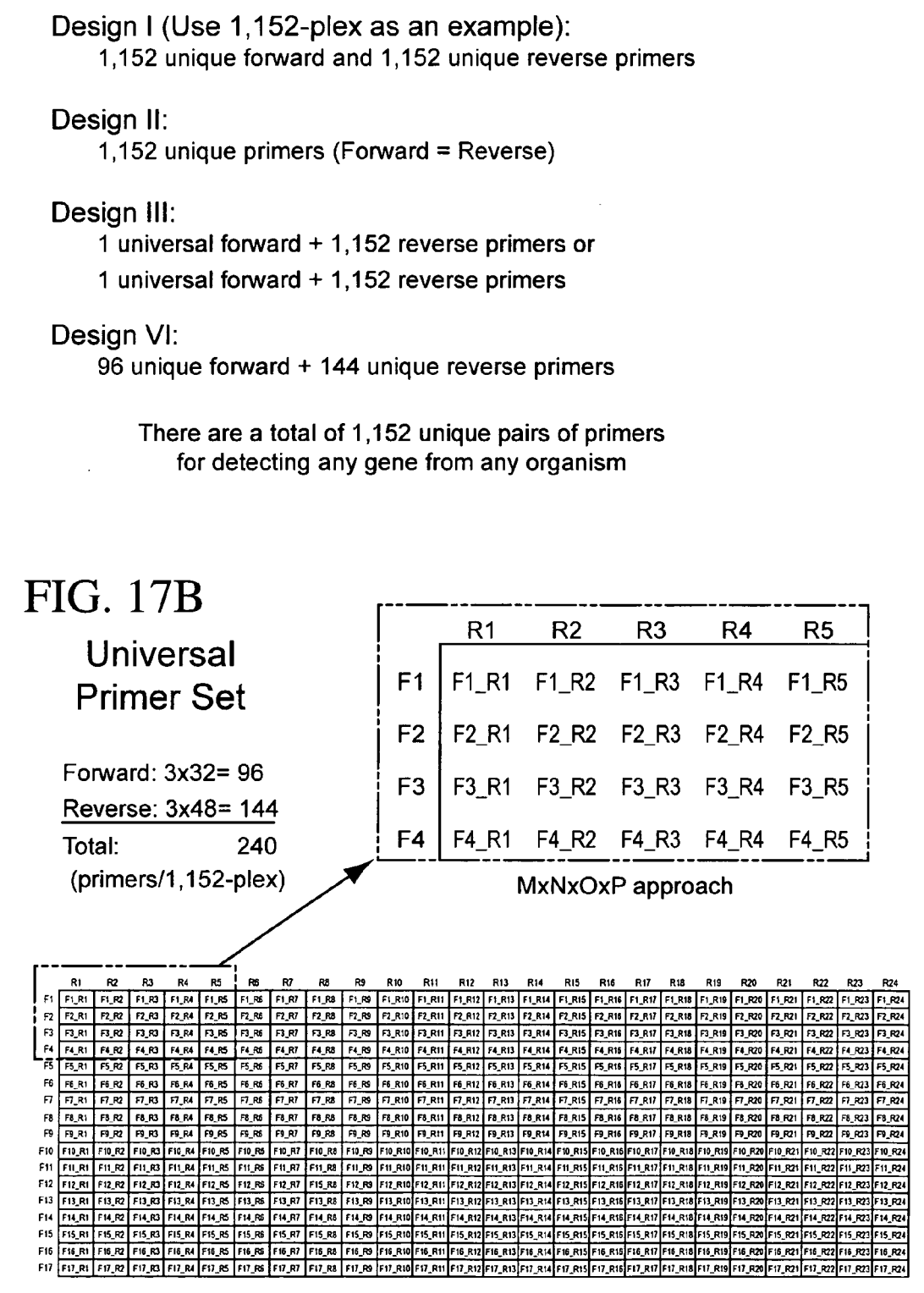

Design I (Use 1,152-plex as an example):
　　1,152 unique forward and 1,152 unique reverse primers Design II:
　　1,152 unique primers (Forward = Reverse)

Design III:
　　1 universal forward + 1,152 reverse primers or
　　1 universal forward + 1,152 reverse primers Design VI:
　　96 unique forward + 144 unique reverse primers There are a total of 1,152 unique pairs of primers
for detecting any gene from any organism

FIG. 17B

Universal Primer Set

Forward: 3x32= 96
Reverse: 3x48= 144
Total:　　　　240
(primers/1,152-plex)

|    | R1    | R2    | R3    | R4    | R5    |
|----|-------|-------|-------|-------|-------|
| F1 | F1_R1 | F1_R2 | F1_R3 | F1_R4 | F1_R5 |
| F2 | F2_R1 | F2_R2 | F2_R3 | F2_R4 | F2_R5 |
| F3 | F3_R1 | F3_R2 | F3_R3 | F3_R4 | F3_R5 |
| F4 | F4_R1 | F4_R2 | F4_R3 | F4_R4 | F4_R5 |

MxNxOxP approach

ENCODING AND DECODING REACTIONS FOR DETERMINING TARGET MOLECULES

CROSS-REFERENCE TO RELATED APPLICATIONS

This application claims priority benefit under 35 U.S.C. § 119(e) from U.S. Provisional Application 60/556,157 to Chen et al., U.S. Provisional Application 60/556,224 to Andersen et al., U.S. Provisional Application 60/556,162 to Livak et al., U.S. Provisional Application 60/556,163 to Lao et al., all filed on Mar. 24, 2004, and U.S. Provisional Application No. 60/630,681 to Chen et al., filed Nov. 24, 2004, all of which are hereby expressly incorporated by reference. This application is co-filed with related U.S. application Encoding and Decoding Reactions for Determining Target Polynucleotides, to Lao et al., all of which is hereby expressly incorporated by reference.

FIELD

The present teachings generally relate to methods, kits, and compositions for detecting target polynucleotide sequences and proteins. More specifically, the teachings relate to encoding reactions and decoding reactions that comprise methods, kits, and compositions for detecting target polynucleotide sequences and proteins.

BACKGROUND

The detection of the presence or absence of (or quantity of) one or more target polynucleotides in a sample or samples containing one or more target sequences is commonly practiced. For example, the detection of cancer and many infectious diseases, such as A.I.D.S. and hepatitis, routinely includes screening biological samples for the presence or absence of diagnostic nucleic acid sequences. Also, detecting the presence or absence of nucleic acid sequences is often used in forensic science, paternity testing, genetic counseling, and organ transplantation.

An organism's genetic makeup is determined by the genes contained within the genome of that organism. Genes are composed of long strands or deoxyribonucleic acid (DNA) polymers that encode the information needed to make proteins. Properties, capabilities, and traits of an organism often are related to the types and amounts of proteins that are, or are not, being produced by that organism.

A protein can be produced from a gene as follows. First, the information that represents the DNA of the gene that encodes a protein, for example, protein "X", is converted into ribonucleic acid (RNA) by a process known as "transcription." During transcription, a single-stranded complementary RNA copy of the gene is made. Next, this RNA copy, referred to as protein X messenger RNA (mRNA), is used by the cell's biochemical machinery to make protein X, a process referred to as "translation." Basically, the cell's protein manufacturing machinery binds to the mRNA, "reads" the RNA code, and "translates" it into the amino acid sequence of protein X. In summary, DNA is transcribed to make mRNA, which is translated to make proteins.

The amount of protein X that is produced by a cell often is largely dependent on the amount of protein X mRNA that is present within the cell. The amount of protein X mRNA within a cell is due, at least in part, to the degree to which gene X is expressed. Whether a particular gene or gene variant is present, and if so, with how many copies, can have significant impact on an organism. Whether a particular gene or gene variant is expressed, and if so, to what level, can have a significant impact on the organism.

SUMMARY

Some embodiments of the present teachings provide a method for detecting at least one target polynucleotide sequence comprising, providing a first reaction vessel comprising a sample, at least one first probe, and at least one second probe, wherein the at least one first probe comprises a target specific portion and a forward addressable primer portion, wherein the at least one second probe comprises a target specific portion and a reverse addressable primer portion, performing an encoding reaction, thereby forming at least one encoding reaction product comprising the forward addressable primer portion, the target specific portions, and the reverse addressable primer portion, whereby the identity of the at least one target polynucleotide sequence is encoded with the first probe and the second probe, providing at least one second reaction vessel comprising at least one forward address primer, at least one reverse address primer, and a label, adding an aliquot of the at least one encoding reaction product to the at least one second reaction vessel, thereby forming at least one first decoding amplification reaction, performing a decoding amplification reaction in the at least one second reaction vessel, wherein the at least one forward address primer hybridizes to the complement of the at least one forward addressable primer portion incorporated into the at least one encoding reaction product during the encoding reaction, wherein the at least one reverse address primer hybridizes to the at least one reverse addressable primer portion incorporated in the at least one encoding reaction product during the encoding reaction, wherein amplification of the at least one encoding reaction product results in signal from the label, detecting the at least one target polynucleotide based on the presence and quantity of signal from the label.

Some embodiments of the present teachings provide a method for detecting at least one target polynucleotide sequence comprising, providing a first reaction vessel comprising a sample, at least one first probe, and at least one second probe, wherein the at least one first probe comprises a target specific portion and a forward addressable primer portion, wherein the at least one second probe comprises a target specific portion and a reverse addressable primer portion, wherein at least one of the probes further comprises an identifying portion, performing an encoding reaction, thereby forming an encoding reaction product mixture comprising at least one encoding reaction product, wherein the at least one encoding reaction product comprises the forward addressable primer portion, the identifying portion, the target specific portions, and the reverse addressable primer portion, whereby the identity of the at least one target polynucleotide sequence is encoded with the first probe and the second probe, providing at least one second reaction vessel comprising at least one forward address primer, at least one reverse address primer, and at least one labeling probe, wherein the at least one labeling probe is complementary to, or complementary to the complement of, the identifying portion of the at least one encoding reaction product, adding an aliquot of the encoding reaction product mixture to the at least one second reaction vessel, thereby forming at least one first decoding amplification reaction, performing a decoding amplification reaction in the at least one second reaction vessel, wherein the at least one forward address primer hybridizes to the complement of the at least one forward addressable primer portion incorporated into the at least one encoding reaction product during the encoding reaction, wherein the at least one reverse address primer hybridizes to the at least one reverse addressable primer portion incorporated in the at least one encoding reaction product during the encoding reaction, wherein amplification of the at least one encoding reaction product results in signal from the at least one labeling probe, detecting the at least one target polynucleotide based on the presence and quantity of signal from the at least one labeling probe.

Some embodiments of the present teachings provide a method for detecting at least one target polynucleotide sequence from at least two samples, comprising, providing at least a first reaction vessel one and a first reaction vessel two, wherein the first reaction vessel one comprises a first sample, at least one first probe, and at least one second probe, wherein the at least one first probe comprises a target specific portion and a forward addressable primer portion, wherein the at least one second probe comprises a target specific portion and a reverse addressable primer portion, wherein at least one of the probes further comprises a first identifying portion, wherein the first reaction vessel two comprises a second sample, at least one first probe, and at least one second probe, wherein the at least one first probe comprises a target specific portion and a forward addressable primer portion, wherein the at least one second probe comprises a target specific portion and a reverse addressable primer portion, wherein at least one of the probes further comprises a second identifying portion, performing a first encoding reaction in the first reaction vessel one, thereby forming a first encoding reaction product mixture comprising at least one first encoding reaction product, wherein the at least one first encoding reaction product comprises the forward addressable primer portion, the identifying portion, the target specific portions, and the reverse addressable primer portion, whereby the identity of the at least one target polynucleotide sequence is encoded with the forward addressable primer portion and the reverse addressable primer portion, and whereby the identity of the sample in the first encoding reaction is encoded by the first identifying portion, performing a second encoding reaction in first reaction vessel two, thereby forming a second encoding reaction product mixture comprising at least one second encoding reaction product, wherein the at least one second encoding reaction product comprises the forward addressable primer portion, the identifying portion, the target specific portions, and the reverse addressable primer portion, whereby the identity of the at least one target polynucleotide sequence is encoded with the forward addressable primer portion and the reverse addressable primer portion, and whereby the identity of the sample in the second encoding reaction is encoded by the second identifying portion, combining the first encoding reaction product mixture from the first reaction vessel one with the second encoding reaction product mixture from the first reaction vessel two, thereby forming an encoding reaction product mixture, providing at least a second reaction vessel one and a second reaction vessel two, wherein the second reaction vessel one comprises at least one forward address primer, at least one reverse address primer, and at least a first labeling probe one and at least a second labeling probe one, wherein the first labeling probe one is complementary to, or complementary to the complement of, the first identifying portion of the at least one encoding reaction product from the first reaction vessel one, and wherein the second labeling probe one is complementary to, or complementary to the complement of, the second identifying portion of the at least one encoding reaction product from the first reaction vessel two, wherein second reaction vessel two comprises at least one forward address primer, at least one reverse address primer, and at least a first labeling probe one and at least a second labeling probe one, wherein the first labeling probe one is complementary to, or complementary to the complement of, the first identifying portion of the at least one encoding reaction product from the first reaction vessel one, and wherein the second labeling probe one is complementary to, or complementary to the complement of, the second identifying portion of the at least one encoding reaction product from the first reaction vessel two, adding an aliquot of the encoding reaction product mixture to the at least one second reaction vessel one, thereby forming a first decoding amplification reaction in the second reaction vessel one, performing a first decoding amplification reaction in the second reaction vessel one, wherein the first decoding amplification reaction comprises at least one distinct forward address primer that can hybridize to the complement of the at least one forward addressable primer portion introduced into the at least one encoding reaction product during the first encoding reaction and the second encoding reaction, wherein the at least one reverse address primer hybridizes to the at least one reverse addressable primer portion introduced in the at least one encoding reaction product during the first encoding reaction and the second encoding reaction, wherein amplification of the at least one encoding reaction product results in signal from the first labeling probe one when the encoding reaction product is derived from the first encoding reaction, wherein amplification of the at least one encoding reaction product results in signal from the second labeling probe one when the encoding reaction product is derived from the second encoding reaction, detecting and quantifying the at least one target polynucleotide in the at least two samples based on the presence and quantity of signal from the first labeling probe one and the second labeling probe one in the first decoding reaction, adding an aliquot of the encoding reaction product mixture to the at least one second reaction vessel two, thereby forming a second decoding amplification reaction in the second reaction vessel two, performing a second decoding amplification reaction in the second reaction vessel two, wherein the second decoding amplification reaction comprises at least one distinct forward address primer that can hybridize to the complement of the at least one forward addressable primer portion introduced into the at least one encoding reaction product during the first encoding reaction and the second encoding reaction, wherein the at least one reverse address primer hybridizes to the at least one reverse addressable primer portion introduced in the at least one encoding reaction product during the first encoding reaction and the second encoding reaction, wherein amplification of the at least one encoding reaction product results in signal from the first labeling probe one when the encoding reaction product is derived from the first encoding reaction, wherein amplification of the at least one encoding reaction product results in signal from the second labeling probe one when the encoding reaction product is derived from the second encoding reaction, detecting and quantifying the at least one target polynucleotide in the at least two samples based on the presence and quantity of signal from the first labeling probe one and the second labeling probe one in the first decoding reaction.

Some embodiments of the present teachings provide a method for detecting at least one target polynucleotide sequence from at least two samples, comprising, providing at least a first reaction vessel one and a first reaction vessel two, wherein the first reaction vessel one comprises a first sample, at least one first probe, and at least one second probe, wherein the at least one first probe comprises a target specific portion and a forward addressable primer portion, wherein the at least one second probe comprises a target specific portion and a reverse addressable primer portion, wherein at least one of the probes further comprises a first identifying portion, wherein the first reaction vessel two comprises a second sample, at least one first probe, and at least one second probe, wherein the at least one first probe comprises a target specific portion and a forward addressable primer portion, wherein the at least one second probe comprises a target specific portion and a reverse addressable primer portion, wherein at least one of the probes further comprises a second identifying portion, performing a first encoding ligation reaction in the first reaction vessel one, thereby forming a first encoding ligation reaction product mixture comprising at least one first encoding ligation reaction product, wherein the at least one first encoding ligation reaction product comprises the forward addressable primer portion, the identifying portion, the target specific portions, and the reverse addressable primer portion, whereby the identity of the at least one target polynucleotide sequence is encoded with the forward addressable primer portion and the reverse addressable primer portion, and whereby the identity of the sample in the first encoding ligation reaction is encoded by the first identifying portion, performing a second encoding ligation reaction in first reaction vessel two, thereby forming a second encoding ligation reaction product mixture comprising at least one second encoding ligation reaction product, wherein the at least one second encoding ligation reaction product comprises the forward addressable primer portion, the identifying portion, the target specific portions, and the reverse addressable primer portion, whereby the identity of the at least one target polynucleotide sequence is encoded with the forward addressable primer portion and the reverse addressable primer portion, and whereby the identity of the sample in the second encoding ligation reaction is encoded by the second identifying portion, combining the first encoding ligation reaction product mixture from the first reaction vessel one with the second encoding ligation reaction product mixture from the first reaction vessel two, thereby forming an encoding ligation reaction product mixture, providing at least a second reaction vessel one and a second reaction vessel two, wherein the second reaction vessel one comprises at least one forward address primer, at least one reverse address primer, and at least a first labeling probe one and at least a second labeling probe one, wherein the first labeling probe one is complementary to, or complementary to the complement of, the first identifying portion of the at least one encoding ligation reaction product from the first reaction vessel one, and wherein the second labeling probe one is complementary to, or complementary to the complement of, the second identifying portion of the at least one encoding ligation reaction product from the first reaction vessel two, wherein second reaction vessel two comprises at least one forward address primer, at least one reverse address primer, and at least a first labeling probe one and at least a second labeling probe one, wherein the first labeling probe one is complementary to, or complementary to the complement of, the first identifying portion of the at least one encoding ligation reaction product from the first reaction vessel one, and wherein the second labeling probe one is complementary to, or complementary to the complement of, the second identifying portion of the at least one encoding ligation reaction product from the first reaction vessel two, adding an aliquot of the encoding ligation reaction product mixture to the at least one second reaction vessel one, thereby forming a first decoding amplification reaction in the second reaction vessel one, performing a first decoding amplification reaction in the second reaction vessel one, wherein the first decoding amplification reaction comprises at least one distinct forward address primer that can hybridize to the complement of the at least one forward addressable primer portion introduced into the at least one encoding ligation reaction product during the first encoding ligation reaction and the second encoding ligation reaction, wherein the at least one reverse address primer hybridizes to the at least one reverse addressable primer portion introduced in the at least one encoding ligation reaction product during the first encoding ligation reaction and the second encoding ligation reaction, wherein amplification of the at least one encoding ligation reaction product results in signal from the first labeling probe one when the encoding ligation reaction product is derived from the first encoding ligation reaction, wherein amplification of the at least one encoding ligation reaction product results in signal from the second labeling probe one when the encoding ligation reaction product is derived from the second encoding reaction, detecting and quantifying the at least one target polynucleotide in the at least two samples based on the presence and quantity of signal from the first labeling probe one and the second labeling probe one in the first decoding reaction, adding an aliquot of the encoding ligation reaction product mixture to the at least one second reaction vessel two, thereby forming a second decoding amplification reaction in the second reaction vessel two, performing a second decoding amplification reaction in the second reaction vessel two, wherein the second decoding amplification reaction comprises at least one distinct forward address primer that can hybridize to the complement of the at least one forward addressable primer portion introduced into the at least one encoding ligation reaction product during the first encoding ligation reaction and the second encoding ligation reaction, wherein the at least one reverse address primer hybridizes to the at least one reverse addressable primer portion introduced in the at least one encoding ligation reaction product during the first encoding ligation reaction and the second encoding ligation reaction, wherein amplification of the at least one encoding ligation reaction product results in signal from the first labeling probe one when the encoding ligation reaction product is derived from the first encoding ligation reaction, wherein amplification of the at least one encoding ligation reaction product results in signal from the second labeling probe one when the encoding ligation reaction product is derived from the second encoding reaction, detecting and quantifying the at least one target polynucleotide in the at least two samples based on the presence and quantity of signal from the first labeling probe one and the second labeling probe one in the first decoding reaction.

In some embodiments, the present teachings provide a kit for detecting at least one target polynucleotide sequence comprising a probe set, a solid support with dried down primers and optionally at least one labeling probe, and a master mix.

In some embodiments, the present teachings provide a method for detecting at least one target polynucleotide in at least one sample, comprising:
at least one step for interrogating the at least one target polynucleotide;
at least one step for generating at least one ligation product; and
at least one step for detecting the at least one target polynucleotide.

In some embodiments, the present teachings provide a method for detecting at least one target polynucleotide in at least one sample, comprising:
at least one step for interrogating the at least one target polynucleotide;
at least one step for generating at least one ligation product;
at least one step for generating the at least one amplified ligation product; and
at least one step for detecting the at least one target polynucleotide.

In some embodiments, the present teachings provide a method for detecting at least one target polynucleotide in at least one sample, comprising:
at least one step for interrogating the at least one target polynucleotide;
at least one step for generating at least one ligation product;
at least one step for removing unincorporated reaction components; and
at least one step for detecting the at least one target nucleotide.

In some embodiments, the present teachings provide a kit for detecting at least one target polynucleotide comprising: at least one means for ligating, at least one means for amplifying, at least one means for removing, or combinations thereof.

The present teachings further contemplate procedures for detecting and quantifying proteins.

BRIEF DESCRIPTION OF THE DRAWINGS

The skilled artisan will understand that the drawings, described below, are for illustration purposes only. The drawings are not intended to limit the scope of the present teachings in any way.

FIG. 17 depicts certain primer configurations in accordance with some embodiments of the present teachings.

DESCRIPTION OF EXEMPLARY EMBODIMENTS

Figure 1:
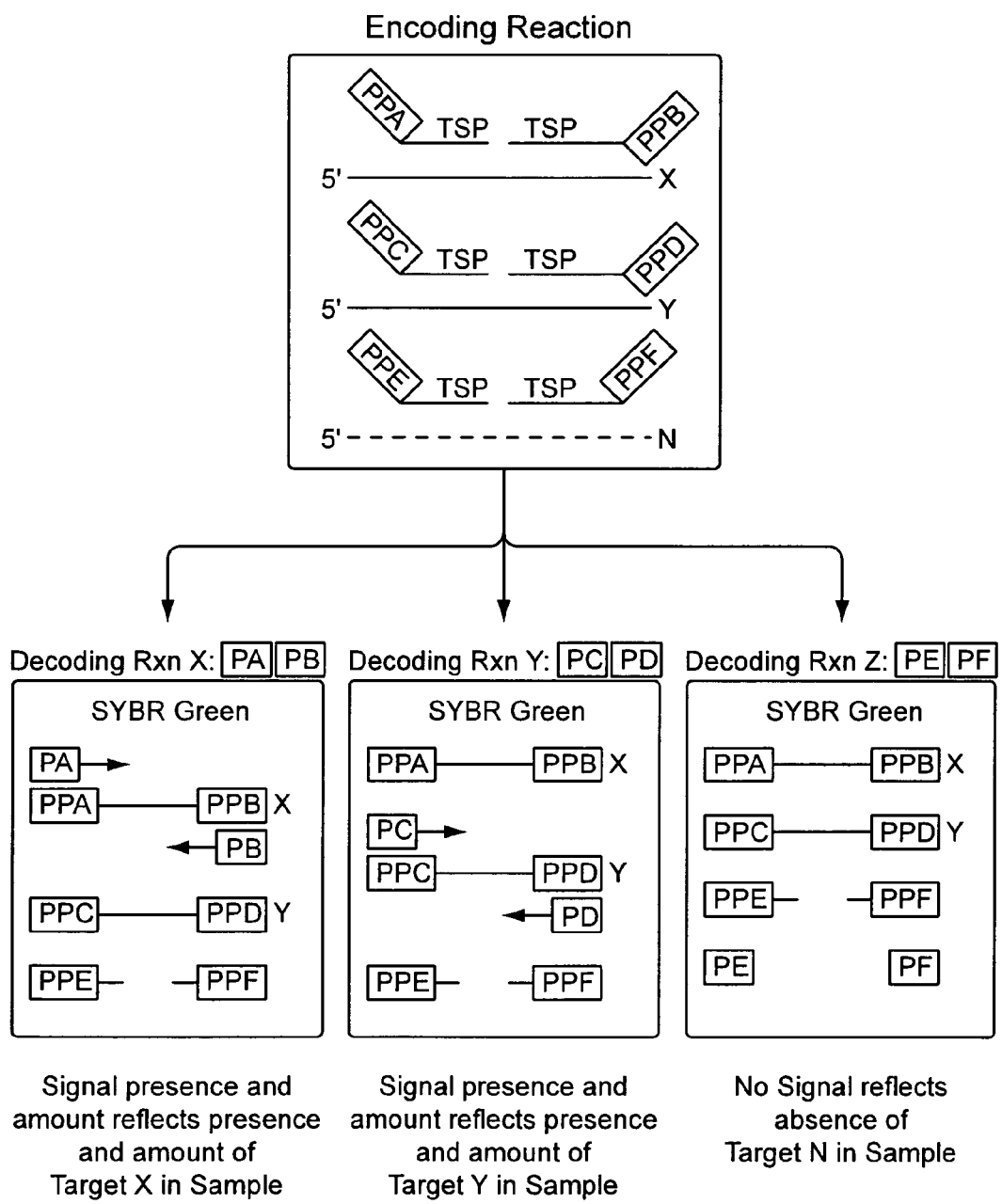
FIG. 1 depicts certain compositions and reaction interactions in accordance with some embodiments of the present teachings.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose.

It is to be understood that both the foregoing general description and the following detailed description are exemplary and explanatory only and are not restrictive of the present teachings. In this application, the use of the singular includes the plural unless specifically stated otherwise. For example, "a probe" means that more than one probe may be present. Also, the use of "or" means "and/or" unless stated otherwise. Similarly, "comprise", "comprises", "comprising", "include", "includes", and "including" are not intended to be limiting.

1. Definitions

As used herein, the "probes," "primers," "targets," "oligonucleotides," "polynucleotides," "nucleobase sequences," and "oligomers" of the present teachings can be comprised of at least one of ribonucleotides, deoxynucleotides, modified ribonucleotides, modified deoxyribonucleotides, modified phosphate-sugar-backbone oligonucleotides, nucleotide analogs, and combinations thereof, and can be single stranded, double stranded, or contain portions of both double stranded and single stranded sequence, as appropriate. Some more elaborative and non-limiting definitions are provided infra.

The term "nucleotide", as used herein, generically encompasses the following terms, which are defined below: nucleotide base, nucleoside, nucleotide analog, and universal nucleotide.

The term "nucleotide base", as used herein, refers to a substituted or unsubstituted parent aromatic ring or rings. In some embodiments, the aromatic ring or rings contain at least one nitrogen atom. In some embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-Δ2-isopentenyladenine (6iA), N6-Δ2-isopentenyl-2-methylthioadenine (2ms6iA), N6-methyladenine, guanine (G), isoguanine, N2-dimethylguanine (dmG), 7-methylguanine (7mG), 2-thiopyrimidine, 6-thioguanine (6sG) hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, O4-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. In some embodiments, nucleotide bases are universal nucleotide bases. Additional exemplary nucleotide bases can be found, e.g., in Fasman, 1989, Practical Handbook of Biochemistry and Molecular Biology, pp. 385-394, CRC Press, Boca Raton, Fla., and the references cited therein. Further examples of universal bases can be found for example in Loakes, N. A. R. 2001, vol 29:2437-2447 and Seela N. A. R. 2000, vol 28:3224-3232.

The term "nucleoside", as used herein, refers to a compound having a nucleotide base covalently linked to the C-1' carbon of a pentose sugar. In some embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-C14)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14) aryloxyribose. Also see e.g. 2'-O-methyl, 4'-α-anomeric nucleotides, 1'-α-anomeric nucleotides (Asseline (1991) Nucl. Acids Res. 19:4067-74), 2'-4'- and 3'-4'-linked and other "locked" or "LNA", bicyclic sugar modifications (WO 98/22489; WO 98/39352; WO 99/14226). "LNA" or "locked nucleic acid" is a DNA analogue that is conformationally locked such that the ribose ring is constrained by a methylene linkage between the 2'-oxygen and the 3'- or 4'-carbon. The conformation restriction imposed by the linkage often increases binding affinity for complementary sequences and increases the thermal stability of such duplexes.

Exemplary LNA sugar analogs within a polynucleotide include the structures:

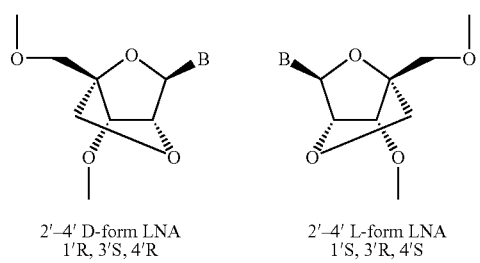

2'-4' D-form LNA
1'R, 3'S, 4'R

2'-4' L-form LNA
1'S, 3'R, 4'S

-continued

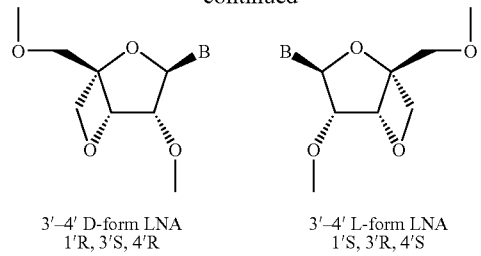

3'-4' D-form LNA
1'R, 3'S, 4'R

3'-4' L-form LNA
1'S, 3'R, 4'S where B is any nucleobase.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) DNA Replication, $2^{nd}$ Ed., Freeman, San Francisco, Calif.).

One or more of the pentose carbons of a nucleoside may be substituted with a phosphate ester having the formula:

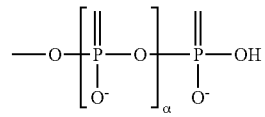

where α is an integer from 0 to 4. In some embodiments, α is 2 and the phosphate ester is attached to the 3'- or 5'-carbon of the pentose. In some embodiments, the nucleosides are those in which the nucleotide base is a purine, a 7-deazapurine, a pyrimidine, a universal nucleotide base, a specific nucleotide base, or an analog thereof.

The term "nucleotide analog", as used herein, refers to embodiments in which the pentose sugar and/or the nucleotide base and/or one or more of the phosphate esters of a nucleoside may be replaced with its respective analog. In some embodiments, exemplary pentose sugar analogs are those described above. In some embodiments, the nucleotide analogs have a nucleotide base analog as described above. In some embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions. Other nucleic acid analogs and bases include for example intercalating nucleic acids (INAs, as described in Christensen and Pedersen, 2002), and AEGIS bases (Eragen, U.S. Pat. No. 5,432,272). Additional descriptions of various nucleic acid analogs can also be found for example in (Beaucage et al., Tetrahedron 49(10):1925 (1993) and references therein; Letsinger, J. Org.

Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048. Other nucleic analogs comprise phosphorodithioates (Briu et al., J. Am. Chem. Soc. 111:2321 (1989), 0-methylphophoroamidite linkages (see Eckstein, Oligonucleotides and Analogues: A Practical Approach, Oxford University Press), those with positive backbones (Denpcy et al., Proc. Natl. Acad. Sci. USA 92:6097 (1995); non-ionic backbones (U.S. Pat. Nos. 5,386,023, 5,386,023, 5,637,684, 5,602,240, 5,216,141, and 4,469,863. Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (194): Chaq.ters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169-176). Several nucleic acid analogs are also described in Rawls, C & E News June 2, 1997 page 35.

The term "universal nucleotide base" or "universal base", as used herein, refers to an aromatic ring moiety, which may or may not contain nitrogen atoms. In some embodiments, a universal base may be covalently attached to the C-1' carbon of a pentose sugar to make a universal nucleotide. In some embodiments, a universal nucleotide base does not hydrogen bond specifically with another nucleotide base. In some embodiments, a universal nucleotide base hydrogen bonds with nucleotide base, up to and including all nucleotide bases in a particular target polynucleotide. In some embodiments, a nucleotide base may interact with adjacent nucleotide bases on the same nucleic acid strand by hydrophobic stacking. Universal nucleotides include, but are not limited to, deoxy-7-azaindole triphosphate (d7AITP), deoxyisocarbostyril triphosphate (dICSTP), deoxypropynylisocarbostyril triphosphate (dPICSTP), deoxymethyl-7-azaindole triphosphate (dM7AITP), deoxyImPy triphosphate (dImPyTP), deoxyPP triphosphate (dPPTP), or deoxypropynyl-7-azaindole triphosphate (dP7AITP). Further examples of such universal bases can be found, inter alia, in Published U.S. application Ser. No. 10/290672, and U.S. Pat. No. 6,433,134.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g. 3'-5' and 2'-5', inverted linkages, e.g. 3'-3' and 5'-5', branched structures, or internucleotide analogs. Polynucleotides have associated counter ions, such as $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of internucleotide, nucleobase and/or sugar analogs. Polynucleotides typically range in size from a few monomeric units, e.g. 3-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, and "T" denotes thymidine, unless otherwise noted.

As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methlylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

As used herein, "nucleobase sequence" means any segment, or aggregate of two or more segments (e.g. the aggregate nucleobase sequence of two or more oligomer blocks), of a polymer that comprises nucleobase-containing subunits. Non-limiting examples of suitable polymers or polymers segments include oligodeoxynucleotides (e.g. DNA), oligoribonucleotides (e.g. RNA), peptide nucleic acids (PNA), PNA chimeras, PNA combination oligomers, nucleic acid analogs and/or nucleic acid mimics.

As used herein, "polynucleobase strand" means a complete single polymer strand comprising nucleobase subunits. For example, a single nucleic acid strand of a double stranded nucleic acid is a polynucleobase strand.

As used herein, "nucleic acid" is a nucleobase sequence-containing polymer, or polymer segment, having a backbone formed from nucleotides, or analogs thereof. Preferred nucleic acids are DNA and RNA.

As used herein, "peptide nucleic acid" or "PNA" means any oligomer or polymer segment (e.g. block oligomer) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference. The term "peptide nucleic acid" or "PNA" shall also apply to any oligomer or polymer segment comprising two or more subunits of those nucleic acid mimics described in the following publications: Lagriffoul et al., Bioorganic & Medicinal Chemistry Letters, 4: 1081-1082 (1994); Petersen et al., Bioorganic & Medicinal Chemistry Letters, 6: 793-796 (1996); Diderichsen et al., Tett. Lett. 37: 475-478 (1996); Fujii et al., Bioorg. Med. Chem. Lett. 7: 637-627 (1997); Jordan et al., Bioorg. Med. Chem. Lett. 7: 687-690 (1997); Krotz et al., Tett. Lett. 36: 6941-6944 (1995); Lagriffoul et al., Bioorg. Med. Chem. Lett. 4: 1081-1082 (1994); Diederichsen, U., Bioorganic & Medicinal Chemistry Letters, 7: 1743-1746 (1997); Lowe et al., J. Chem. Soc. Perkin Trans. 1, (1997) 1: 539-546; Lowe et J. Chem. Soc. Perkin Trans. 11: 547-554 (1997); Lowe et al., J. Chem. Soc. Perkin Trans. 11:555-560 (1997); Howarth et al., J. Org. Chem. 62: 5441-5450 (1997); Altmann, K-H et al., Bioorganic & Medicinal Chemistry Letters, 7: 1119-1122 (1997); Diederichsen, U., Bioorganic & Med. Chem. Lett., 8: 165-168 (1998); Diederichsen et al., Angew. Chem. Int. Ed., 37: 302-

305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMS) of Shah et al. as disclosed in WO96/04000.

In some embodiments, a "peptide nucleic acid" or "PNA" is an oligomer or polymer segment comprising two or more covalently linked subunits of the formula found in paragraph 76 of U.S. patent application Ser. No. 2003/0077608A1 wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; $-(CJ_2)_s-$ and a group of the formula; $-(CJ_2)_sC(O)-$, wherein, J is defined above and each s is a whole number from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), other naturally occurring nucleobase analogs or other non-naturally occurring nucleobases.

In some other embodiments, a PNA subunit consists of a naturally occurring or non-naturally occurring nucleobase attached to the N-α-glycine nitrogen of the N-[2-(aminoethyl)]glycine backbone through a methylene carbonyl linkage; this currently being the most commonly used form of a peptide nucleic acid subunit.

As used herein, "target polynucleotide sequence" is a nucleobase sequence of a polynucleobase strand sought to be determined. It is to be understood that the nature of the target sequence is not a limitation of the present teachings. The polynucleobase strand comprising the target sequence may be provided from any source. For example, the target sequence may exist as part of a nucleic acid (e.g. DNA or RNA), PNA, nucleic acid analog or other nucleic acid mimic. The target can be methylated, non-methylated, or both. The sample containing the target sequence may be from any source, and is not a limitation of the present teachings. Further, it will be appreciated that "target" can refer to both a "target polynucleotide sequence" as well as surrogates thereof, for example ligation products, amplification products, and sequences encoded therein.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide (for example an OLA product, a PCR product, etc), the orientation of the two primer portions is generally different. For example, one PCR primer can directly hybridize to the first primer portion, while the other PCR primer can hybridize to the complement of the second primer portion. Stated another way, the first primer portion can be in a sense orientation, and the second primer portion can be in an antisense orientation. In addition, "universal" primers and primer portions as used herein are generally chosen to be as unique as possible given the particular assays and host genomes to ensure specificity of the assay. However, as will be appreciated by those of skill in the art, different configurations of primer portions can be used, for example one reaction can utilize 500 upstream probes with a first primer portion or battery of primer portions, and an additional 500 downstream probes with a second primer portion or battery of primer portions. Further, all of the universal primer portions can be the same for all targets in a reaction thereby allowing, for example, a single upstream primer and a single downstream primer to amplify all targets, and/or, a single primer to serve as both upstream and downstream primer to amplify all targets. Alternatively, "batteries" of universal upstream primer portions and batteries of universal downstream primer portions can used, either simultaneously or sequentially. In some embodiments, at least one of the primer portions can comprise a T7 RNA polymerase site.

As used herein, "forward" and "reverse" are used to indicate relative orientation of probes on a target, and generally refer to a 5' to 3' "forward" oriented primer hybridized to the 3' end of the 'top' strand of a target polynucleotide, and a 5' to 3' "reverse" oriented primer hybridized to the 3' end of the bottom strand of a polynucleotide target. As will be recognized by those of skill in the art, these terms are not-intended to be limiting, but rather provide illustrative orientation in any given embodiment.

As used herein, the term "sample" refers to a mixture from which the at least one target polynucleotide sequence is derived, such sources including, but not limited to, raw viruses, prokaryotes, protists, eukaryotes, plants, fungi, and animals. These sample sources may include, but are not limited to, whole blood, a tissue biopsy, lymph, bone marrow, amniotic fluid, hair, skin, semen, biowarfare agents, anal secretions, vaginal secretions, perspiration, various environmental samples (for example, agricultural, water, and soil), research samples generally, purified samples generally, and cultured cells. It will be appreciated that nucleic acids can be isolated from samples using any of a variety of procedures known in the art, for example the Applied Biosystems ABI Prism 6100 Nucleic Acid PrepStation, and the ABI Prism TM 6700 Automated Nucleic Acid Workstation, Boom et al., U.S. Pat. No. 5,234,809, etc. It will be appreciated that nucleic acids can be cut or sheared prior to analysis, including the use of such procedures as mechanical force, sonication, restriction endonuclease cleavage, or any method known in the art.

It will be appreciated that the selection of the probes to query a given target polynucleotide sequence, and the selection of which target polynucleotide sequences to pool in a given reaction, will involve procedures generally known in the art, and can involve the use of algorithms to select for those sequences with minimal secondary and tertiary structure, those targets with minimal sequence redundancy with other regions of the genome, those target regions with desirable thermodynamic characteristics, and other parameters desirable for the context at hand. In some embodiments, probes can further comprise various modifications such as a minor groove binder (see for example U.S. Pat. No. 6,486,308) to further provide desirable thermodynamic characteristics.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "target specific portion" refers to the portion of an oligonucleotide complementary to a target polynucleotide.

The term "corresponding" as used herein refers to at least one specific relationship between the elements to which the term refers. For example, at least one first probe of a particular upstream probe set corresponds to at least one downstream probe of the same probe set, and vice versa. At least one primer is designed to anneal with the primer portion of at least one corresponding probe, at least one corresponding ligation product, at least one corresponding amplified ligation product, or combinations thereof. The target-specific portions of the probes of a particular probe set can be designed to hybridize with a complementary or substantially complementary region of the corresponding target nucleic acid sequence. A particular affinity moiety can bind to the corresponding affinity moiety binder, for example but not limited to, the affinity moiety binder streptavidin binding to the affinity moiety biotin. A particular mobility probe can hybridize with the corresponding identifier portion complement; and so forth.

As used herein the terms "annealing" and "hybridization" are used interchangeably and mean the complementary base-pairing interaction of one nucleic acid with another nucleic acid that results in formation of a duplex, triplex, or other higher-ordered structure. In some embodiments, the primary interaction is base specific, e.g., A/T and G/C, by Watson/Crick and Hoogsteen-type hydrogen bonding. In some embodiments, base-stacking and hydrophobic interactions may also contribute to duplex stability. Conditions for hybridizing nucleic acid probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the probes and the complementary target sequences, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. Further, in general probes and primers of the present teachings are designed to be complementary to a target sequence, such that hybridization of the target and the probes or primers occurs. It will be appreciated, however, that this complementarity need not be perfect; there can be any number of base pair mismatches that will interfere with hybridization between the target sequence and the single stranded nucleic acids of the present teachings. However, if the number of base pair mismatches is so great that no hybridization can occur under even the least stringent of hybridization conditions, the sequence is not a complementary target sequence. Thus, by "substantially complementary" herein is meant that the probes or primers are sufficiently complementary to the target sequence to hybridize under the selected reaction conditions.

As used herein, the terms "label" refers to detectable moieties that can be attached to an oligonucleotide, labeling probe, mobility probe, or otherwise be used in a reporter system, to thereby render the molecule detectable by an instrument or method. For example, a label can be any moiety that: (i) provides a detectable signal; (ii) interacts with a second label to modify the detectable signal provided by the first or second label; or (iii) confers a capture function, e.g. hydrophobic affinity, antibody/antigen, ionic complexation. The skilled artisan will appreciate that many different species of reporter labels can be used in the present teachings, either individually or in combination with one or more different labels. Exemplary labels include, but are not limited to, fluorophores, radioisotopes, QUANTUM DOTS, chromogens, SYBR GREEN™, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.SPh.NCS," "Cy.7.OphEt.NCS," "Cy7.OphEt.CO$_2$Su", and IRD800 (see, e.g., J. Flanagan et al., Bioconjug. Chem. 8:751-56 (1997); and DNA Synthesis with IRD800 Phosphoramidite, LI-COR Bulletin #111, LI-COR, Inc., Lincoln, Nebr.), electrochemiluminescence labels, including but not limited to, tris(bipyridal) ruthenium (II), also known as Ru(bpy)$_3^{2+}$, Os(1,10-phenanthroline)$_2$bis (diphenylphosphino)ethane$^{2+}$, also known as Os(phen)$_2$(dppene)$^{2+}$, luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as Ru(v-bpy$_3^{2+}$), and the like. Detailed descriptions of ECL and electrochemiluminescent moieties can be found in, among other places, A. Bard and L. Faulkner, Electrochemical Methods, John Wiley & Sons (2001); M. Collinson and M. Wightman, Anal. Chem. 65:2576 et seq. (1993); D. Brunce and M. Richter, Anal. Chem. 74:3157 et seq. (2002); A. Knight, Trends in Anal. Chem. 18:47 et seq. (1999); B. Muegge et al., Anal. Chem. 75:1102 et seq. (2003); H. Abrunda et al., J. Amer. Chem. Soc. 104:2641 et seq. (1982); K. Maness et al., J. Amer. Chem. Soc. 118:10609 et seq. (1996); M. Collinson and R. Wightman, Science 268:1883 et seq. (1995); and U.S. Pat. No. 6,479,233.

As used herein, the term "fluorophore" refers to a label that comprises a resonance-delocalized system or aromatic ring system that absorbs light at a first wavelength and emits fluorescent light at a second wavelength in response to the absorption event. A wide variety of such dye molecules are known in the art. For example, fluorescent dyes can be selected from any of a variety of classes of fluorescent compounds, such as xanthenes, rhodamines, fluoresceins, cyanines, phthalocyanines, squaraines, and bodipy dyes. In some embodiments, the dye comprises a xanthene-type dye, which contains a fused three-ring system of the form:

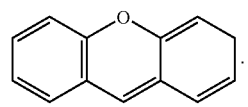

This parent xanthene ring may be unsubstituted (i.e., all substituents are H) or can be substituted with one or more of a variety of the same or different substituents, such as described below. In some embodiments, the dye contains a parent xanthene ring having the general structure:

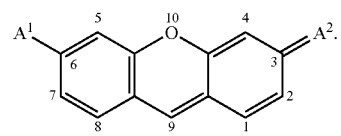

In the parent xanthene ring depicted above, $A^1$ is OH or $NH_2$ and $A^2$ is O or $NH_2^+$. When $A^1$ is OH and $A^2$ is O, the parent xanthene ring is a fluorescein-type xanthene ring. When $A^1$ is $NH^2$ and $A^2$ is $NH_2^+$, the parent xanthene ring is a rhodamine-type xanthene ring. When $A^1$ is $NH_2$ and $A^2$ is O, the parent xanthene ring is a rhodol-type xanthene ring. In the parent xanthene ring depicted above, one or both nitrogens of $A^1$ and $A^2$ (when present) and/or one or more of the carbon atoms at positions C1, C2, C4, C5, C7, C8 and C9 can be independently substituted with a wide variety of the same or different substituents. In some embodiments, typical substituents can include, but are not limited to, —X, —R, —OR, —SR, —NRR, perhalo ($C_1$-$C_6$) alkyl, —$CX_3$, —$CF_3$, —CN, —OCN, —SCN, —NCO, —NCS, —NO, —$NO_2$, —$N_3$, —$S(O)_2O$—, —$S(O)_2OH$, —$S(O)_2R$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F or Cl) and each R is independently hydrogen, ($C_1$-$C_6$) alkyl, ($C_1$-$C_6$) alkanyl, ($C_1$-$C_6$) alkenyl, ($C_1$-$C_6$) alkynyl, ($C_5$-$C_{20}$) aryl, ($C_6$-$C_{26}$) arylalkyl, ($C_5$-$C_{20}$) arylaryl, heteroaryl, 6-26 membered heteroarylalkyl 5-20 membered heteroaryl-heteroaryl, carboxyl, acetyl, sulfonyl, sulfinyl, sulfone, phosphate, or phosphonate. Moreover, the C1 and C2 substituents and/or the C7 and C8 substituents can be taken together to form substituted or unsubstituted buta[1,3]dieno or ($C_5$-$C_{20}$) aryleno bridges. Generally, substituents that do not tend to quench the fluorescence of the parent xanthene ring are preferred, but in some embodiments quenching substituents may be desirable. Substituents that tend to quench fluorescence of parent xanthene rings are electron-withdrawing groups, such as —$NO_2$, —Br, and —I. In some embodiments, C9 is unsubstituted. In some embodiments, C9 is substituted with a phenyl group. In some embodiments, C9 is substituted with a substituent other than phenyl. When $A^1$ is $NH_2$ and/or $A^2$ is $NH_2^+$, these nitrogens can be included in one or more bridges involving the same nitrogen atom or adjacent carbon atoms, e.g., ($C_1$-$C_{12}$) alkyldiyl, ($C_1$-$C_{12}$) alkyleno, 2-12 membered heteroalkyldiyl and/or 2-12 membered heteroalkyleno bridges. Any of the substituents on carbons C1, C2, C4, C5, C7, C8, C9 and/or nitrogen atoms at C3 and/or C6 (when present) can be further substituted with one or more of the same or different substituents, which are typically selected from —X, —R', =O, —OR', —SR', =S, —NR'R', =NR', —$CX_3$, —CN, —OCN, —SCN, —NCO, —NCS, —NO, —$NO_2$, =$N_2$, —$N_3$, —NHOH, —$S(O)_2O^-$, —$S(O)_2OH$, —$S(O)_2R'$, —$P(O)(O^-)_2$, —$P(O)(OH)_2$, —C(O)R', —C(O)X, —C(S)R', —C(S)X, —C(O)OR', —C(O)O$^-$, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, ($C_1$-$C_6$) alkyl, 2-6 membered heteroalkyl, ($C_5$-$C_{14}$) aryl or heteroaryl, carboxyl, acetyl, sulfonyl, sulfinyl, sulfone, phosphate, or phosphonate.

Exemplary parent xanthene rings include, but are not limited to, rhodamine-type parent xanthene rings and fluorescein-type parent xanthene rings.

In one embodiment, the dye contains a rhodamine-type xanthene dye that includes the following ring system:

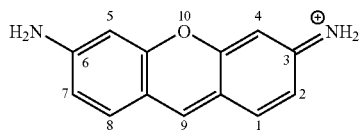

In the rhodamine-type xanthene ring depicted above, one or both nitrogens and/or one or more of the carbons at positions C1, C2, C4, C5, C7 or C8 can be independently substituted with a wide variety of the same or different substituents, as described above for the parent xanthene rings, for example. C9 may be substituted with hydrogen or other substituent, such as an orthocarboxyphenyl or ortho(sulfonic acid)phenyl group. Exemplary rhodamine-type xanthene dyes can include, but are not limited to, the xanthene rings of the rhodamine dyes described in U.S. Pat. Nos. 5,936,087, 5,750,409, 5,366,860, 5,231,191, 5,840,999, 5,847,162, and 6,080,852 (Lee et al.), PCT Publications WO 97/36960 and WO 99/27020, Sauer et al., J. Fluorescence 5(3):247-261 (1995), Arden-Jacob, Neue Lanwellige Xanthen-Farbstoffe für Fluoreszenzsonden und Farbstoff Laser, Verlag Shaker, Germany (1993), and Lee et al., Nucl. Acids Res. 20:2471-2483 (1992). Also included within the definition of "rhodamine-type xanthene ring" are the extended-conjugation xanthene rings of the extended rhodamine dyes described in U.S. application Ser. No. 09/325,243 filed Jun. 3, 1999.

In some embodiments, the dye comprises a fluorescein-type parent xanthene ring having the structure:

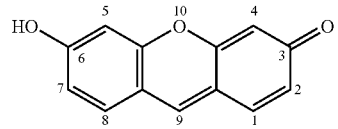

In the fluorescein-type parent xanthene ring depicted above, one or more of the carbons at positions C1, C2, C4, C5, C7, C8 and C9 can be independently substituted with a wide variety of the same or different substituents, as described above for the parent xanthene rings. C9 may be substituted with hydrogen or other substituent, such as an orthocarboxyphenyl or ortho(sulfonic acid)phenyl group. Exemplary fluorescein-type parent xanthene rings include, but are not limited to, the xanthene rings of the fluorescein dyes described in U.S. Pat. Nos. 4,439,356, 4,481,136, 4,933,471 (Lee), U.S. Pat. No. 5,066,580 (Lee), U.S. Pat. Nos. 5,188,934, 5,654,442, and 5,840,999, WO 99/16832, and EP 050684. Also included within the definition of "fluorescein-type parent xanthene ring" are the extended xanthene rings of the fluorescein dyes described in U.S. Pat. Nos. 5,750,409 and 5,066,580. In some embodiments, the dye comprises a rhodamine dye, which can comprise a rhodamine-type xanthene ring in which the C9 carbon atom is substituted with an orthocarboxyphenyl substituent (pendent phenyl group). Such compounds are also referred to herein as orthocarboxyfluoresceins. In some embodiments, a subset of rhodamine dyes are 4,7,-dichlororhodamines. Typical rhodamine dyes can include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichloro-tetramethylrhodamine (dTAMRA). Additional rhodamine dyes can be found, for example, in U.S. Pat. No. 5,366,860 (Bergot et al.), U.S. Pat. No. 5,847,162 (Lee et al.), U.S. Pat. No. 6,017,712 (Lee et al.), U.S. Pat. No. 6,025,505 (Lee et al.), U.S. Pat. No. 6,080,852 (Lee et al.), U.S. Pat. No. 5,936,087 (Benson et al.), U.S. Pat. No. 6,111,116 (Benson et al.), U.S. Pat. No. 6,051,719 (Benson et al.), U.S. Pat. Nos. 5,750,409, 5,366,860, 5,231,191, 5,840,999, and 5,847,162, U.S. Pat. No. 6,248,884 (Lam et al.), PCT Publications WO 97/36960 and WO 99/27020, Sauer et al., 1995, J. Fluorescence 5(3):247-261, Arden-Jacob, 1993, Neue Lanwellige Xanthen-Farbstoffe für Fluoresenzsonden und Farbstoff Laser, Verlag Shaker, Germany, and Lee et al., Nucl. Acids Res. 20(10): 2471-2483 (1992), Lee et al., Nucl. Acids Res. 25:2816-2822 (1997), and Rosenblum et al., Nucl. Acids Res. 25:4500-4504 (1997), for example. In some embodiments, the dye comprises a 4,7-dichloro-orthocarboxyrhodamine. In some embodiments, the dye comprises a fluorescein dye, which comprises a fluorescein-type xanthene ring in which the C9 carbon atom is substituted with an orthocarboxy phenyl substituent (pendent phenyl group). One typical subset of fluorescein-type dyes are 4,7,-dichlorofluoresceins. Typical fluorescein dyes can include, but are not limited to, 5-carboxyfluorescein (5-FAM), 6-carboxyfluorescein (6-FAM). Additional typical fluorescein dyes can be found, for example, in U.S. Pat. Nos. 5,750,409, 5,066,580, 4,439, 356, 4,481,136, 4,933,471 (Lee), U.S. Pat. No. 5,066,580 (Lee), U.S. Pat. No. 5,188,934 (Menchen et al.), U.S. Pat. No. 5,654,442 (Menchen et al.), U.S. Pat. No. 6,008,379 (Benson et al.), and U.S. Pat. No. 5,840,999, PCT publication WO 99/16832, and EPO Publication 050684. In some embodiments, the dye comprises a 4,7-dichloro-orthocarboxyfluorescein. In some embodiments, the dye can be a cyanine, phthalocyanine, squaraine, or bodipy dye, such as described in the following references and references cited therein: U.S. Pat. No. 5,863,727 (Lee et al.), U.S. Pat. No. 5,800,996 (Lee et al.), U.S. Pat. No. 5,945,526 (Lee et al.), U.S. Pat. No. 6,080,868 (Lee et al.), 5,436,134 (Haugland et al.), U.S. Pat. No. 5,863,753 (Haugland et al.), U.S. Pat. No. 6,005,113 (Wu et al.), and WO 96/04405 (Glazer et al.)

As used herein, the term "identifying portion" refers to a moiety or moieties that can be used to identify a particular probe species, and as a result determine a target polynucleotide sequence, and can refer to a variety of distinguishable moieties, including for example zipcodes, a known number of nucleobases, or combinations thereof. In some embodiments, an identifying portion, or an identifying portion complement, can hybridize to a labeling probe, thereby allowing detection of a target polynucleotide sequence in a decoding reaction. In some embodiments, identifying portion refers to an oligonucleotide sequence that can be used for separating the element to which it is bound, including without limitation, bulk separation; for tethering or attaching the element to which it is bound to a substrate, which may or may not include separating; for annealing an identifying portion complement that may comprise at least one moiety, such as a mobility modifier, one or more labels, and combinations thereof. In some embodiments, the same identifying portion is used with a multiplicity of different elements to effect: bulk separation, substrate attachment, and combinations thereof. The terms "identifying portion complement" typically refers to at least one oligonucleotide that comprises at least one sequence of nucleobases that are at least substantially complementary to and hybridize with their corresponding identifying portion. In some embodiments, identifying portion complements serve as capture moieties for attaching at least one identifier portion:element complex to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146, 511, and 6,124,092). Typically, identifying portions and their corresponding identifying portion complements are selected to minimize: internal, self-hybridization; cross-hybridization with different identifying portion species, nucleotide sequences in a reaction composition, including but not limited to gDNA, different species of identifying portion complements, or target-specific portions of probes, and the like; but should be amenable to facile hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. Nos. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

Identifying portions can be located on at least one end of at least one probe, at least one primer, at least one ligation product, at least one ligation product surrogate, and combinations thereof; or they can be located internally. In some embodiments, at least one identifying portion is attached to at least one probe, at least one primer, at least one ligation product, at least one ligation product surrogate, and combinations thereof, via at least one linker arm. In some embodiments, at least one linker arm is cleavable. In some embodiments, the identifying portion is located on the identifying portion of the upstream probes. In some embodiments, identifying portions are at least 12 bases in length, at least 15 bases in length, 12-60 bases in length, or 15-30 bases in length. In some embodiments, at least one identifying portion is 12, 15, 20, 21, 22, 23, 24, 25, 26, 27, 28, 29, 30, 45, or 60 bases in length. In some embodiments, at least two identifying portion: identifying portion complement duplexes have melting temperatures that fall within a $\Delta T_m$ range ($T_{max}$-$T_{min}$) of no more than 10° C. of each other. In some embodiments, at least two identifying portion: identifying portion complement duplexes have melting temperatures that fall within a $\Delta T_m$ range of 5° C. or less of each other. In some embodiments, at least two identifying portion: identifying portion complement duplexes have melting temperatures that fall within a $\Delta T_m$ range of 2° C. or less of each other. In some embodiments, at least one identifying portion or at least one identifying portion complement is used to separate the element to which it is bound from at least one component of a ligation reaction composition, a digestion reaction composition, an amplified ligation reaction composition, or the like. In some embodiments, at least one ligation product, at least one ligation product surrogate, or combinations thereof, comprise the same identifying portion. Examples of separation approaches include but are not limited to, separating a multiplicity of different element: identifying portion species using the same identifying portion complement, tethering a multiplicity of different element: identifying portion species to a substrate comprising the same identifying portion complement, or both. In some embodiments, identifying portions are used to encode a sample, for example a plurality of target polynucleotides in a multiplexed encoding reaction can be encoded with the same identifying portion, thereby marking the polynucleotides from a given sample with a given target identifying portion.

As used herein, the term "ligation agent", according to the present teachings, can comprise any number of enzymatic or non-enzymatic reagents. For example, ligase is an enzymatic ligation reagent that, under appropriate conditions, forms phosphodiester bonds between the 3'-OH and the 5'-phosphate of adjacent nucleotides in DNA molecules, RNA molecules, or hybrids. Temperature sensitive ligases, include, but are not limited to, bacteriophage T4 ligase and *E. coli* ligase. Thermostable ligases include, but are not limited to, Afu ligase, Taq ligase, Tfl ligase, Tth ligase, Tth HB8 ligase, *Thermus* species AK16D ligase and Pfu ligase (see for example Published P.C.T. Application WO00/26381, Wu et al., Gene, 76(2):245-254, (1989), Luo et al., Nucleic Acids Research, 24(15): 3071-3078 (1996). The skilled artisan will appreciate that any number of thermostable ligases, including DNA ligases and RNA ligases, can be obtained from thermophilic or hyperthermophilic organisms, for example, certain species of eubacteria and archaea; and that such ligases can be employed in the disclosed methods and kits.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in, among other places, Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowski, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); and U.S. Pat. No. 5,476,930.

Photoligation using light of an appropriate wavelength as a ligation agent is also within the scope of the teachings. In some embodiments, photoligation comprises probes comprising nucleotide analogs, including but not limited to, 4-thiothymidine ($s^4T$), 5-vinyluracil and its derivatives, or combinations thereof. In some embodiments, the ligation agent comprises: (a) light in the UV-A range (about 320 nm to about 400 nm), the UV-B range (about 290 nm to about 320 nm), or combinations thereof, (b) light with a wavelength between about 300 nm and about 375 nm, (c) light with a wavelength of about 360 nm to about 370 nm; (d) light with a wavelength of about 364 nm to about 368 nm, or (e) light with a wavelength of about 366 nm. In some embodiments, photoligation is reversible. Descriptions of photoligation can be found in, among other places, Fujimoto et al., Nucl. Acid Symp. Ser. 42:39-40 (1999); Fujimoto et al., Nucl. Acid Res. Suppl. 1:185-86 (2001); Fujimoto et al., Nucl. Acid Suppl., 2:155-56 (2002); Liu and Taylor, Nucl. Acid Res. 26:3300-04 (1998) and on the world wide web at: sbchem.kyoto-u.ac.jp/saito-lab.

As used herein, "labeling probe" generally refers to a molecule used in a decoding reaction, typically for quantitative or real-time PCR analysis, as well as end-point analysis. Such labeling probes can be used to monitor the amplification of the target polynucleotide. In some embodiments, oligonucleotide probes present in an amplification reaction are suitable for monitoring the amount of amplicon(s) produced as a function of time. Such oligonucleotide probes include, but are not limited to, the 5'-exonuclease assay (TAQMAN®) probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA MOLECULAR BEACONS™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), SUNRISE®/AMPLIFUOR® probes (U.S. Pat. No. 6,548,250), stem-loop and duplex SCORPION™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB ECLIPSE™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Labeling probes can also comprise black hole quenchers (Biosearch), IOWA BLACK (IDT), QSY quencher (Molecular Probes), and Dabsyl and Dabcel sulfonate/carboxylate Quenchers (Epoch). Labeling probes can also comprise two probes, wherein for example a flore is on one probe, and a quencher on the other, wherein hybridization of the two probes together on a target quenches the signal, or wherein hybridization on target alters the signal signature via a change in floresence. Labeling probes can also comprise sulfonate derivatives of fluorescenin dyes with SO3 instead of the carboxylate group, phosphoramidite forms of fluorescein, phosphoramidite forms of CY 5 (available for example from Amersham). In some embodiments, interchelating labels are used such as ethidium bromide, SYBR® Green I (Molecular Probes), and PICOGREEN® (Molecular Probes), thereby allowing visualization in real-time, or end point, of an amplification product in the absence of a labeling probe.

As used herein, "addressable primer portion" refers to at least one region of a probe or probe set that can encode the identity of a given target polynuceotide, and allow for an address primer or address primer set in a decoding reaction to selectively amplify a target polynucleotide encoded with particular addressable primer portions in an encoding reaction.

As used herein, "address primer" refers to at least one primer in a decoding amplification reaction that can hybridize to at least one addressable primer portion in the product of an encoding reaction. In some embodiments, a given decoding reaction can comprise an address primer set, wherein the address primer set can amplify a given encoding reaction product based on the identity of the addressable primer portions incorporated therein during the encoding reaction. In some embodiments, a plurality of decoding reactions can be performed on the same solid support (for example a 96 well or 384 microtitre plate, or an Applied Biosystems Low Density Expression Array, Microcard), wherein each decoding reaction comprises a distinct address primer set, wherein the address primer set can amplify a given target polynucleotide in a give decoding reaction based on the addressable primer portions present in the target and the particular address primer set in the decoding reaction.

As used herein, "primer set" refers to at least one, typically two, primers that can selectively amplify a given target polynucleotide based on the addressable primer portion contained therein as a result of at least one encoding reaction. A variety of primer sets are possible, hence the term "battery of primer sets." A given primer set can be used in one application to encode a particular target polynucleotide, and used in a different application to encode a different target polynucleotide. For one illustrative example of various batteries of address primer sets, see FIG. 17.

As used herein the term "primary looped linker" refers to an oligonucleotdie comprising a self-complementary portion, a loop, and a single-stranded portion. As an example, an "ASO looped linker" refers to a primary looped linker comprising a PCR forward priming portion, a blocking moiety, and a single stranded portion, and can be considered an allele specific oligonucleotide. The single stranded portion of an ASO looped linker can hybridize with a region of the target-identifying portion of the ASO (an allele specific oligonucleotide, basically an upstream ligation probe) thereby allowing ligation of the ASO looped linker to the ASO. For illustrative purposes, when depicted herein a blocking moiety is shown residing in the loop that can confer nuclease resistance, though it will be appreciated that the present teachings contemplate embodiments in which the blocking moiety is located elsewhere. In some embodiments, especially those involving multiplexed analysis, the 3' nucleotide in a plurality of primary looped linkers is the same, which can minimize variation in ligation efficiency to the plurality of upstream ligation probes.

As used herein the term "secondary looped linker" refers to an oligonucleotide comprising a self-complementary portion, a loop, and a single-stranded portion. As an example, an "LSO looped linker" refers to a secondary looped linker comprising a PCR reverse priming portion, a blocking moiety, and a single stranded portion, and can be considered a locus specific oligonucleotide. The single stranded portion of an LSO looped linker can hybridize with a region of the non-target specific portion of the LSO (a locus specific oligonucleotide, basically an LSO), thereby allowing ligation of the LSO looped linker to the LSO. In some embodiments of the present teachings, the secondary looped linker can be referred to as a "universal looped linker," and can be used to introduce sequence information and/or confer nuclease resistance by its ligation to any of a plurality of ligation probes (e.g.—LSOs) by a universal splint (US) present on the 3' end of an LSO (see for example FIG. 11B).

As used herein, the term "3'-acting" nuclease refers to an enzyme that degrades oligonucleotides by commencing digestion at or near the 3' end, for example exonuclease I.

As used herein, the term "5'-acting" nuclease refers to an enzyme that degrades oligonucleotides by commencing digestion at or near the 5' end, for example lambda exonuclease.

As used herein, the term "encoding reaction" refers to reaction in which at least one target polynucleotide is queried with a probe set, wherein the identity of the target polynucleotide is encoded into the reaction product. For example, an "encoding PCR" can comprise a PCR in which the at least one probe comprises a target specific portion and an addressable primer portion located on the 5' end of the target specific portion, and at least one second probe that comprises a target specific portion and an addressable primer portion located on the 5' end of the target specific portion. One, or both, of the probes in an encoding PCR can further comprise an "identifying portion" which can be used by a complementary labeling probe to produce signal in a decoding reaction. For illustrative examples of PCR protocols applicable to encoding PCR, see pending WO Application U03/37808 as well as U.S. Pat. No. 6,605,451. Also, and encoding reaction can refer to an "encoding ligation" reaction that can comprise a ligation reaction in which at least one one probe comprises a target specific portion and an addressable primer portion located on the 5' end of the target specific portion, and at least one second probe that comprises a target specific portion and an addressable primer portion located on the 5' end of the target specific portion. One, or both, of the probes in an encoding PCR can further comprise an "identifying portion" which can be used by a complementary labeling probe to produce signal in a decoding reaction. In some embodiments, the location on which the labeling probes hybridize to the products of an encoding reaction can comprise all the identifying portion, some of the identifying portion, some of the identifying portion and some of the primer portion, and in general it will be appreciated that sliding the placement of the labeling probe relative to the products of the encoding reaction products are contemplated by the present teachings, and can have the aspect, for example, of reducing the length (size) of primers or probes in an encoding reaction.

As used herein, the term "decoding reaction" refers to at least one reaction comprising at least one address primer or address primer set, wherein the address primer or address primer set can amplify a target polynucleotide, or target polynucleotide surrogate, based on the addressable primer portions incorporated therein by probes during an encoding reaction, thereby producing signal indicative of the presence of a target polynucleotide in a sample. A decoding reaction can further comprise at least one labeling probe, wherein the labeling probe can hybridize to at least one identifying portion, or identifying portion complement, introduced in the encoding reaction to confer for example the identity of a sample, or the identity of an allelic variant, as is appropriate in the context of the given embodiment.

As used herein, the term "determine" and "determining" can comprise detecting, quantifying, identifying, or combinations thereof.

As used herein, the term "reaction vessel" generally refers to any container in which a reaction can occur in accordance with the present teachings. In some embodiments, the first reaction vessel can be an eppendorf tube, and other containers of the sort in common practice in modern molecular biology laboratories. In some embodiments, the second reaction vessel can be a well in microtitre plate, a spot on a glass slide, or a well in an Applied Biosystems low density gene expression array (Microcard). For example, a plurality of second reaction vessels can reside on the same support. Also, a plurality of first reaction vessels can reside on the same support. In some embodiments, the first reaction vessel and second reaction vessel can be on the same solid support in lab-on-a-chip like devices, available for example from Caliper and Fluidgm. It will be recognized that a variety of reaction vessel are available in the art and within the scope of the present teachings.

An "aliquot" according to the present teachings refers generally to a portion, up to and including all, of something. For example, an aliquot of the encoding reaction products can be placed in at least one separate decoding reaction.

Figure 2:
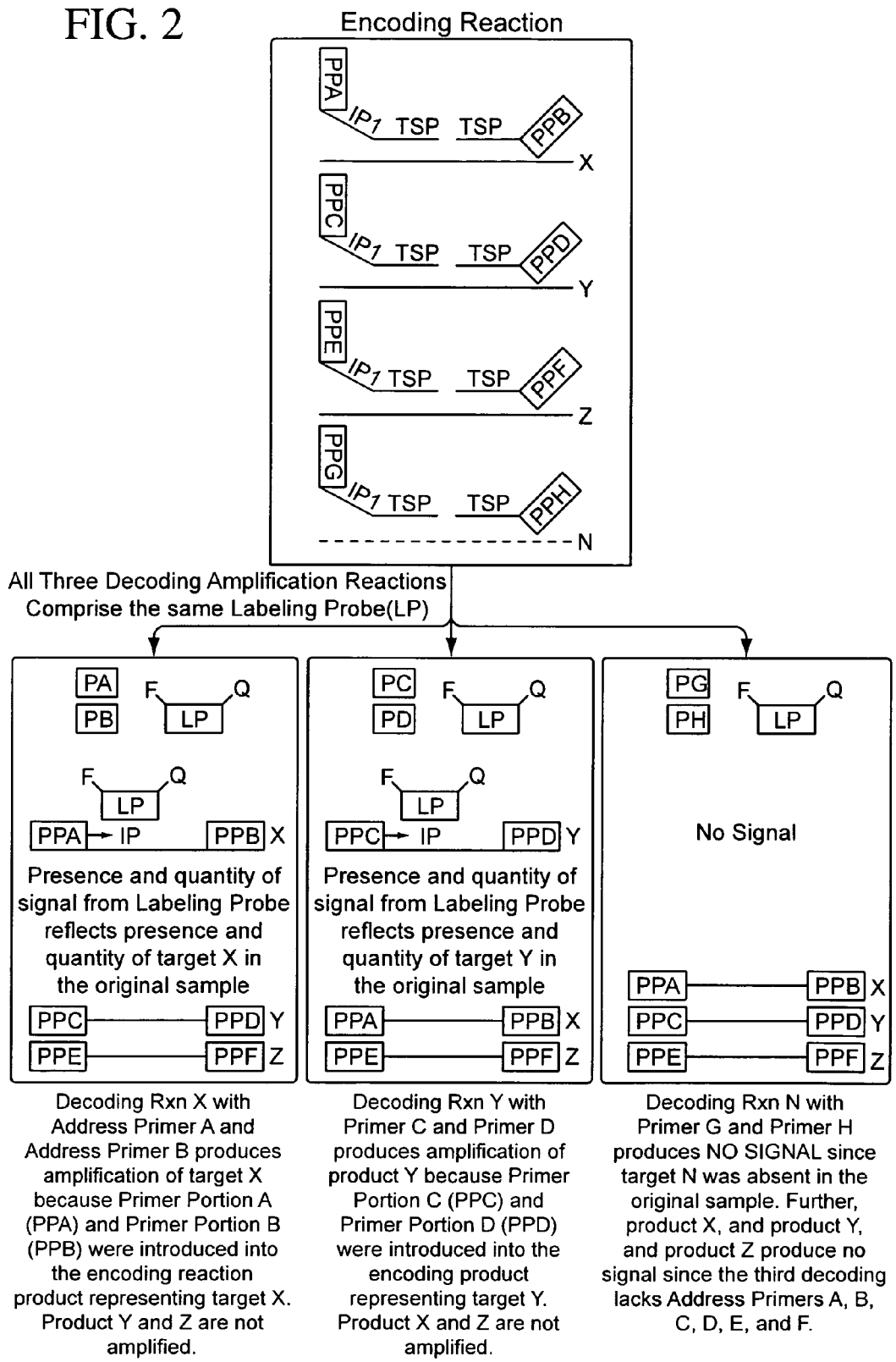
FIG. 2 depicts certain compositions and reaction interactions in accordance with some embodiments of the present teachings.
Figure 3A:
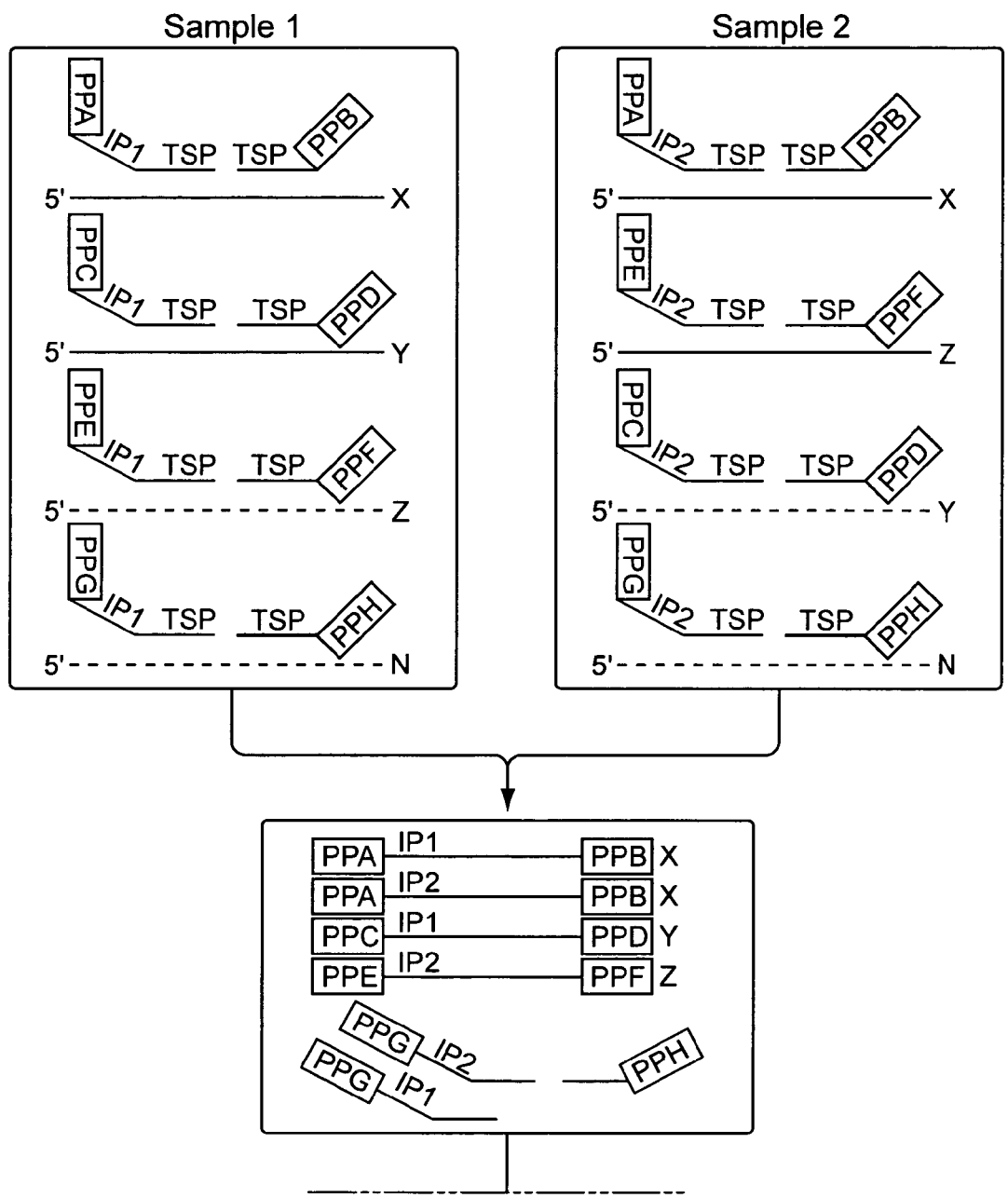
FIG. 3 depicts certain compositions and reaction interactions in accordance with some embodiments of the present teachings.
Figure 3B:
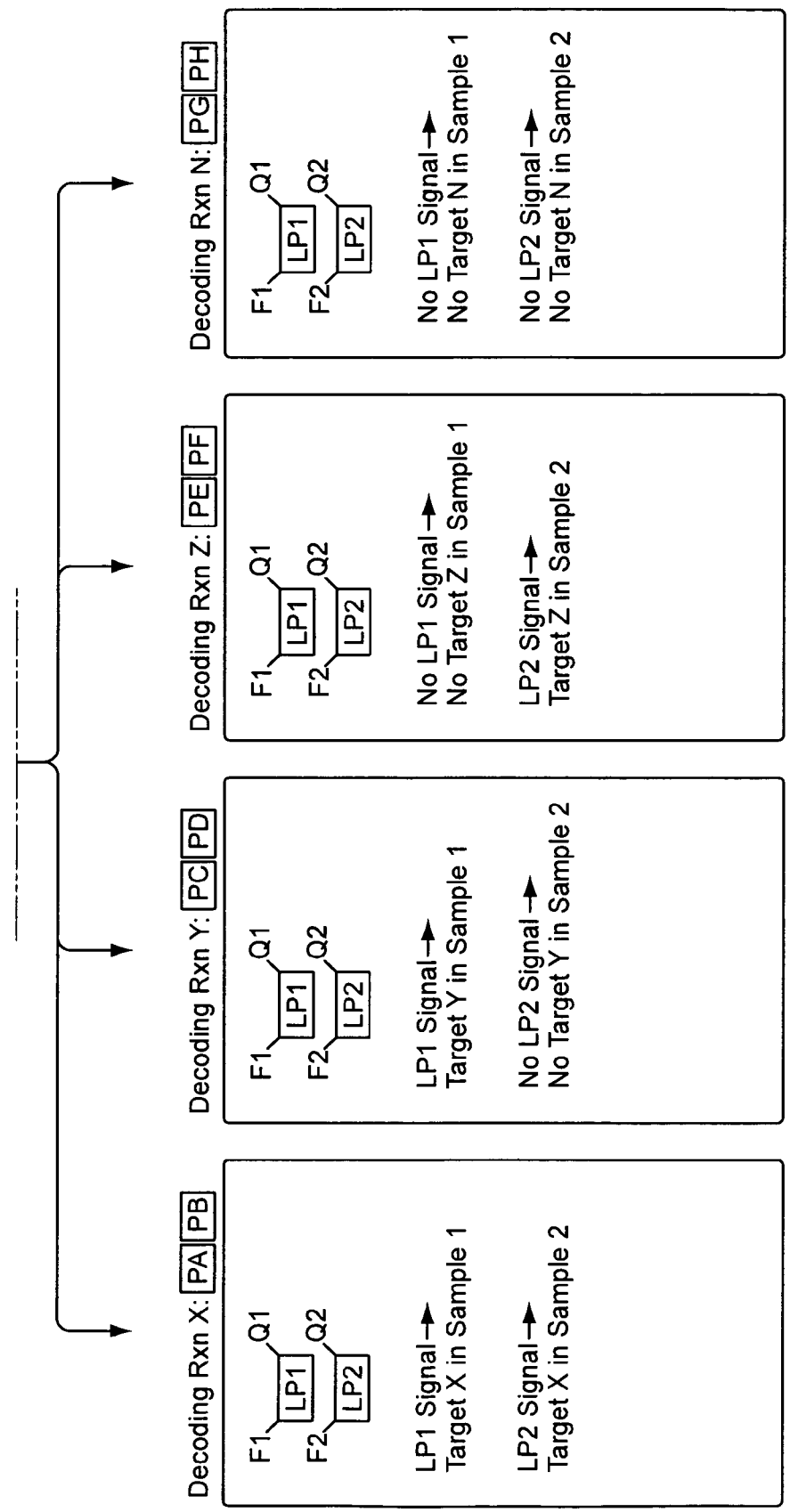

A "ligation probe set", according to some embodiments herein, comprises two or more probes that comprise a target-specific portion that is designed to hybridize in a sequence-specific manner with a complementary region on a specific target nucleic acid sequence (see, e.g., probes 2 and 3 in FIG. 2). A probe of a ligation probe set can further comprise an addressable primer portion, an identifying portion, or a combination of these additional components. In some embodiments, any of the probe's components may overlap any other probe component(s). For example, but without limitation, the target-specific portion may overlap the addressable primer portion. Also, without limitation, the identifying portion can overlap with the target-specific portion or the addressable primer portion, or both.

According to some embodiments of the present teachings, a ligation probe set is designed so that the target-specific portion of the first probe will hybridize with the downstream target region and the target-specific portion of the second probe will hybridize with the upstream target region. In some embodiments, a nucleotide base complementary to the variant base, the "discriminating nucleotide" or "discriminating nucleotide complement," is present on the 5'end of the second probe of the ligation probe set. In some embodiments, the first probe can comprise an identifying portion and a discriminating nucleotide or discriminating nucleotide complement on it its 3' end, rather than the second probe. The skilled artisan will appreciate that, in various embodiments, the discriminating nucleotide(s) can be located anywhere in the target polynucleotide and that likewise, the discriminating nucleotide complement(s) can be located anywhere within the target-specific portion of the probe(s). For example, according to various embodiments, the discriminating nucleotide can be located at the 3' end of a probe, at the 5' end of a probe, or anywhere between the 3' end and the 5' end of a probe.

In some embodiments, when the first and second probes of the ligation probe set are hybridized to the appropriate upstream and downstream target regions, and when the discriminating nucleotide is at the 5' end of one probe or the 3' end of the other probe, and the discriminating nucleotide is base-paired with the discriminating nucleotide complement on the target sequence, the hybridized first and second probes can be ligated together to form a ligation product. Further, a mismatched base at the discriminating nucleotide, however, interferes with ligation, even if both probes are otherwise fully hybridized to their respective target regions.

In some embodiments, other mechanisms may be employed to avoid ligation of probes that do not include the correct complementary nucleotide at the discriminating nucleotide. For example, in some embodiments, conditions can be employed such that a probe of a ligation probe set can hybridize to the target sequence to a measurably lesser extent if there is a mismatch at the discriminating nucleotide. Thus, in such embodiments, such non-hybridized probes will not be ligated to the other probe in the probe set.

In some embodiments, the first probes and second probes in a ligation probe set are designed with similar melting temperatures ($T_m$). Where a probe includes a discriminating nucleotide, in some embodiments, the $T_m$ for the probe(s) comprising the discriminating nucleotide(s) of the target discriminating nucleotide complement sought will be approximately 4-15° C. lower than the other probe(s) that do not contain the discriminating nucleotide in the probe set. In some such embodiments, the probe comprising the discriminating nucleotide(s) can also be designed with a $T_m$ near the ligation temperature. Thus, a probe with a mismatched nucleotide will more readily dissociate from the target at the ligation temperature. The ligation temperature, therefore, in some embodiments provides another way to discriminate between, for example, multiple potential alleles in the target.

Further, in some embodiments, ligation probe sets do not comprise a discriminating nucleotide at the terminus of the first or the second probe (e.g., at the 3' end or the 5' end of the first or second probe). Rather, the discriminating nucleotide is located somewhere between the 5' end and the 3' end of the first or second probe. In some such embodiments, probes with target-specific portions that are fully complementary with their respective target regions will hybridize under high stringency conditions. Probes with one or more mismatched bases in the target-specific portion, by contrast, will hybridize to their respective target region to a measurably lesser extent. Both the first probe and the second probe must be hybridized to the target for a ligation product to be generated.

2. Techniques

Ligation

Ligation according to the present teachings comprises any enzymatic or non-enzymatic means wherein an inter-nucleotide linkage is formed between the opposing ends of nucleic acid sequences that are adjacently hybridized to a template. Typically, the opposing ends of the annealed nucleic acid probes are suitable for ligation (suitability for ligation is a function of the ligation means employed). In some embodiments, ligation also comprises at least one gap-filling procedure, wherein the ends of the two probes are not adjacently hybridized initially but the 3'-end of the upstream probe is extended by one or more nucleotide until it is adjacent to the 5'-end of the downstream probe, typically by a polymerase (see, e.g., U.S. Pat. No. 6,004,826). The internucleotide linkage can include, but is not limited to, phosphodiester bond formation. Such bond formation can include, without limitation, those created enzymatically by at least one DNA ligase or at least one RNA ligase, for example but not limited to, T4 DNA ligase, T4 RNA ligase, *Thermus thermophilus* (Tth) ligase, *Thermus aquaticus* (Taq) DNA ligase, *Thermus scotoductus* (Tsc) ligase, TS2126 (a thermophilic phage that infects Tsc) RNA ligase, *Archaeoglobus flugidus* (Afu) ligase, *Pyrococcus furiosus* (Pfu) ligase, or the like, including but not limited to reversibly inactivated ligases (see, e.g., U.S. Pat. No. 5,773,258), and enzymatically active mutants and variants thereof.

Other internucleotide linkages include, without limitation, covalent bond formation between appropriate reactive groups such as between an α-haloacyl group and a phosphothioate group to form a thiophosphorylacetylamino group, a phosphorothioate a tosylate or iodide group to form a 5'-phosphorothioester, and pyrophosphate linkages.

Chemical ligation can, under appropriate conditions, occur spontaneously such as by autoligation. Alternatively, "activating" or reducing agents can be used. Examples of activating and reducing agents include, without limitation, carbodiimide, cyanogen bromide (BrCN), imidazole, 1-methylimidazole/carbodiimide/cystamine, N-cyanoimidazole, dithiothreitol (DTT) and ultraviolet light, such as used for photoligation.

Ligation generally comprises at least one cycle of ligation, i.e., the sequential procedures of: hybridizing the target-specific portions of a first probe and a corresponding second probe to their respective complementary regions on the corresponding target nucleic acid sequences; ligating the 3' end of the upstream probe with the 5' end of the downstream probe to form a ligation product; and denaturing the nucleic acid duplex to release the ligation product from the ligation product:target nucleic acid sequence duplex. The ligation cycle may or may not be repeated, for example, without limitation, by thermocycling the ligation reaction to amplify the ligation product using ligation probes (as distinct from using primers and polymerase to generate amplified ligation products).

Also within the scope of the teachings are ligation techniques such as gap-filling ligation, including, without limitation, gap-filling versions OLA, LDR, LCR, FEN-cleavage mediated versions of OLA, LDR, and LCR, bridging oligonucleotide ligation, correction ligation, and looped linker-based concatameric ligation. Descriptions of these techniques can be found in, among other places, U.S. Pat. Nos. 5,185,243 and 6,004,826, 5,830,711, 6,511,810, 6,027,889; published European Patent Applications EP 320308 and EP 439182; Published PCT applications WO 90/01069, WO 01/57268, WO0056927A3, WO9803673A1, WO200117329, Landegren et al., Science 241:1077-80 (1988), Day et al., Genomics, 29(1): 152-162 (1995), de Arruda et al., and U.S. Application 60/517470. In some embodiments ligation can provide for sample preparation prior to a subsequent amplification step. In some embodiments ligation can provide amplification in and of itself, as well as provide for an initial amplification followed by a subsequent amplification.

In some embodiments of the present teachings, unconventional nucleotide bases can be introduced into the ligation probes and the resulting products treated by enzymatic (e.g., glycosylases) and/or physical-chemical means in order to render the product incapable of acting as a template for subsequent downstream reactions such as amplification. In some embodiments, uracil can be included as a nucleobase in the ligation reaction mixture, thereby allowing for subsequent reactions to decontaminate carryover of previous uracil-containing products by the use of uracil-N-glycosylase. Various approaches to decontamination using glycosylases and the like can be found for example in Published P.C.T. Application WO9201814A2.

Methods for removing unhybridized and/or unligated probes following a ligation reaction are known in the art, and are further discussed infra. Such procedures include nuclease-mediated approaches, dilution, size exclusion approaches, affinity moiety procedures, (see for example U.S. Provisional Application 60/517470, U.S. Provisional Application 60/477614, and P.C.T. Application 2003/37227), affinity-moiety procedures involving immobilization of target polynucleotides (see for example Published P.C.T. Application WO 03/006677A2).

Removal of Unincorporated and/or Undesired Reaction Components

It will be appreciated that reactions involving complex mixtures of nucleic acids in which a number of reactive steps are employed can result in a variety of unincorporated reactions components, and that removal of such unincorporated reaction components by any of a variety of complexity reduction procedures can improve the efficiency and specificity or subsequently occurring reactions.

In some embodiments, complexity reduction includes selective immobilization of target nucleic acids. For example, target nucleic acids can be preferentially immobilized on a solid support. In some embodiments, photo-biotin can be attached to target nucleic acids, and the resulting biotin-labeled nucleic acids immobilized on a solid support comprising an affinity-moiety binder such as streptavidin. Immobilized target nucleic acids can be queried with probes, and non-hybridized and/or non-ligated probes removed by washing (See for Example Published P.C.T. Application WO 03/006677 and USSN 09/931,285, for further elaboration on such complexity reduction approaches). A variety of washing conditions can be employed, as described for example in recent editions of Ausubel et al., and Maniatis et al.

In some embodiments, unincorporated probes can be removed by a variety of enzymatic means, wherein for example unprotected 3' probe ends can be digested with 3'-acting nucleases, 5' phosphate-bearing probes ends can be digested with 5'Phosphate-acting nucleases (for example, Lambda exonuclease). In some embodiments, such nuclease-digestion mediated approaches to removal of unincorporated reaction components such as ligation probes can further comprise the use of looped-linker based probes, and single-stranded linker-based probes, as described for example in U.S. application 60/517,470.

In some embodiments, unreacted ligation probes can be removed from the mixture whereby the upstream probe can comprise a label and the downstream probe can be blocked at its 3' end with an exonuclease blocking moiety. After ligation and the introduction of the nuclease, the labeled unligated upstream probe can be digested, leaving the ligation product and the downstream probe. However, since the downstream probe is unlabelled, it is effectively silent in the assay. In some embodiments, the target nucleic acids are immobilized, and the ligation product can be eluted and detected. In some embodiments, the 3' end of the downstream probe further comprises an affinity moiety, and the ligation products and unincorporated downstream probes can be immobilized with an affinity-moiety binder. In some embodiments, the 5' end of the upstream probe further comprises an affinity moiety, and the ligation products and unincorporated upstream probes can be immobilized with an affinity-moiety binder.

In some embodiments, products from previous reactions performed for example in the same laboratory workspace can contaminate a reaction of interest. In some embodiments, uracil can be incorporated into for example a PCR amplification step, thereby rendering reaction products comprising uracil instead of, or along with, thymidine. In some embodiments, uracil-N-glycosylase can be included in the OLA reaction mixture is such fashion as to degrade uracil-containing contaminants.

Amplification

Amplification according to the present teachings encompasses any means by which at least a part of at least one target polynucleotide, ligation product, at least one ligation product surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other places, Sambrook and Russell; Sambrook et al.; Ausbel et al.; PCR Primer: A Laboratory Manual, Diffenbach, Ed., Cold Spring Harbor Press (1995); The Electronic Protocol Book, Chang Bioscience (2002)("The Electronic Protocol Book"); Msuih et al., J. Clin. Micro. 34:501-07 (1996); The Nucleic Acid Protocols Handbook, R. Rapley, ed., Humana Press, Totowa, N.J. (2002)("Rapley"); Abramson et al., Curr Opin Biotechnol. 1993 Feb.;4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at the Promega website; LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 Feb.;13(2):294-307, and Landegren et al., Science 241:1077-80 (1988), Demidov, V., Expert Rev Mol Diagn. 2002 Nov.;2(6):542-8., Cook et al., J Microbiol Methods. 2003 May;53(2):165-74, Schweitzer et al., Curr Opin Biotechnol. 2001 Feb.;12(1):21-7, U.S. Pat. No. 5,830,711, U.S. Pat. No. 6,027,889, U.S. Pat. No. 5,686,243, Published P.C.T. Application WO0056927A3, and Published P.C.T. Application WO9803673A1.

In some embodiments, amplification comprises at least one cycle of the sequential procedures of: hybridizing at least one primer with complementary or substantially complementary sequences in at least one ligation product, at least one ligation product surrogate, or combinations thereof; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally. In some embodiments, newly-formed nucleic acid duplexes are not initially denatured, but are used in their double-stranded form in one or more subsequent steps.

Primer extension is an amplifying means that comprises elongating at least one probe or at least one primer that is annealed to a template in the 5' to 3' direction using an amplifying means such as a polymerase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed probe or primer, to generate a complementary strand. In some embodiments, primer extension can be used to fill a gap between two probes of a probe set that are hybridized to target sequences of at least one target nucleic acid sequence so that the two probes can be ligated together. In some embodiments, the polymerase used for primer extension lacks or substantially lacks 5' exonuclease activity.

In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol Biotechnol. 2004 Feb.;26(2):133-46. In some embodiments, amplification can be achieved in a self-contained integrated approach comprising sample preparation and detection, as described for example in U.S. Pat. Nos. 6,153,425 and 6,649,378.

Detection

In some embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of some such combinations of a donor and an acceptor have also been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, and 6-Fam™(all available from Applied Biosystems, Foster City, Calif.)

In some embodiments, the amount of labeling probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems, Foster City, Calif.).

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification.

According to some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide.

According to some embodiments, the amplification products can be scored as positive or negative as soon as a given number of cycles is complete. In some embodiments, the results may be transmitted electronically directly to a database and tabulated. Thus, in some embodiments, large numbers of samples may be processed and analyzed with less time and labor required.

According to some embodiments, different labeling probes may distinguish between different target nucleic acid sequences. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different identifying portions of two different ligation products (A' and B', respectively). Ligation product A' is formed if target nucleic acid sequence A is in the sample, and ligation product B' is formed if target nucleic acid sequence B is in the sample. In some embodiments, ligation product A' and/or B' may form even if the appropriate target nucleic acid sequence is not in the sample, but such ligation occurs to a measurably lesser extent than when the appropriate target nucleic acid sequence is in the sample. After amplification, one can determine which specific target nucleic acid sequences are present in the sample based on the wavelength of signal detected. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B.

Aspects of the present teachings may be further understood in light of the following examples, which should not be construed as limiting the scope of the teachings in any way.

3. Exemplary Embodiments

The present invention is directed to methods, reagents, and kits for detecting the presence or absence of (or quantifying) target polynucleotide sequences, target proteins, and other molecules of interest in at least one sample using encoding and decoding reactions. When a particular target nucleic acid sequence is present in a sample, a reaction product is formed in the encoding reaction that includes addressable primer portions. At least one label is employed in the decoding amplification reaction that can provide a detectable signal value depending upon whether a sequence is present or absent.

A non-limiting illustrative schematic is shown in FIG. 1A. Here, a given target polynucleotide of interest X can be queried in an encoding ligation reaction with a first probe comprising a 5' addressable primer portion A (PPA) and a target specific portion (TSP), and a second probe comprising a target specific portion (TSP) and a 3' addressable primer portion B (PPB). Also in the first encoding ligation reaction, a given target polynucleotide of interest Y can be queried with a first probe comprising a 5' addressable primer portion C (PPC) and a second probe comprising a target specific portion (TSP), and a 3' addressable primer portion D (PPD). Also in the first encoding ligation reaction, a given target polynucleotide of interest N (shown in dotted lines to indicate that it is absent from the sample) can be queried with a first probe comprising a 5' addressable primer portion E (PPE) and a target specific portion (TSP), and a second probe comprising a target specific portion (TSP) and a 3' addressable primer portion F (PPF). In such a scheme, the identity of given target polynucleotide can be encoded with the addressable primer portions.

After the encoding ligation reaction is performed, the reaction products can be split into at least three decoding amplification reactions (here, PCR amplification reactions). A first decoding amplification reaction comprises an address primer A (PA), an address primer B (PB), and a label (for example, SYBR® Green), a second decoding amplification reaction comprises an address primer C (PC), address primer D (PD), and a label, and a third decoding amplification reaction comprises an address primer E (PE), address primer F (PF), and a label. Each decoding amplification reaction can result in the production of signal from the label. The quantity of signal produced by the label in any given decoding amplification reaction can provide a quantifiable measure of the amount of a given target polynucleotide in the sample, as conferred by the given address primers in a given decoding reaction. In the present embodiment, the first decoding amplification reaction allows for a quantification of gene X in the sample based on the quantity of signal from the label. The second decoding amplification reaction allows for a quantification of gene Y in the sample based on the quantity of signal from the label. The third decoding amplification reaction allows for a detection of the absence of target polynucleotide N in the sample based on the relative absence of signal from the label. In such a scheme, the identity of given expressed gene can be encoded with the addressable primer portions, and the ability to detect and quantify target polynucleotides in a sample assessed by the signal derived from a single label.

In some embodiments, a reaction product is formed in the encoding reaction that includes an identifying portion in addition to the addressable primer portions, and labeling probes are employed in the decoding amplification reaction that provide a different detectable signal value depending upon whether a corresponding identifying portion sequence is present or absent during the decoding amplification reaction (See illustrative schematic in FIG. 1B).

As depicted in FIG. 1B, a given target polynucleotide of interest X can be queried in an encoding ligation reaction with a first probe comprising a 5' addressable primer portion A (PPA), an identifying portion 1 (IP 1), and a target specific portion (TSP), and a second probe comprising a target specific portion (TSP) and a 3' addressable primer portion B (PPB). Also in the first encoding ligation reaction, a given target polynucleotide of interest Y can be queried with a first probe comprising a 5' addressable primer portion C (PPC) and an identifying portion 1 (IP 1), and a second probe comprising a target specific portion (TSP), and a 3' addressable primer portion D (PPD). Also in the first encoding ligation reaction, a given target polynucleotide of interest Z can be queried with a first probe comprising a 5' addressable primer portion E (PPE) and an identifying portion 1 (IP 1), and a second probe comprising a target specific portion (TSP), and a 3' addressable primer portion D (PPF). Also in the first encoding ligation reaction, a given target polynucleotide of interest N (shown in dotted lines to indicate that it is absent from the sample) can be queried with a first probe comprising a 5' addressable primer portion C (PPG) and an identifying portion 1 (IP 1), and a second probe comprising a target specific portion (TSP), and a 3' addressable primer portion H (PPH). In such a scheme, the identity of given target polynucleotide can be encoded with the addressable primer portions.

After the encoding ligation reaction is performed, the reaction products can be split into at least three decoding amplification reactions (here, PCR amplification reactions). A first decoding amplification reactions comprises an address primer A (PA), an address primer B (PB), and a labeling probe (here a cleaveable TaqMan® probe) a second decoding amplification reaction comprises an address primer C (PC), address primer D (PD), and a labeling probe, and a third decoding amplification reaction comprises an address primer E (PE), address primer F (PF), and a labeling probe. Each decoding amplification reaction comprises the same labeling probe and can result in the production of signal from the labeling probe. The quantity of signal produced by the labeling probe in any given decoding amplification reaction can provide a quantifiable measure of the amount of a given target polynucleotide in the sample, as conferred by the given address primers in a given decoding reaction. In the present embodiment, the first decoding amplification reaction allows for a quantification of gene X in the sample based on the quantity of signal from the labeling probe. The second decoding amplification reaction allows for a quantification of gene Y in the sample based on the quantity of signal from the labeling probe. The third decoding amplification reaction allows for a detection of the absence of target polynucleotide N in the sample based on the relative absence of signal from the labeling probe. In such a scheme, the identity of given expressed gene can be encoded with the addressable primer portions, and the ability to detect and quantify target polynucleotides in a sample assessed by the signal derived from a single labeling probe.

In some embodiments, at least two samples are analyzed by at least two encoding reactions, wherein each sample is encoded with an identifying portion, and each target polynucleotide is encoded with the addressable primer portions. Labeling probes can be employed in the decoding amplification reaction to provide a different detectable signal value depending upon whether a given target polynucleotide sequence is derived from a given sample. (See illustrative schematic in FIG. 1C).

A depicted in FIG. 1C, a given gene of interest X in Sample 1 can be queried in a first encoding reaction with a first probe comprising a 5' addressable primer portion A (PPA), an identifying portion 1 (IP 1), and target specific portion (TSP), and a second probe comprising a target specific portion (TSP) and a 3' addressable primer portion B (PPB). Also in the first encoding reaction, a given gene of interest Y can be queried with a first probe comprising a 5' addressable primer portion C, an identifying portion 1 (IP 1), and a target specific portion (TSP), and a second probe comprising a target specific portion (TSP) and a 3' addressable primer portion D (PPD). Also in the first encoding reaction, a given gene of interest Z (shown in dotted lines to indicate that it is absent from Sample 1) can be queried with a first probe comprising a 5' addressable primer portion E (PPE), an identifying portion 1 (IP 1), and a target specific portion (TSP), and a second probe comprising a target specific portion (TSP) and a 3' addressable primer portion F (PPF). Also in the first encoding reaction, a given gene of interest N (shown in dotted lines to indicate that it is absent from Sample 1) can be queried with a first probe comprising a 5' addressable primer portion G (PPG), an identifying portion 1 (IP 1), and a target specific portion (TSP), and a second probe comprising a target specific portion (TSP) and a 3' addressable primer portion H (PPH).

In a second encoding reaction for Sample 2, a given gene of interest X in Sample 2 can be queried in a second encoding reaction with a first probe comprising a 5' addressable primer portion A (PPA), an identifying portion 2 (IP 2), and target specific portion (TSP), and a second probe comprising a target specific portion (TSP) and a 3' addressable primer portion B (PPB). Also in the second encoding reaction, a given gene of interest Y (shown in dotted lines to indicate that it is absent from Sample 2) can be queried with a first probe comprising a 5' addressable primer portion C(PPC), an identifying portion 2 (IP 2), and a target specific portion (TSP), and a second probe comprising a target specific portion (TSP) and a 3' addressable primer portion D (PPD). Also in the second encoding reaction, a given gene of interest Z can be queried with a first probe comprising a 5' addressable primer portion E (PPE), an identifying portion 2 (IP 2), and a target specific portion (TSP), and a second probe comprising a target specific portion (TSP) and a 3' addressable primer portion F (PPF). Also in the second encoding reaction, a given gene of interest N (shown in dotted lines to indicate that it is absent from Sample 2) can be queried with a first probe comprising a 5' addressable primer portion G (PPG), an identifying portion 2 (IP 1), and a target specific portion (TSP), and a second probe comprising a target specific portion (TSP) and a 3' addressable primer portion H (PPH).

After the first and second encoding ligation reactions are performed, the reactions can be combined together. The combined encoding reactions can then be split into at least four decoding amplification reactions (see FIG. 1C Continued). The decoding amplification reactions can comprise a first decoding amplification reaction comprising an address primer A (PA), an address primer B (PB), a labeling probe 1 (LP1), a labeling probe 2 (LP2), a second decoding amplification reaction comprising an address primer C (PC), address primer D (PD), the labeling probe 1 (LP1), and the labeling probe 2 (LP2), a third decoding amplification reaction comprising an address primer E (PE), address primer F (PF), the labeling probe 1 (LP1), and the labeling probe 2(LP2), and a fourth decoding amplification reaction comprising an address primer G (PG), address primer H (PH), the labeling probe 1 (LP1), and the labeling probe 2 (LP2). Each decoding amplification reaction can result in the production of signal from labeling probe 1 and labeling probe 2. The ratio of labeling probe 1 to labeling probe 2 in any given decoding amplification reaction can provide a measure of the difference in quantity for a given target polynucleotide between the two samples. In the present embodiment, the first decoding amplification reaction allows for a quantification of target polynucleotide X between the first sample and the second sample based on the ratio of signal from labeling probe 1 verses labeling probe 2. The second decoding amplification reaction allows for a quantification of target polynucleotide Y between the first sample and the second sample based on the ratio of signal from labeling probe 1 verses labeling probe 2. The third decoding amplification reaction allows for a quantification of target polynucleotide Z between the first sample and the second sample based on the ratio of signal from labeling probe 1 verses labeling probe 2. The fourth decoding amplification reaction allows for a quantification of target polynucleotide N between the first sample and the second sample based on the ratio of signal from labeling probe 1 verses labeling probe 2.

In some embodiments, one or more target polynucleotides are subjected to an encoding ligation reaction and a decoding amplification reaction, either directly or via an intermediate, such as a cDNA target generated from an mRNA by reverse transcription. In some embodiments, the initial target polynucleotide comprises mRNA and a reverse transcription reaction can be performed to generate at least one cDNA, followed by at least one encoding ligation reaction and at least one decoding amplification reaction. In some embodiments, DNA ligation probes hybridize to target RNA, and an RNA dependent DNA ligase is employed in a ligation reaction, followed by a decoding amplification reaction. The ligation products and amplification products can be detected (or quantified) using labeling probes.

Comparison of Expressed Genes in a Single Sample with an Encoding Ligation Reaction The addressable primer portions of the ligation probes of the encoding reaction, and the address primers of the decoding amplification reaction, can provide for detection of the presence or absence, or quantification, of a plurality of target polynucleotides. It will be appreciated that the teachings of the preceding exemplary embodiments can also be applied in the context of these non-limiting foregoing embodiments wherein, comparisons of at least one expressed gene are performed with an encoding ligation reaction. The addressable primer portions of the present teachings can provide for increased detection of up to a large number of target polynucleotides, while minimizing unique reagent compositions, allowing for the redundant use of a battery of address primer sets as will become more clear in the following illustrative embodiments.

Figure 4A:
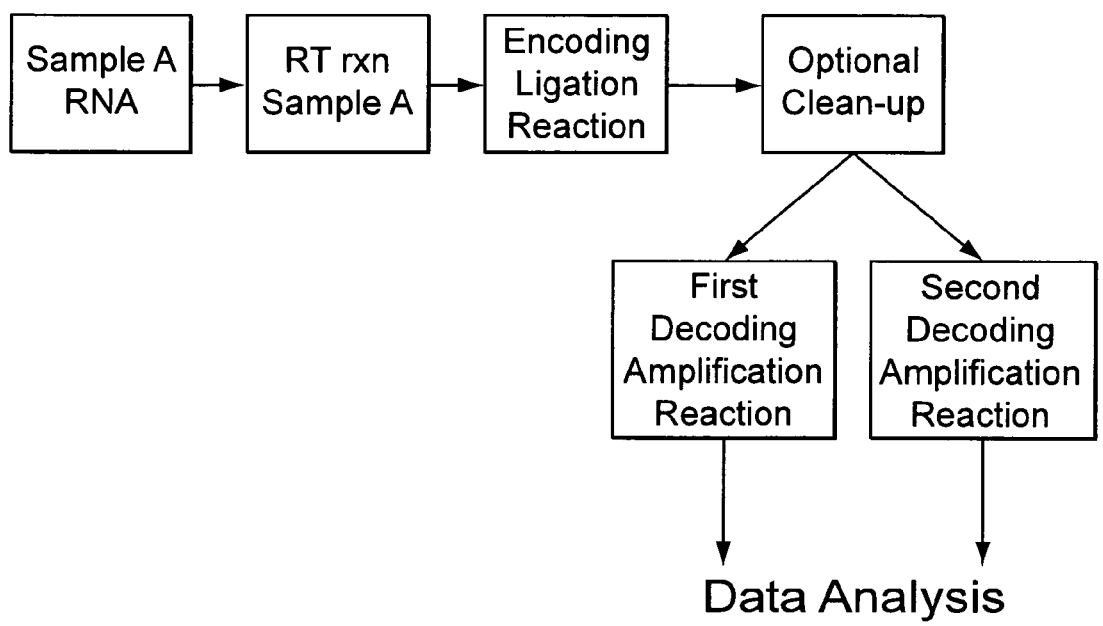
FIG. 4 depicts a flowchart and certain compositions and reaction interactions in accordance with some embodiments of the present teachings.

An illustrative schematic of the present teachings is shown in FIG. 4A, wherein a single sample of expressed genes can be reverse transcribed, and an encoding reaction performed thereon. Following an optional clean-up of unincorporated reaction components, the encoding reaction products can be split into at least two decoding reactions.

Figure 4B:
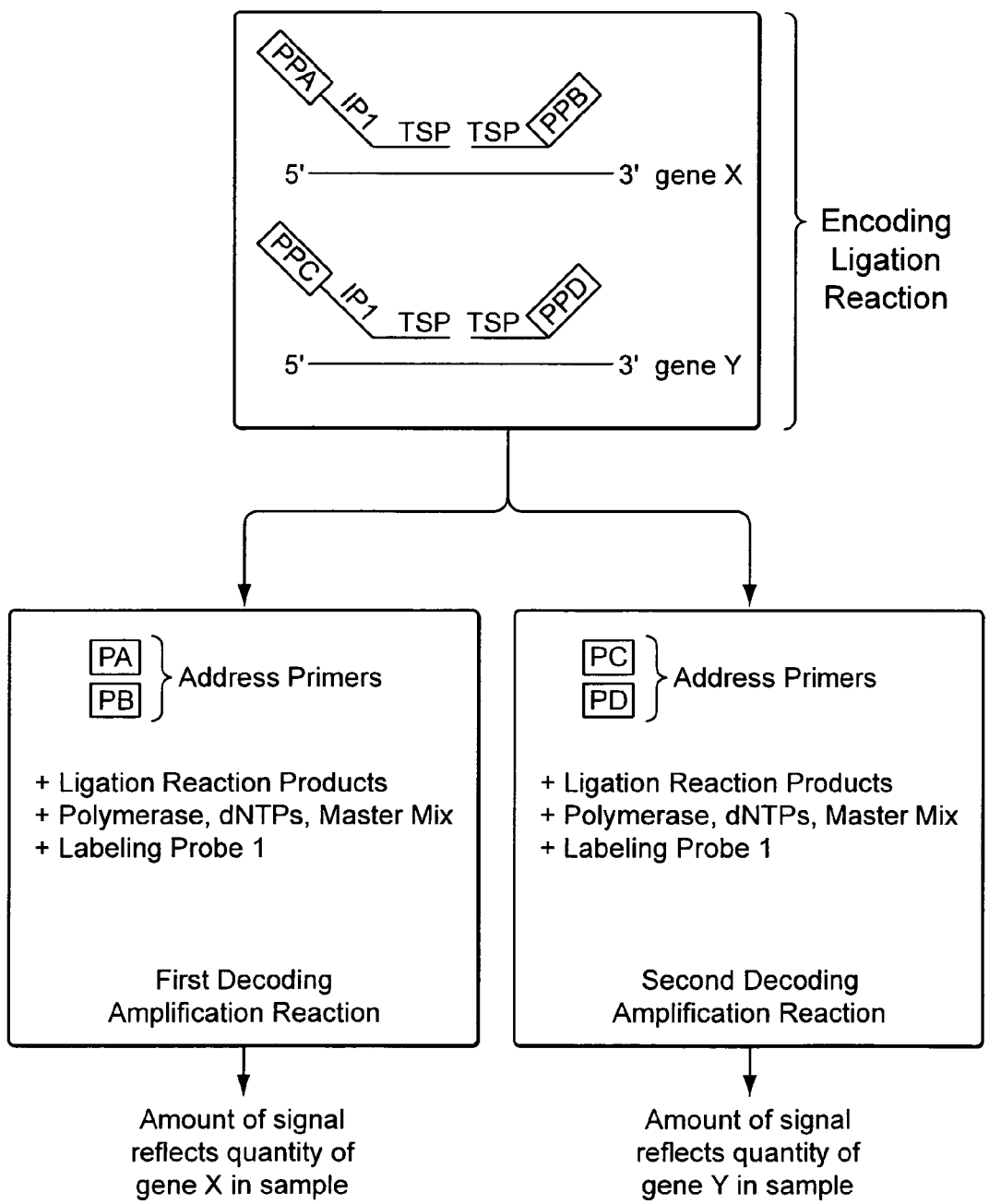

As shown in FIG. 4B, a given gene of interest X can be queried in an encoding ligation reaction with a first probe comprising a 5' addressable primer portion A and an identifying portion 1, and a second probe comprising a 3' addressable primer portion B. Also in the first encoding ligation reaction, a given gene of interest Y can be queried with a first probe comprising a 5' addressable primer portion C and an identifying portion 1, and a second probe comprising a 3' addressable primer portion D. In such a scheme, the identity of given target polynucleotide (here, a given expressed gene) can be encoded with the addressable primer portions.

After the encoding ligation reaction is performed, the reaction products can be split into at least two decoding amplification reactions. The decoding amplification reactions can comprise a first decoding amplification reaction comprising an address primer A, an address primer B, and a labeling probe 1, and a second decoding amplification reaction comprising an address primer C, address primer D, and the labeling probe 1. Each decoding amplification reaction can result in the production of signal from labeling probe 1. The quantity of signal of labeling probe 1 in any given decoding amplification reaction can provide a measure of the difference in expression level for different expressed genes in a given sample, as conferred by the given address primers in a given decoding reaction. In the present embodiment, the first decoding amplification reaction allows for a quantification of gene X in the sample based on the quantity of signal from labeling probe 1. The second decoding amplification reaction allows for a quantification of gene Y in the sample based on the quantity of signal from labeling probe 1. In such a scheme, the identity of given expressed gene can be encoded with the addressable primer portions, and the ability to detect and quantify expressed genes in a sample encoded with the same identifying portion and assessed by the signal derived for a single labeling probe.

Comparison of Expressed Proteins in a Single Sample with an Encoding Ligation Reaction The addressable primer portions of the ligation probes of the encoding reaction, and the address primers of the decoding amplification reaction, can provide for detection of the presence or absence, or quantification, of a plurality of target proteins. The addressable primer portions of the present teachings can provide for increased detection of up to a large number of target proteins, while minimizing unique reagent compositions, allowing for the redundant use of a battery of address primer sets as will become more clear in the following illustrative embodiments.

Figure 4C:
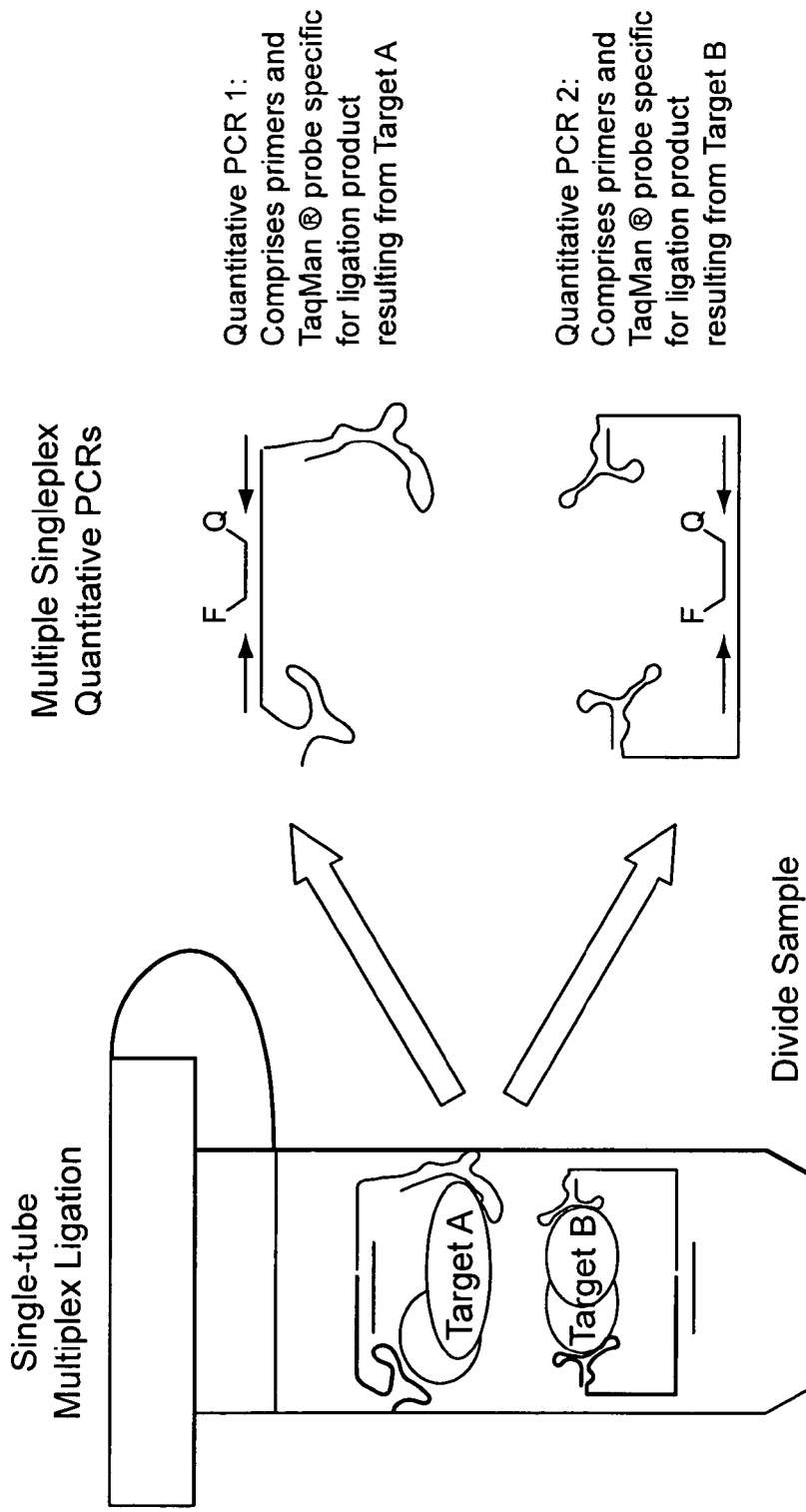

An illustrative schematic of the present teachings is shown in FIG. 4C, wherein a target A protein and a target B protein are detected in an encoding ligation proximity reaction. Following an optional clean-up of unincorporated reaction components, the encoding reaction products can be split into at least two decoding reactions. Descriptions of proximity ligation assays can be found for example in Landegren et al., Journal of Molecular Recognition, 2004:17:194-197, Landegren and Fredriksson Published P.C.T. Application WO/01/61037A1, Fredriksson et al, Nature Biotech, 2002, 20:473-477, Gullberg et al., PNAS, 101:22:8420-8424. Basically, a proximity ligation assay provides the ability to detect proteins by using an amplification reaction such as PCR. By binding binders (e.g.—antibodies, and/or aptamers) specifically to a protein of interest, nucleic acids that are attached to the binders can be ligated together on a splint as a result of their proximity, thereby allowing for the generation of an amplifiable polynucleotide. Signal resulting from the amplification of the polynucleotide in a real-time, or end-point PCR, can provide a measure of the level of the protein in the sample. By incorporating addressable primer portions, and potentially identifying portions, into the nucleic acids that are attached to the binders, the ligation encoding reaction described within the present teachings can be applied to protein analysis.

Proximity ligation is based on the creation of a known amplicon to quantify protein detection. In some embodiments of the present teachings, dUTP and uracil N-glycosylase are present in the ligation mix and/or PCR mix, thereby allowing the researcher to removing any contaminating nucleic acids from previous reactions. Such approaches applied in nucleic acids analyses can be found, for example, in U.S. Pat. No. 5,035,996, U.S. Pat. No. 5,945,313, and U.S. Pat. No. 6,518,026, to Hartley et al.

In some embodiments of the present teachings, the use of a passive reference dye in the decoding amplification reaction can be performed, which can provided improvements in the precision of the real-time PCR by helping to normalize out non-chemical effects such as pipetting error and bubbles.

In some embodiments, a kinase, or a flap endonuclease, can be included in the ligation encoding reaction to allow for the addition of a phosphate group to the appropriate 5' end. Additional teachings regarding various enzymes that can be present in a ligation mixture to provide phosphorylation, and/or uracil-mediated decontamination, can be found in U.S. Provisional Application 60/584,682 to Andersen et al.

An example of comparing expressed proteins in a single sample with an encoding ligation reaction is as follows:

Ligation Probe Oligonucleotides:

Target A

Thrombin Left (SEQ ID NO:1)
5' <u>CAGTCCGTGGTAGGGCAGGTTGGGGTGACT</u>AGCACAAAAACGGTTCGA
CATAGTAGTTCTAGTATA*CGAGT*3'

Thrombin Right (SEQ ID NO:2)
5'p*CACATTGCACTCT***AAGGAAGGGTACTTGTGCT*GTGACTACTGGTTGG

TGAGGTTGGGTAGTCACAAA*3'

Thrombin Connector (Splint)

5' AAA GAGTGCAATGTGACTCGTATACTA TTT (SEQ ID NO:3)

Target B (Homodimer)
PDGF Left (SEQ ID NO:4)
5'*TACTCAGGGCACTGCAAGCAATTGTGGTCCCAATGGGCTGAGTA***AGCA

CAAACTTCCAACCGT** TATTGTACTTGAATCA*GCACT*

PDGF Right (SEQ ID NO:5)
5'p*CAGATTCCAGTCT*TAGGTTCGGAGATGGTGCT*TACTCAGGGCACTGC

AAGCAATTGTGGTCCCAATGGGCTGAGTAT*3'

PDGF Connector (Splint)

5' AAA GACTGGAATCTGAGTGCTTGATTC TTT (SEQ ID NO:6)

p=phosphate
Underline=aptamer sequence
Bold=primer binding sequences
Italic=TaqMan probe binding sequence PCR Amplification Oligonucleotides:

(SEQ ID NO:7)
Universal Forward 5' GGAGCACAAAAACGGTTCGAC
A
(SEQ ID NO:8)
Universal Reverse 5' GGAGCACAAGTACCCTTCCTT
B
(SEQ ID NO:9)
Universal Labeling 5' FAM-ACGAGTCACATTGCAC-MGB-NFQ
Probe 1
(SEQ ID NO:10)
Universal Forward 5' GGAGCACAAACTTCCAACCGT
C
(SEQ ID NO:11)
Universal Reverse 5' GGAGCACCATCTCCGAACCTA
D
(SEQ ID NO:12)
Universal Labeling 5' VIC-AGCACTCAGATTCCAG-MGB-NFQ
Probe 2

Experimental Protocol:
 1) Prepare 10 ul ligation reaction by combining:
 Sample containing target protein
 1% BSA
 1× Ligase Buffer (20 mM Tris pH 7.6, 20 mM KCl, 0.1% Triton x-100, 5 mM MgCl2, 1 mM NAD)
 2 U/ul DNA ligase
 20 pM each of Thrombin Right, Thrombin Left, PDGF Right, PDGF Left
 400 nM each of Thrombin connector and PDGF connector Optional Components:
 0.01 U/ul UNG
 0.1 U/ul Polynucleotide Kinase and 1 mM dATP Researcher can also include positive and negative control reactions.
 2) Incubate 5 minutes at 25C, then 99C for 20 minutes
 3) Add 1 ul of ligation reaction to PCR#1 (20 ul) in an optical 96-well plate containing:
 1× Universal PCR Master Mix (Applied Biosystems)
 900 nM each Universal forward primer A and reverse primer B
 200 nM universal labeling probe 1

Researcher may also include positive and negative control reactions.
 4) Add 1 ul of ligation reaction to PCR#2 (20 ul) in an optical 96-well plate containing:
 1× Universal PCR Master Mix (AB)
 900 nM each universal forward primer C and reverse primer D
 200 nM universal labeling probe 2

Researcher may also include positive and negative control reactions.

Alternatively, in some embodiments, PCR #1 and #2 may be combined into a single reaction
 5) In a AB 7900 real-time thermal cycler perform the following program
 95C 10 min
 then 40 cycles of
 95C 15 sec
 60C 1 min
 6) Compare Ct values to control reactions to determine starting target copy numbers In some embodiments, the researcher can optionally perform delta-delta Ct analysis with other samples Multi-Sample Comparison of Expressed Proteins with a Ligation Encoding Reaction Some embodiments of the present teachings provide for comparison analyses of at least one given target protein between at least two samples. The addressable primer portions of the ligation probes of the encoding reaction, and the address primers of the decoding amplification reaction, can provide for detection of the presence or absence, or quantification, of at least one target protein between two samples. The addressable primer portions of the present teachings can provide for increased detection of up to a large number target proteins, while minimizing unique reagent compositions, allowing for the redundant use of a battery of address primer sets as will become more clear in the following illustrative embodiments.

Figure 4D:
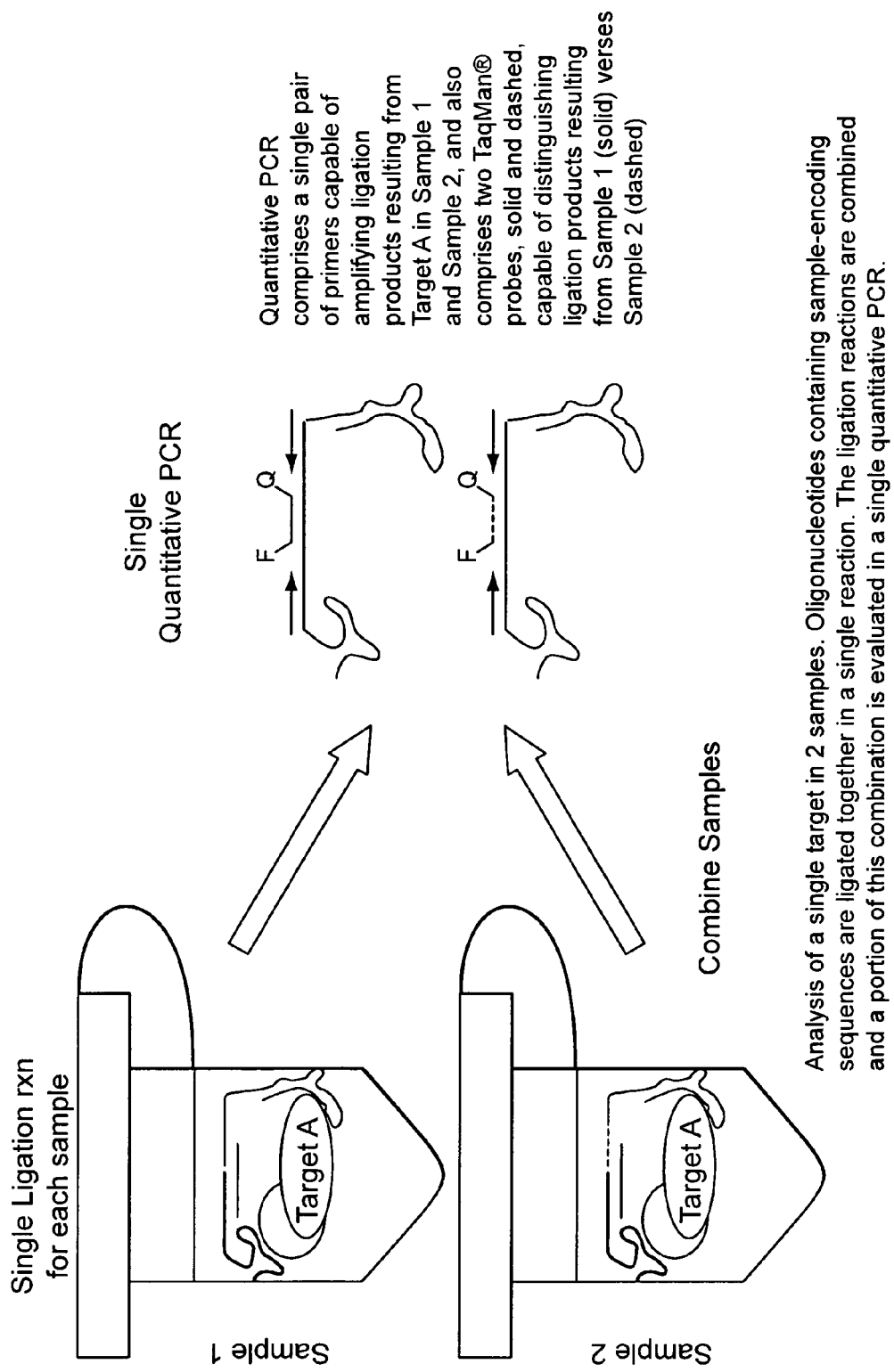

In some embodiments of the present teachings, the encoding ligation reaction can be performed in parallel on at least two samples (see for example FIG. 4D), wherein a target A protein from two different samples is encoded in two proximity ligation reactions and decoded in a single PCR amplification reaction. Descriptions of proximity ligation assays can be found for example in Landegren et al., Journal of Molecular Recognition, 2004:17:194-197, Landegren and Fredriksson Published P.C.T. Application WO/01/61037A1, Fredriksson et al, Nature Biotech, 2002, 20:473-477, Gullberg et al., PNAS, 101:22:8420-8424.

An Example is as follows:

Analysis of a Single Target in 2 Samples.

Ligation Oligonucleotides:

Sample 1

Thrombin Left-1

(SEQ ID NO: 13)
5' <u>CAGTCCGTGGTAGGGCAGGTTGGGGTGACT</u>AGCACAAAAACGGTTCGA
CATAGTAGTTCTAGTATA*CGAGT*

Thrombin Right-1

(SEQ ID NO: 14)
5' p*CACATTGCACTCT*AAGGAAGGGTACTTGTGCT<u>GTGACTACTGGTTGG</u>
<u>TGAGGTTGGGTAGTCACAAA</u>

Thrombin Connector-1 (Slint)

(SEQ ID NO: 15)
5' AAA GAGTGCAATGTGACTCGTATACTA TTT

Sample 2

Thrombin Left-2

(SEQ ID NO: 16)
5' <u>CAGTCCGTGGTAGGGCAGGTTGGGGTGACT</u>AGCACAAAAACGGTTCGA
CATAGTAGTTCTAGTATA*CGACT*

Thrombin Right-2

(SEQ ID NO: 17)
5' p*CAGATTCCAGTCT*AAGGAAGGGTACTTGTGCT<u>GTGACTACTGGTTGG</u>
<u>TGAGGTTGGGTAGTCACAAA</u>

Thrombin Connector-2

(SEQ ID NO: 18)
5' AAA GACTGGAATCTGAGTGCTATACTA TTT (splint)

p=phosphate
Underline=aptamer sequence
Bold=primer binding sequences
Italic=TaqMan probe binding sequence Amplification Oligonucleotides:

(SEQ ID NO: 19)
Universal Forward 5' GGAGCACAAAAACGGTTCGAC
Primer A (SEQ ID NO: 20)
Universal Reverse 5' GGAGCACAAGTACCCTTCCTT
Primer B (SEQ ID NO: 21)
Universal Labeling 5' FAM-ACGAGTCACATTGCAC-MGB-NFQ
probe sample 1

(SEQ ID NO: 22)
Universal labeling 5' VIC-AGCACTCAGATTCCAG-MGB-NFQ
probe sample 2

Experimental Protocol:
(1) Prepare a 10 ul Ligation reaction for sample 1 by combining:
Sample containing target protein
1% BSA
1× Ligase Buffer (20 mM Tris pH 7.6, 20 mM KCl, 0.1% Triton x-100, 5 mM MgCl2, 1 mM NAD)
2 U/ul DNA ligase
20 pM each of Thrombin Right-1, Thrombin Left-1
400 nM of Thrombin connector-1

Optional Components:
0.01 U/ul UNG
0.1 U/ul Polynucleotide Kinase and 1 mM dATP

The researcher can include positive and negative control reactions.
(2) Prepare a 10 ul Ligation reaction for sample 2 by combining:
Sample containing target protein
1% BSA
1× Ligase Buffer (20 mM Tris pH 7.6, 20 mM KCl, 0.1% Triton x-100, 5 mM MgCl2, 1 mM NAD)
2 U/ul DNA ligase
20 pM each of Thrombin Right-2, Thrombin Left-2
400 nM of Thrombin connector-2

The researcher can include positive and negative control reactions.
(3) Incubate each reaction for 5 minutes at 25C, then 99C for 20 minutes
(4) Combine 5 ul from each ligation reaction and mix thoroughly
(5) Add 1 ul of mixed ligation reactions to a PCR (20 ul) in an optical 96-well plate containing:
1× Universal PCR Master Mix (Applied Biosystems)
900 nM each Universal forward primer A and reverse primer B
200 nM each Universal labeling probe sample 1 and Universal labeling probe sample 2

The researcher can include positive and negative control reactions
(6) In a AB 7900 real-time thermal cycler perform the following program
95C 10 min
then 40 cycles of
95C 15 sec
60C 1 min
(7) The researcher can compare Ct values from FAM and VIC probes to determine the difference in starting target copy number between the samples.

Optionally, the researcher can compare delta Rn values from FAM and VIC to determine the difference in starting target copy number between the samples.

Multi-Sample Comparison of Expressed Genes with a Ligation Encoding Reaction

Some embodiments of the present teachings provide for comparison analyses of at least one given expressed target polynucleotide between at least two samples. The addressable primer portions of the ligation probes of the encoding reaction, and the address primers of the decoding amplification reaction, can provide for detection of the presence or absence, or quantification, of at least one target polynucleotides between two samples. The addressable primer portions of the present teachings can provide for increased detection of up to a large number target polynucleotides, while minimizing unique reagent compositions, allowing for the redundant use of a battery of address primer sets as will become more clear in the following illustrative embodiments.

Figure 5:
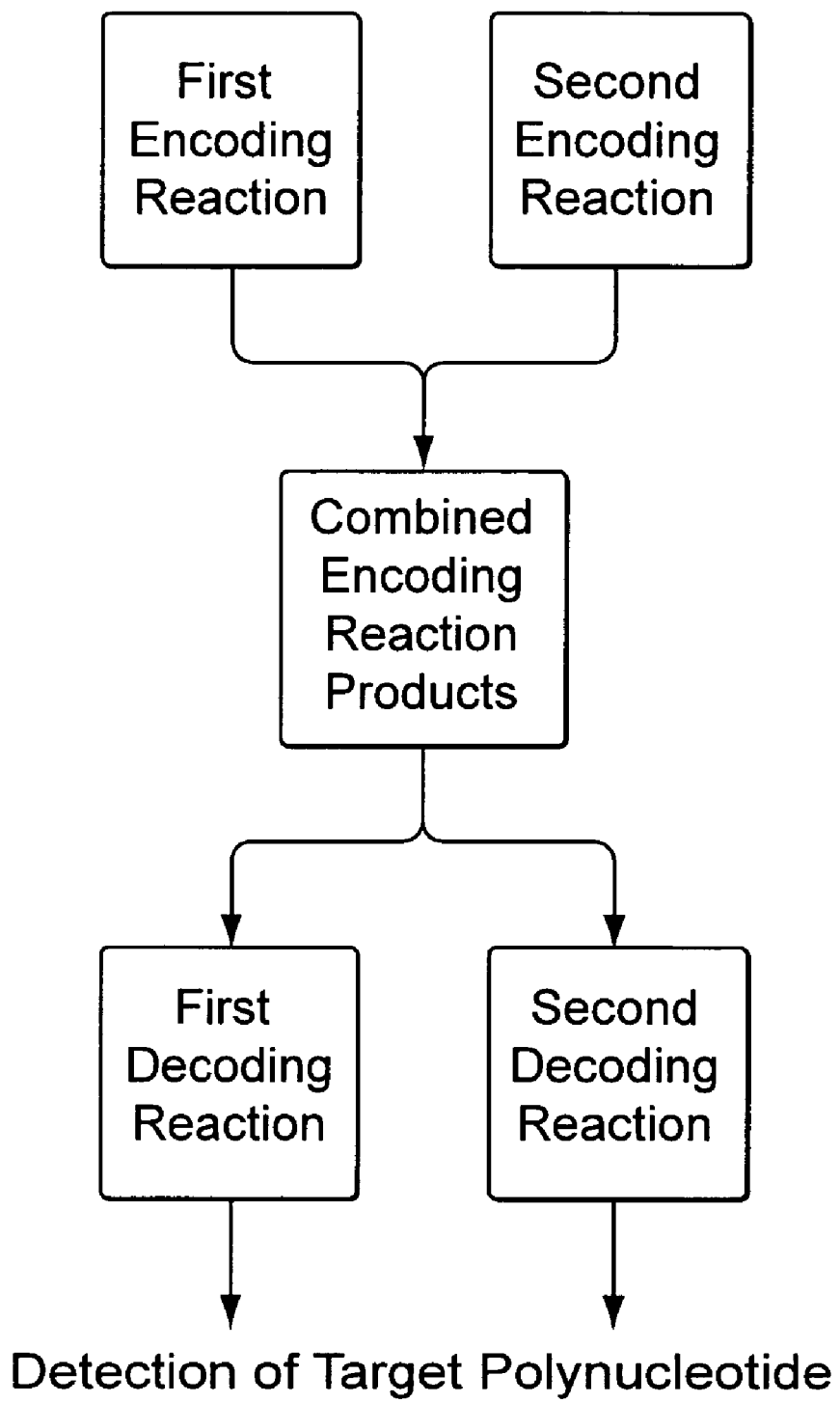
FIG. 5 depicts a flowchart in accordance with some embodiments of the present teachings.

In some embodiments of the present teachings, the encoding ligation reaction can be performed in parallel on at least two samples (see for example FIG. 5). For example, an mRNA sample, or cDNA sample produced therefrom, can be acquired from a first source. Further, an mRNA sample, or cDNA sample produced therefrom, can be acquired from a second source. An encoding reaction can then be performed on each of the two samples individually. The individually performed encoding reactions can then be combined together into a single mixture, and at least one decoding amplification reaction performed. The decoding reaction can allow for a comparison of the expression level of at least one target polynucleotide sequence between the two samples.

Figure 6A:
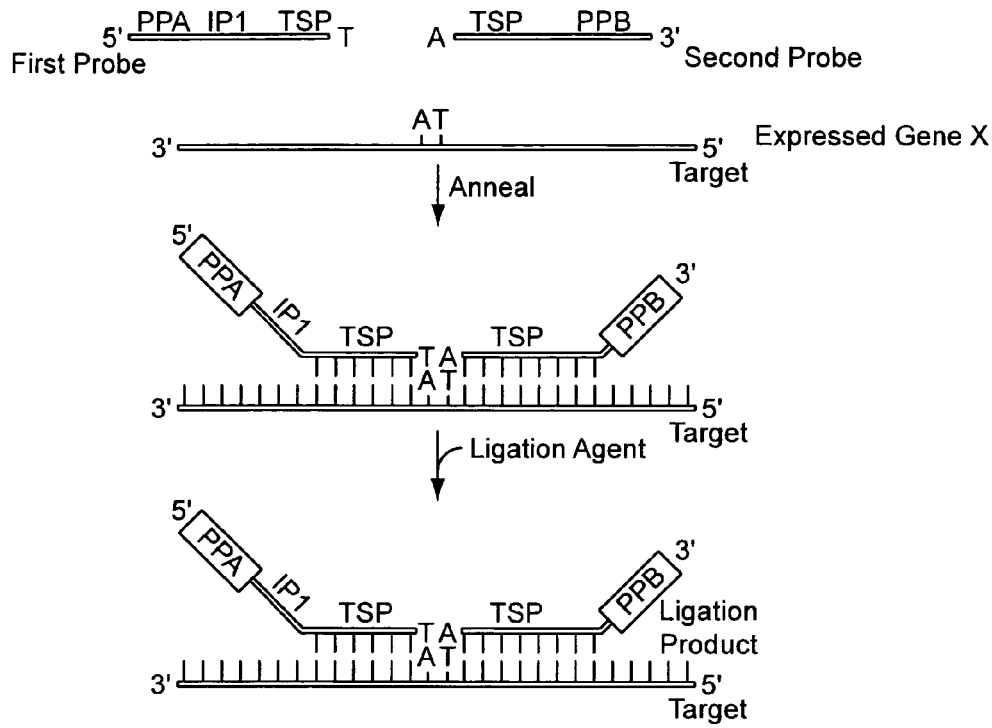
FIG. 6 depicts certain compositions and reaction interactions in accordance with some embodiments of the present teachings.
Figure 6A:
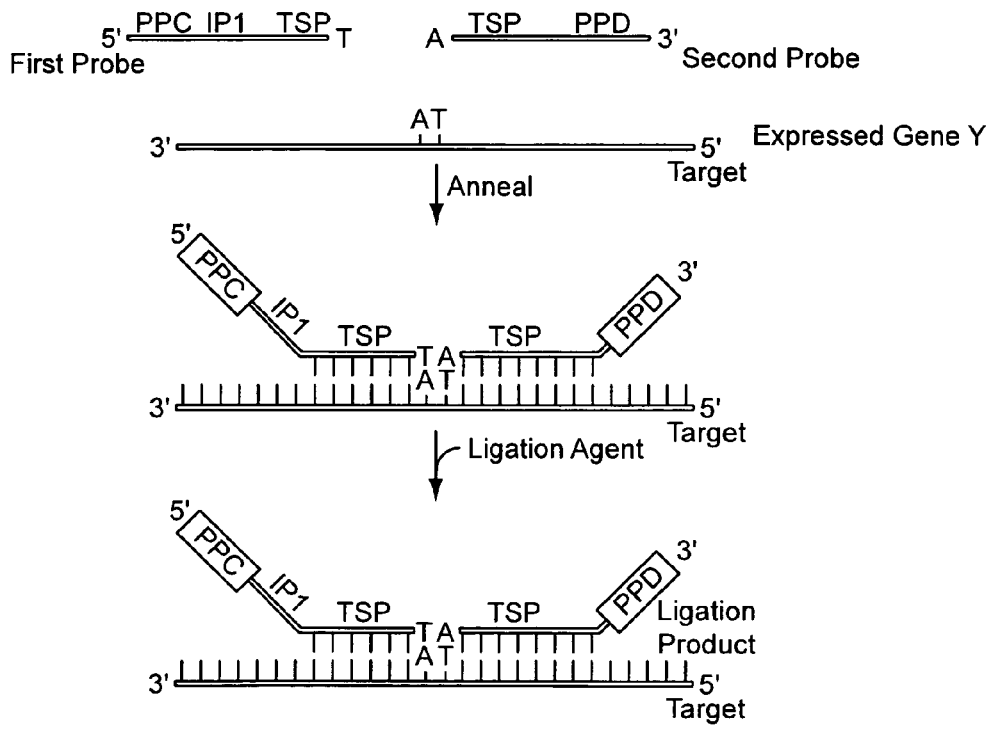

In one non-limiting embodiment depicted in FIG. 6A, a given gene of interest X (upper half of FIG. 6A) can be queried in a first encoding ligation reaction with a first probe comprising a 5' addressable primer portion A (PPA), an identifying portion 1 (IP1), and a target specific portion (TSP), and a second probe comprising a target specific portion (TSP) and a 3' addressable primer portion B (PPB). Also in the first encoding ligation reaction, a given gene of interest Y (lower half of FIG. 6A) can be queried with a first probe comprising a 5' addressable primer portion C (PPC), an identifying portion 1 (IP1), and a target specific portion (TSP), and a second probe comprising a target specific portion (TSP) and a 3' addressable primer portion D (PPD).

Figure 6B:
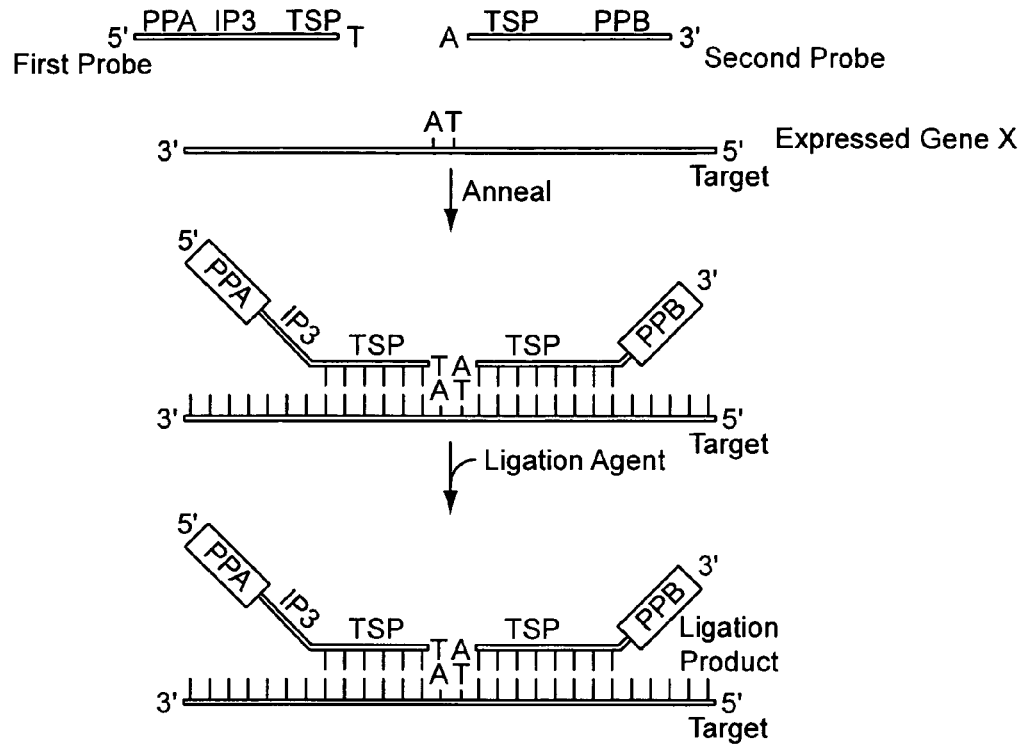
Figure 6B:
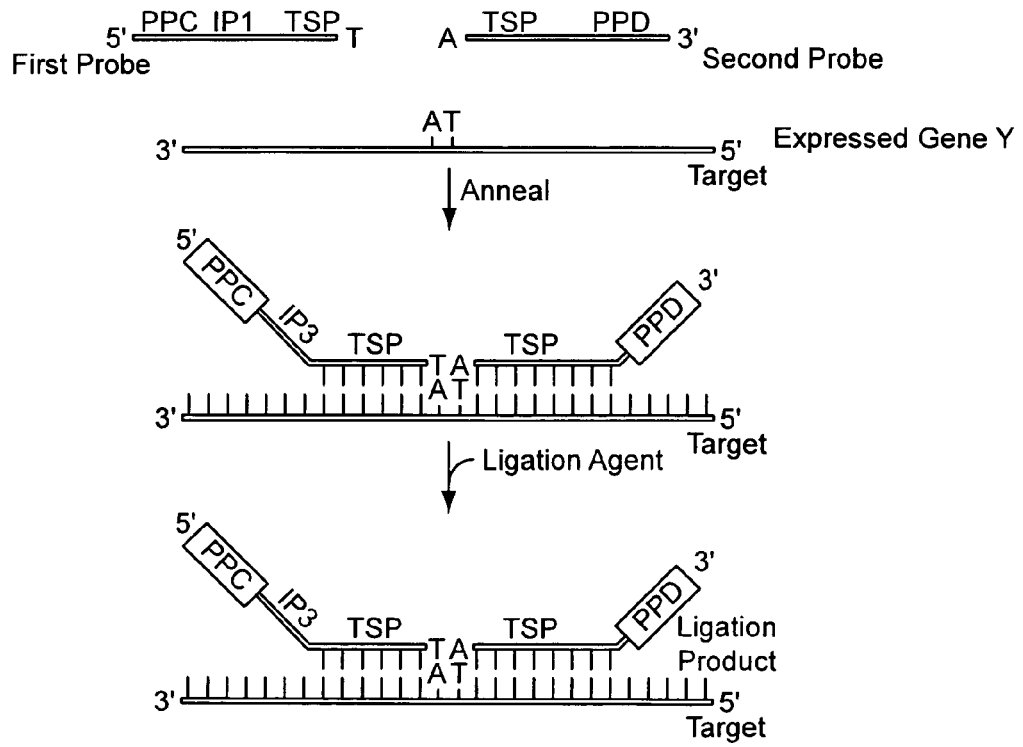

Further, in a second encoding ligation reaction (see for example FIG. 6B), gene of interest X (upper half of FIG. 6B) can be queried with a first probe comprising a 5' addressable primer portion A (PPA) and an identifying portion 3 (IP3), and a second probe comprising a target specific portion (TSP) and a 3' addressable primer portion B (PPB). Gene of interest Y can be queried with a first probe comprising a 5' addressable primer portion C (PPC) and an identifying portion 3 (IP3), and a second probe comprising a target specific portion (TSP) and a 3' addressable primer portion D (PPD).

In such a scheme, the sample of origin for a given expressed gene species can be encoded with the identifying portion, and the identity of a given expressed gene species encoded with the addressable primer portions.

Figure 6C:
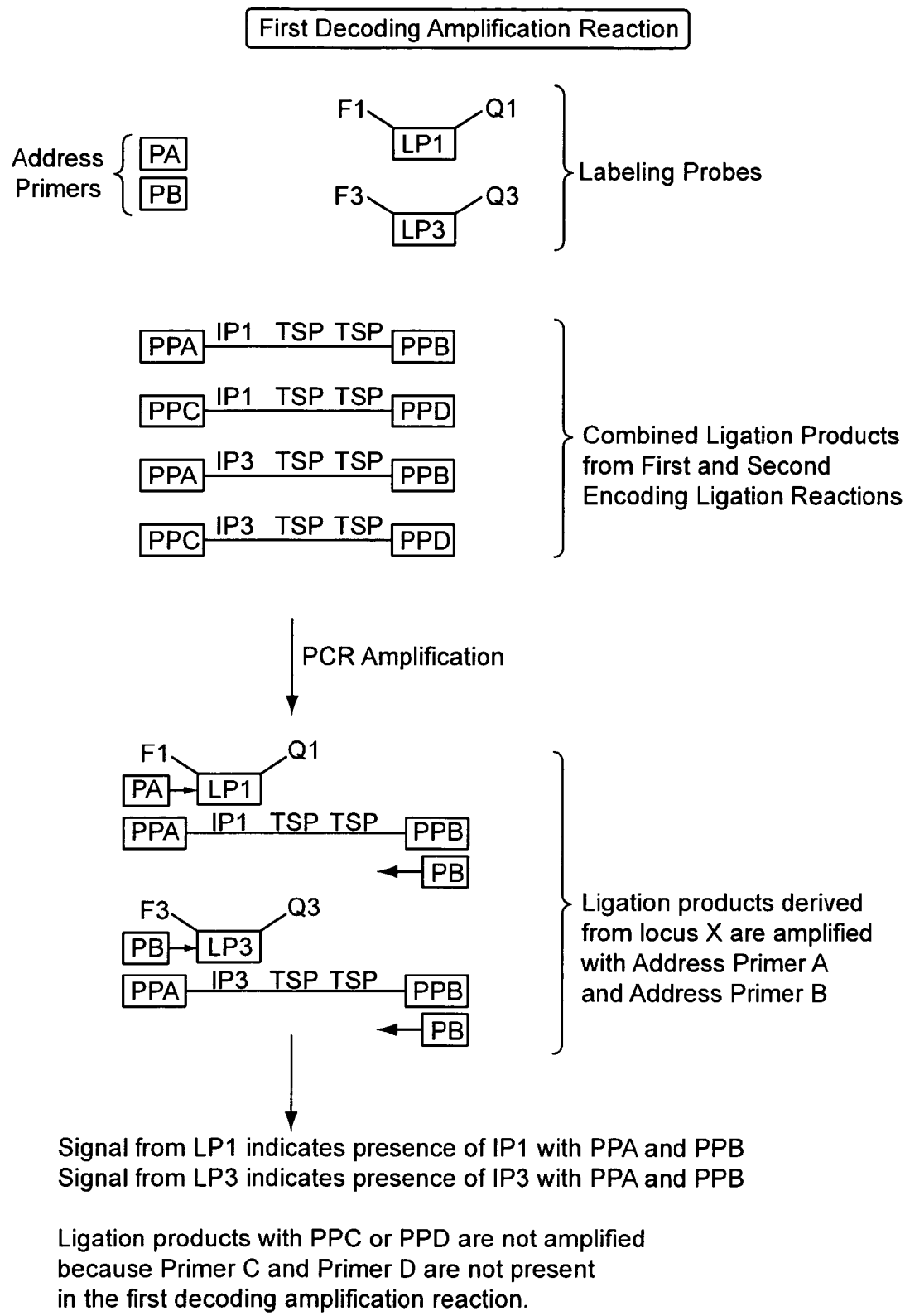
Figure 6D:
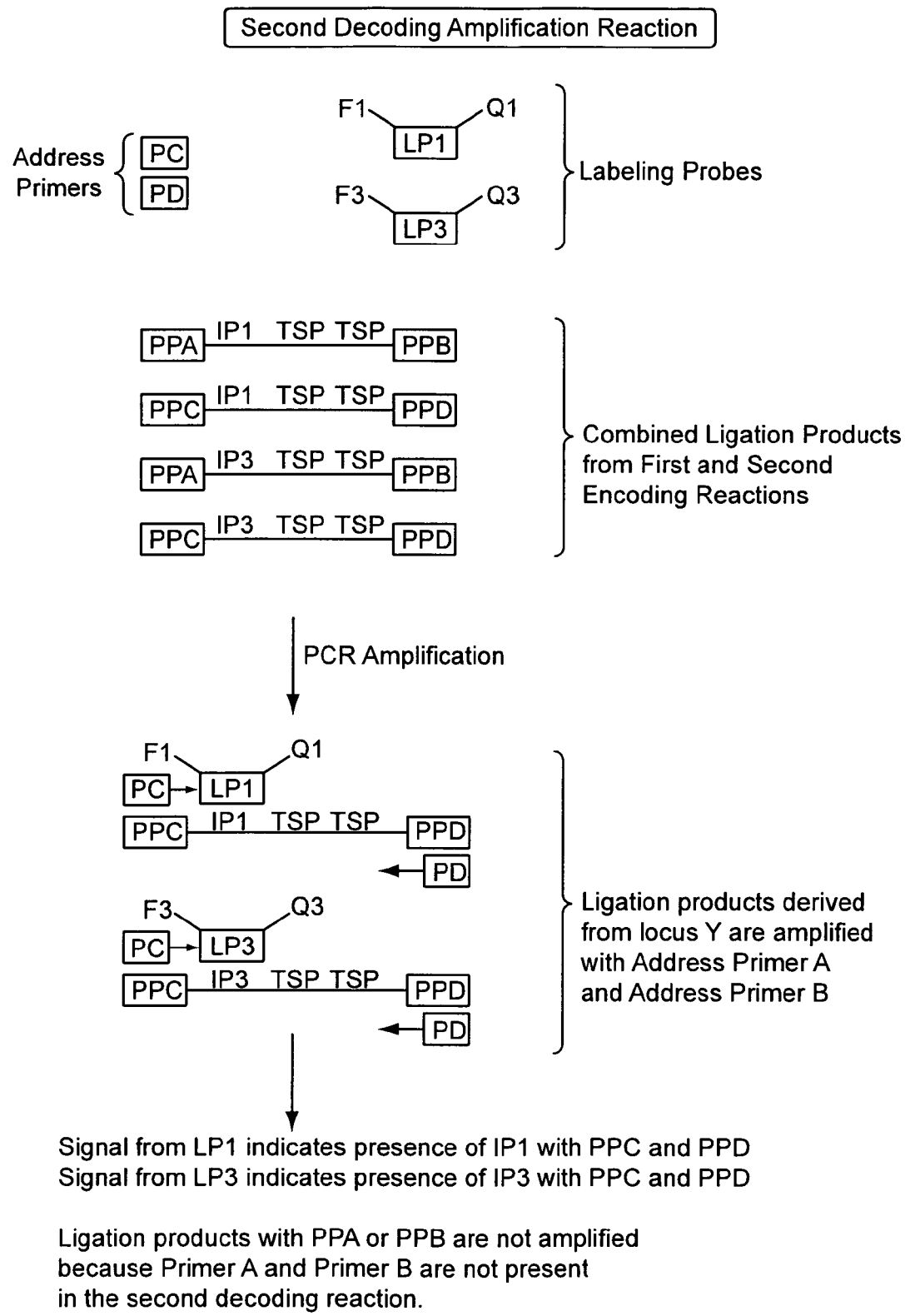

After the first and second encoding ligation reactions are performed, the reaction products can be combined together. The combined encoding reaction products can then be split into at least two decoding amplification reactions. The decoding amplification reactions can comprise a first decoding amplification reaction (FIG. 6C) comprising an address primer A, an address primer B, labeling probe 1, and labeling probe 3, and a second decoding amplification reaction (FIG. 6D) comprising an address primer C, address primer D, labeling probe 1, and labeling probe 3. Each decoding amplification reaction can result in the production of signal from labeling probe 1 and labeling probe 3. The ratio of signal from labeling probe 1 to labeling probe 3 in any given decoding amplification reaction can provide a measure of the difference in expression level for a given gene between the two samples. In the present embodiment, the first decoding amplification reaction allows for a quantification of gene X between the first sample and the second sample based on the ratio of signal from labeling probe 1 verses labeling probe 3. The second decoding amplification reaction allows for a quantification of gene Y between the first sample and the second sample based on the ratio of signal from labeling probe 1 verses labeling probe 3.

Multi-Sample Comparison of Expressed Genes from Pooled Samples with a Ligation Encoding Reaction Some embodiments of the present teachings provide for comparison analyses of at least one given expressed target polynucleotide between at least two samples, wherein at least one of the at least two samples is pooled from more than one source. The addressable primer portions of the ligation probes of the encoding reaction, and the address primers of the decoding amplification reaction, can provide for detection of the presence or absence, or quantification, of at least one target polynucleotide between two different samples. The addressable primer portions and the battery of corresponding address primers of the present teachings can provide for increased detection of up to a large number of target polynucleotides, while minimizing unique reagent compositions, allowing for the redundant use of a battery of address primer sets as will become more clear in the following illustrative embodiments.

Figure 7:
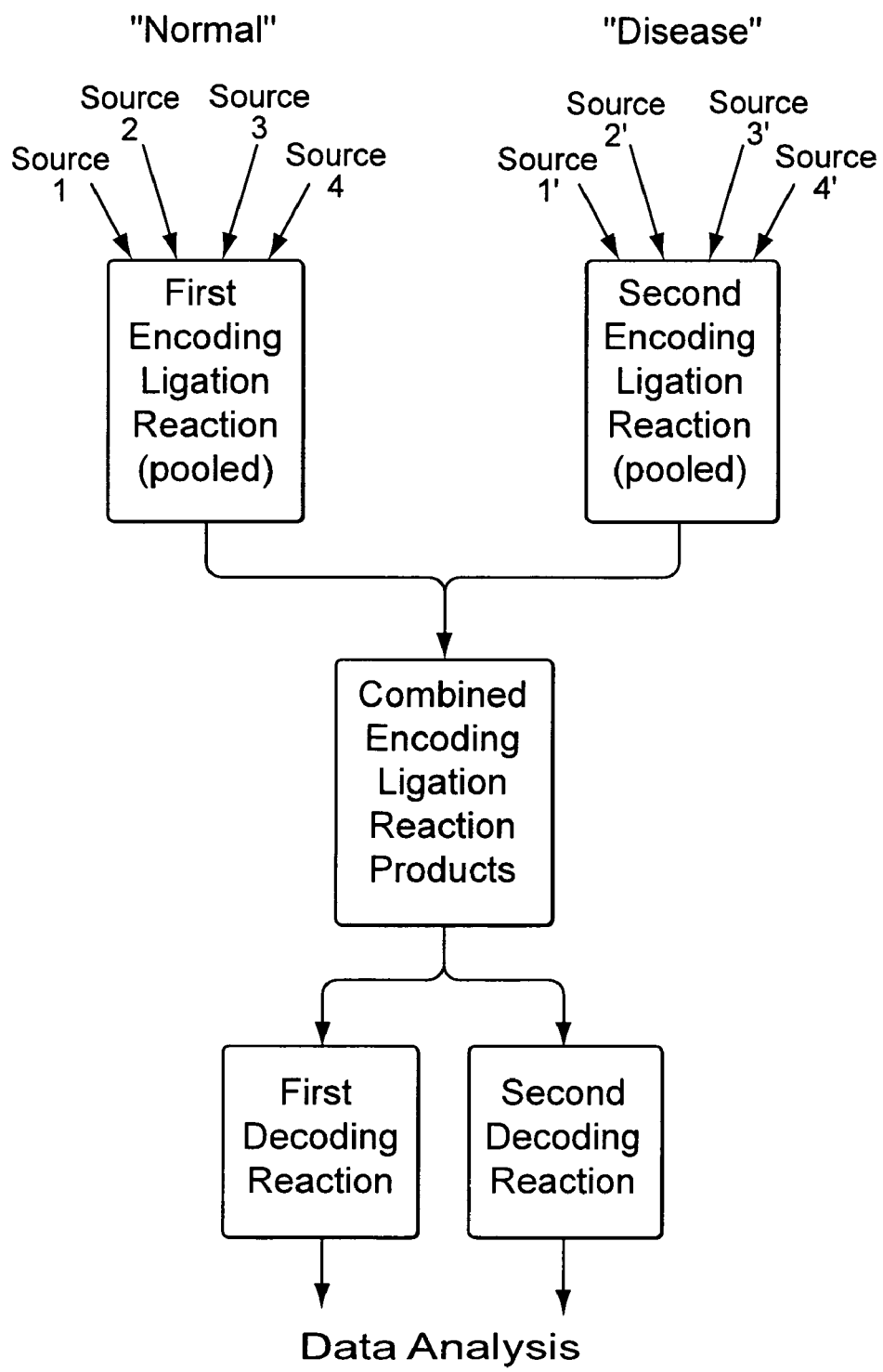
FIG. 7 depicts a flowchart in accordance with some embodiments of the present teachings.

In some embodiments of the present teachings, the encoding ligation reaction can be performed in parallel on at least two samples, wherein at least one of the two samples is pooled from at least two sources (see FIG. 7 schematic, for example). For example, an mRNA sample, or cDNA sample produced therefrom, can be acquired from at least two first sources. Further, an mRNA sample, or cDNA sample produced therefrom, can be acquired from at least two second sources. An encoding reaction can then be performed on each of the two pooled samples individually. The individually performed encoding reactions can then be combined together into a single mixture, and at least one decoding amplification reaction performed. The decoding reaction can allow for a comparison of the expression level of at least one target polynucleotide sequence between the two pooled samples.

For example (in a fashion analogous to that depicted in FIGS. 6A and 6B for non-pooled samples), a given gene of interest X can be queried in a first encoding ligation reaction with a first probe comprising a 5' addressable primer portion A, an identifying portion 1, and a target specific portion, and a second probe comprising a target specific portion and a 3' addressable primer portion B. Also in the first encoding ligation reaction, a given gene of interest Y can be queried with a first probe comprising a 5' addressable primer portion C, an identifying portion 1, and a target specific portion, and a second probe comprising a target specific portion and a 3' addressable primer portion D. The quantity of gene X and gene Y in the first encoding reaction is a result of at least two pooled samples; for example, at least two normal tissues are pooled together, and the quantity of gene X and gene Y in the first encoding reaction is a reflection of this pooling.

In a second encoding ligation reaction, gene of interest X can be queried with a first probe comprising a 5' addressable primer portion A, an identifying portion 3, and a target specific portion, and a second probe comprising a target specific portion and a 3' addressable primer portion B. Gene of interest Y can be queried with a first probe comprising a 5' addressable primer portion C, an identifying portion 3, and a target specific portion, and a second probe comprising a target specific portion and a 3' addressable primer portion D. The quantity of gene X and gene Y in the second encoding reaction is a result of at least two pooled samples; for example, at least two diseased tissues are pooled together, and the quantity of gene X and gene Y in the second encoding reaction is a reflection of this pooling. In such a scheme, the pooled sample identity for a given expressed gene species can be encoded with the identifying portion, and the identity of a given expressed gene species encoded with the addressable primer portions.

After the first and second encoding ligation reactions are performed, the products of the reactions can be combined together. The combined encoding reactions can then be split into at least two decoding amplification reactions (in a manner analogous to that depicted in FIG. 6C-6D for non-pooled samples). The decoding amplification reactions can comprise a first decoding amplification reaction comprising an address primer A, an address primer B, labeling probe 1, and labeling probe 3, and a second decoding amplification reaction comprising an address primer C, address primer D, labeling probe 1, and labeling probe 3. Each decoding amplification reaction can result in the production of signal from labeling probe 1 and labeling probe 3. The ratio of labeling probe 1 to labeling probe 3 in any given decoding amplification reaction can provide a measure of the difference in expression level for a given gene between two pooled samples. In the present embodiment, the first decoding amplification reaction allows for a quantification of gene X between the first pooled sample and the second pooled sample based on the ratio of signal from labeling probe 1 verses labeling probe 3. The second decoding amplification reaction allows for a quantification of gene Y between the first pooled sample and the second pooled sample based on the ratio of signal from labeling probe 1 verses labeling probe 3.

It will be appreciated that pooling need not involve multiple samples. For example, a single pooled sample can be analyzed according to the present teachings in a manner analogous to that depicted in FIGS. 4A and 4B for a single sample without pooling.

Comparison of Expressed Genes in a Single Sample with a PCR Encoding Reaction

In some embodiments, the encoding reaction can also comprise a PCR. In some embodiments comprising a PCR encoding reaction, the addressable primer portions are an extension of the 5' end of the target specific portion of PCR primers in the encoding reaction. The address primers of the decoding amplification reaction can provide for detection of the presence or absence, or quantification, of a plurality of target polynucleotides by amplifying products of the encoding PCR based on their addressable primer portions. It will be appreciated that the teachings of the preceding exemplary embodiments can also be applied in the context of these non-limiting foregoing embodiments, wherein comparisons of expressed genes are performed with a PCR encoding reaction. The addressable primer portions and the battery of corresponding address primers of the present teachings can provide for increased detection of up to a large number of target polynucleotides, while minimizing unique reagent compositions, allowing for the redundant use of a battery of address primer sets as will become more clear in the following illustrative embodiments.

Figure 8:
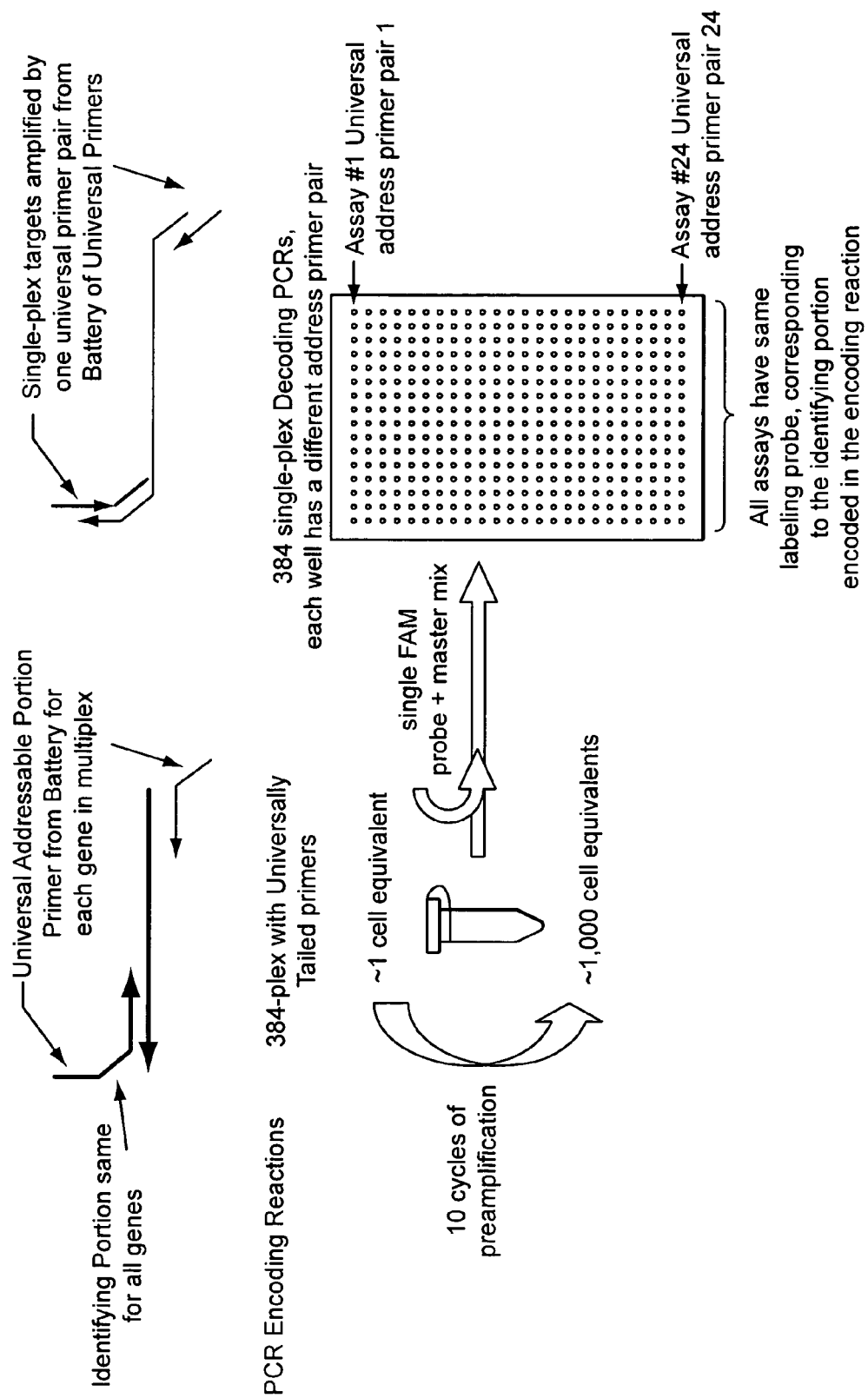
FIG. 8 depicts a flowchart in accordance with some embodiments of the present teachings.

For example, a given gene of interest X can be queried in a first encoding PCR with a first probe comprising a 5' addressable primer portion A, an identifying portion 1, and a target specific portion, and a second probe comprising a target specific portion and a 3' addressable primer portion B. Also in the first encoding PCR, a given gene of interest Y can be queried with a first probe comprising a 5' addressable primer portion C, an identifying portion 1, and a target specific portion, and a second probe comprising a target specific portion and a 3' addressable primer portion D. In such a scheme, as shown for example in FIG. 8, the identity of given expressed gene species can be encoded with the addressable primer portions. In FIG. 8, the addressable primer portion results in the use of a single address primer in the decoding reaction for a given gene of interest. (It will be appreciated that other embodiments are contemplated, for example as discussed infra with encoding ligation reactions wherein a first addressable primer portion and a second addressable primer portion were used in the first probe and second probe to query a given target gene, resulting in an two address primers in the eventual decoding reaction for that given gene. It is a general feature of the present teachings that embodiments comprising a single address primer, as well as a pair of address primers are contemplated for any given decoding reaction. In either case, the address primer or address primers in a given decoding reaction can be chosen from a universal battery of primers, thereby providing greater economies of scale in multiplexed embodiments, thereby for example minimizing unique primers and hence reducing overall cost).

After the encoding PCR is performed, the reaction products can be split into at least two decoding amplification reactions. The decoding amplification reactions can comprise a first decoding amplification reaction comprising an address primer A, and labeling probe 1, and a second decoding amplification reaction comprising an address primer B, and labeling probe 1. Each decoding amplification reaction can result in the production of signal from labeling probe 1. The quantity of signal of labeling probe 1 in any given decoding amplification reaction can provide a measure of the difference in expression level for different expressed genes in a given sample. In the present embodiment, the first decoding amplification reaction allows for a quantification of gene X in the sample based on the quantity of signal from labeling probe 1. The second decoding amplification reaction allows for a quantification of gene Y in the sample based on the quantity of signal from labeling probe 1. In such a scheme, as shown for example in FIG. 8, the identity of given expressed gene species can be encoded with the addressable primer portion(s), and the ability to detect and quantify expressed genes in a sample encoded with the same identifying portions and assessed by the signal derived for a single labeling probe.

Multi-Sample Comparison of Expressed Genes with a PCR Encoding Reaction

Some embodiments of the present teachings provide for comparison analyses of at least one given expressed target polynucleotide between at least two samples. The addressable primer portions of the PCR probes of the encoding reaction, and the address primers of the decoding amplification reaction, can provide for detection of the presence or absence, or quantification, of at least one target polynucleotide between two samples. The addressable primer portions and the battery of corresponding address primers of the present teachings can provide for increased detection of up to a large number of target polynucleotides while minimizing unique reagent compositions, allowing for the redundant use of a battery of address primer sets as will become more clear in the following illustrative embodiments.

Figure 9:
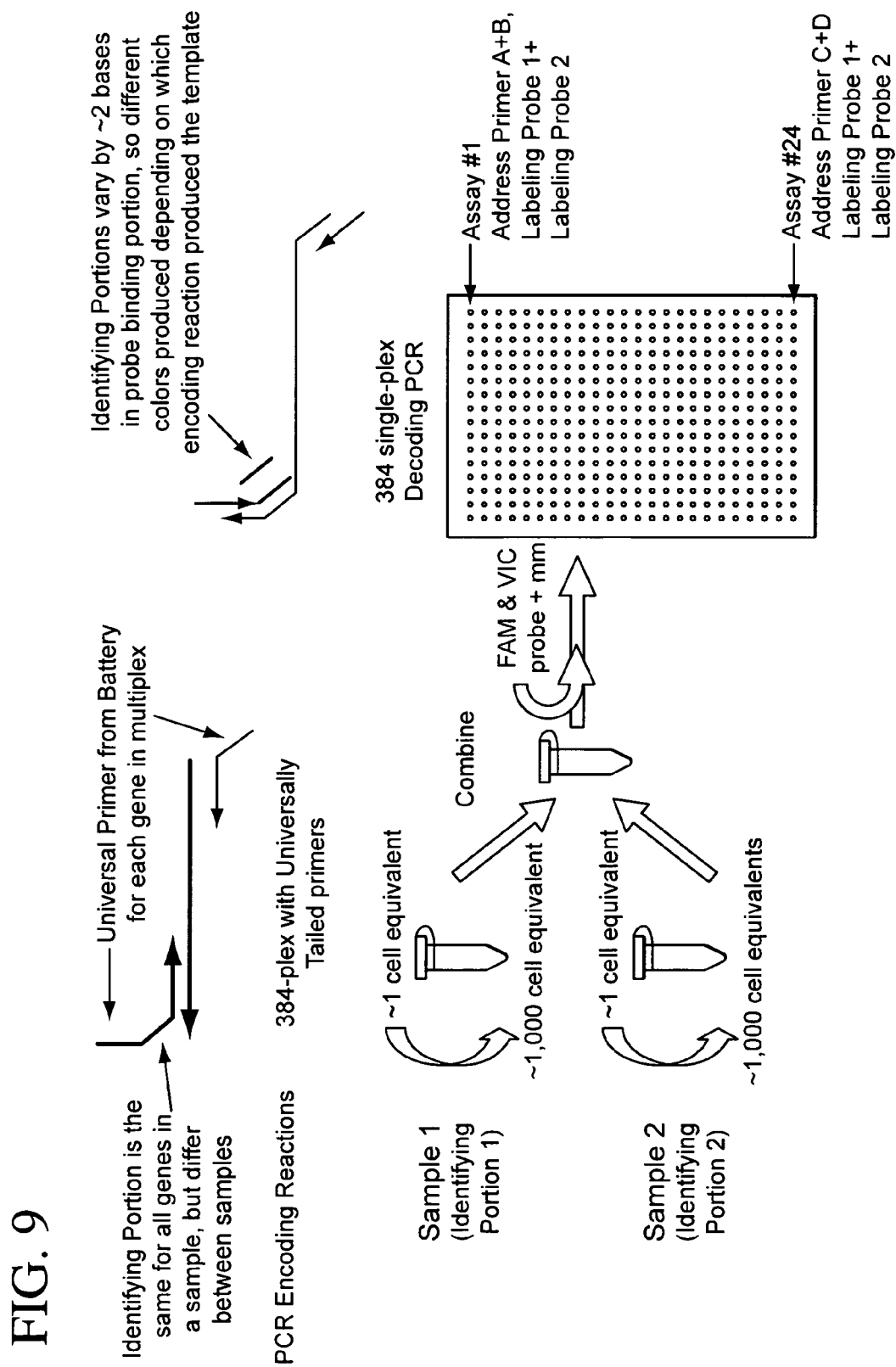
FIG. 9 depicts a flowchart in accordance with some embodiments of the present teachings.

In some embodiments of the present teachings, the encoding PCR can be performed in parallel on at least two samples (shown schematically in FIG. 9). For example, an mRNA sample, or cDNA sample produced therefrom, can be acquired from a first source. Further, an mRNA sample, or cDNA sample produced therefrom, can be acquired from a second source. An encoding reaction can then be performed on each of the two samples individually. The individually performed encoding reactions can then be combined together into a single mixture, and at least one decoding amplification performed. The decoding reaction can allow for a comparison of the expression level of at least one target polynucleotide sequence between the two samples.

For example, a given gene of interest X can be queried in a first encoding PCR with a first probe comprising a 5' addressable primer portion A, an identifying portion 1, and a target specific portion, and a second probe comprising a target specific portion and a 3' addressable primer portion B. Also in the first encoding PCR, a given gene of interest Y can be queried with a first probe comprising a 5' addressable primer portion C, a target specific portion, and an identifying portion 1, and a second probe comprising a target specific portion and a 3' addressable primer portion D.

In a second encoding PCR, gene of interest X can be queried with a first probe comprising a 5' addressable primer portion A, an identifying portion 2, a target specific portion, and a second probe comprising a target specific portion and a 3' addressable primer portion B. Gene of interest Y can be queried with a first probe comprising a 5' addressable primer portion C, an identifying portion 2, and a target specific portion, and a second probe comprising a target specific portion and a 3' addressable primer portion D. In such a scheme, as shown for example in FIG. 9, the sample of origin for a given expressed gene species can be encoded with the identifying portion, and the identity of a given expressed gene species encoded with the addressable primer portions.

After the first and second encoding PCRs are performed, the reaction products can be combined together. The combined encoding reactions can then be split into at least two decoding amplification reactions. The decoding amplification reactions can comprise a first decoding amplification reaction comprising an address primer A, an address primer B, labeling probe 1, and labeling probe 2 (shown in FIG. 9 as assay #1), and a second decoding amplification reaction comprising an address primer C, an address primer D, labeling probe 1, and labeling probe 2 (shown in FIG. 9 as assay #24). Each decoding amplification reaction can result in the production of signal from labeling probe 1 and labeling probe 2. The ratio of labeling probe 1 to labeling probe 2 in any given decoding amplification reaction can provide a measure of the difference in expression level for a given gene between two samples. In the present embodiment, the first decoding amplification reaction allows for a quantification of gene X between the first sample and the second sample based on the ratio of signal from labeling probe 1 verses labeling probe 2. The second decoding amplification reaction allows for a quantification of gene Y between the first sample and the second sample based on the ratio of signal from labeling probe 1 verses labeling probe 2.

Multi-Sample Comparison of Expressed Genes from Pooled Samples with a PCR Encoding Reaction Some embodiments of the present teachings provide for comparison analyses of at least one given expressed target polynucleotide between at least two samples, wherein at least one of the at least two samples is pooled from more than one source. The addressable primer portions of the probes of the encoding reaction, and the address primers of the decoding amplification reaction, can provide for detection of the presence or absence, or quantification, of at least one target polynucleotide between two samples. The addressable primer portions and the battery of corresponding address primers of the present teachings can provide for increased detection of target polynucleotides while minimizing unique reagent compositions, allowing for the redundant use of a battery of address primer sets as will become more clear in the following illustrative embodiments.

Figure 10:
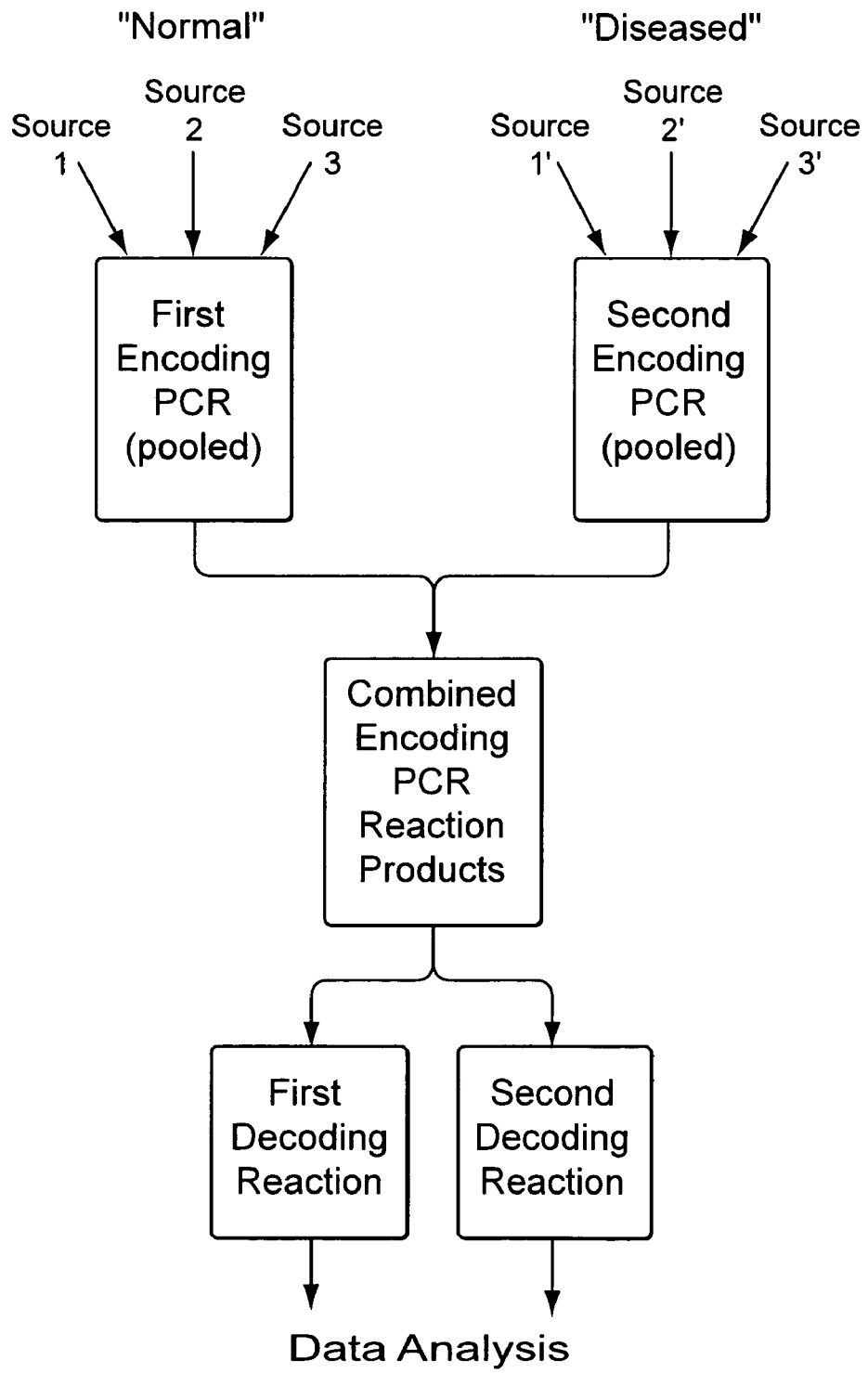
FIG. 10 depicts a flowchart in accordance with some embodiments of the present teachings.

In some embodiments of the present teachings, the encoding PCR can be performed in parallel on at least two samples, wherein at least one of the two samples is pooled from at least two sources. For example, an mRNA sample, or cDNA sample produced therefrom, can be acquired from at least two first sources. Further, an mRNA sample, or cDNA sample produced therefrom, can be acquired from at least two second sources. A PCR encoding reaction can then be performed on each of the two pooled samples individually. The individually performed PCR encoding reactions can then be combined together into a single mixture, and at least one decoding amplification performed. The decoding reaction can allow for a comparison of the expression level of at least one target polynucleotide sequence between the two pooled samples (for illustrative schematic, see FIG. 10 for example).

For example, (in a fashion roughly analogous to that depicted in FIG. 9 for non-pooled samples), a given gene of interest X can be queried in a first encoding PCR with a first probe comprising a 5' addressable primer portion A, an identifying portion 1, and a target specific portion, and a second probe comprising a target specific portion and a 3' addressable primer portion B. Also in the first encoding PCR, a given gene of interest Y can be queried with a first probe comprising a 5' addressable primer portion C, an identifying portion 1, and a target specific portion, and a second probe comprising a target specific portion and a 3' addressable primer portion D. The quantity of gene X and gene Y in the first encoding PCR is a result of at least two pooled samples; for example, at least two normal tissues are pooled together, and the quantity of gene X and gene Y in the first encoding reaction is a reflection of this pooling.

In a second encoding PCR, gene of interest X can be queried with a first probe comprising a 5' addressable primer portion A, an identifying portion 2, and a target specific portion, and a second probe comprising a target specific portion and a 3' addressable primer portion B. Gene of interest Y can be queried with a first probe comprising a 5' addressable primer portion C, an identifying portion 2, and a target specific portion, and a second probe comprising a target specific portion and a 3' addressable primer portion D. In such a scheme, (in a fashion analogous to that depicted in FIG. 9 for non-pooled samples), the pooled sample identity for a given expressed gene species can be encoded with the identifying portion, and the identity of a given expressed gene species can be encoded with the addressable primer portions. The quantity of gene X and gene Y in the second encoding reaction is a result of at least two pooled samples; for example, at least two diseased tissues are pooled together, and the quantity of gene X and gene Y in the second encoding reaction is a reflection of this pooling.

After the first and second encoding PCRs are performed, the reaction products can be combined together. The combined encoding PCRs can then be split into at least two decoding amplification reactions. The decoding amplification reactions can comprise a first decoding amplification reaction comprising an address primer A, an address primer B, labeling probe 1, and labeling probe 2, and a second decoding amplification reaction comprising an address primer C, address primer D, labeling probe 1, and labeling probe 2. Each decoding amplification reaction can result in the production of signal from labeling probe 1 and labeling probe 2. The ratio of labeling probe 1 to labeling probe 2 in any given decoding amplification reaction can provide a measure of the difference in expression level for a given gene between two pooled samples. In the present embodiment, the first decoding amplification reaction allows for a quantification of gene X between the first pooled sample and the second pooled sample based on the ratio of signal from labeling probe 1 verses labeling probe 2. The second decoding amplification reaction allows for a quantification of gene Y between the first pooled sample and the second pooled sample based on the ratio of signal from labeling probe 1 verses labeling probe 2.

It will be appreciated that pooling need not involve multiple samples. For example, a single pooled sample can be analyzed according to the present teachings in a manner similar to FIG. 8 on single samples.

Comparison of SNPs in a Single Sample with a Ligation Encoding Reaction

The addressable primer portions of the ligation probes of the encoding reaction, and the address primers of the decoding amplification reaction, can provide for detection of the presence or absence, or quantification, of a plurality of target polynucleotides. The addressable primer portions and the battery of corresponding address primers of the present teachings can provide for increased detection of up to a large number of target polynucleotides, while minimizing unique reagent compositions, allowing for the redundant use of a battery of address primer sets as will become more clear in the following illustrative embodiments.

Figure 11A:
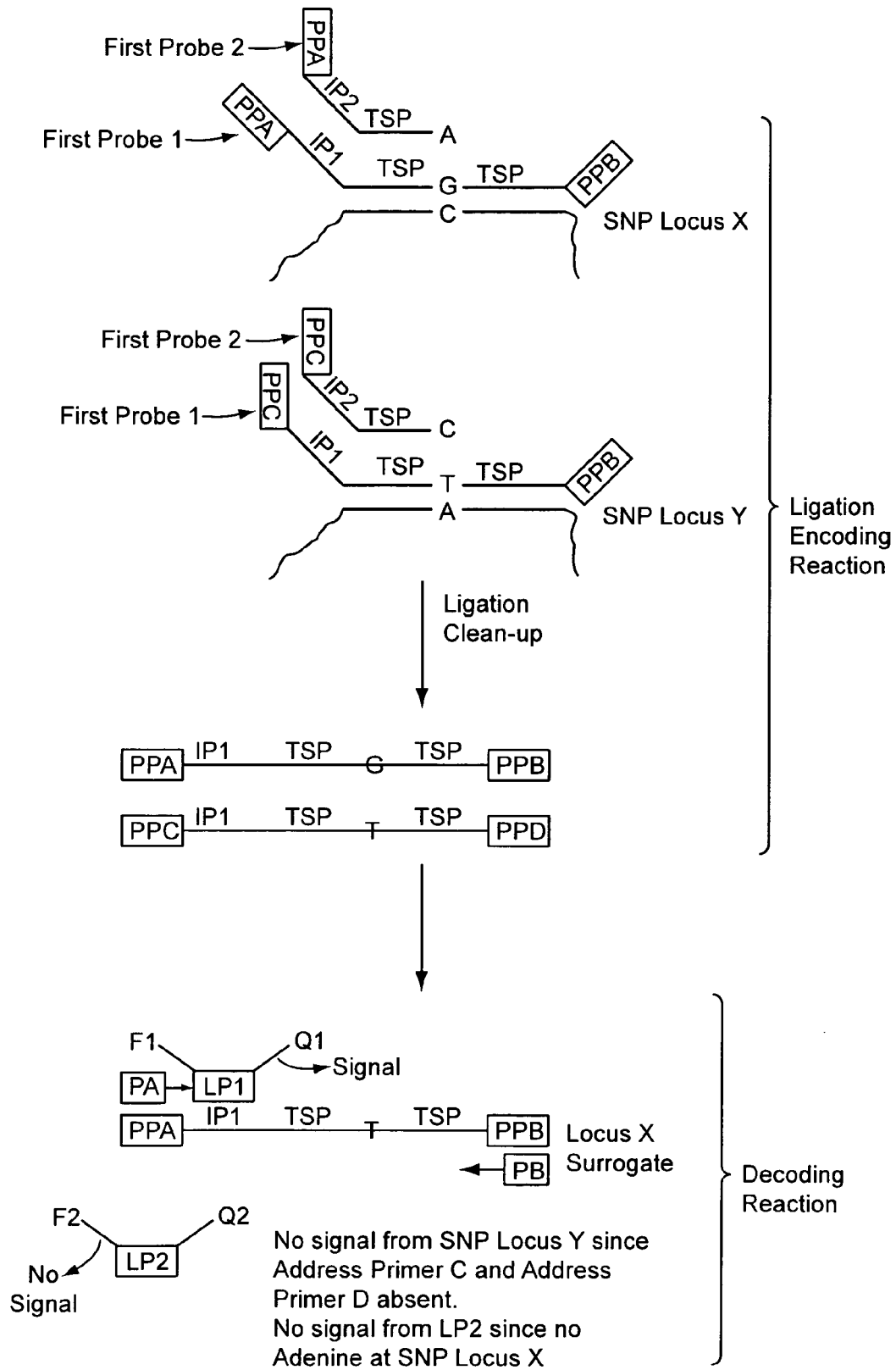
FIG. 11 depicts certain compositions and reaction interactions in accordance with some embodiments of the present teachings.

For example as shown schematically in FIG. 11A, a given SNP locus X comprising at least two allelic variants can be queried in an encoding ligation reaction with a first probe 1 comprising a 5' addressable primer portion A, an identifying portion 1, and a target specific portion, wherein the target specific portion comprises a discriminator nucleotide 1 (here, a G), a first probe 2 comprising a 5' addressable primer portion A, an identifying portion 2, and a target specific portion wherein the target specific portion comprises a discriminator nucleotide 2 (here an A), and a second probe comprising a target specific portion and a 3' addressable primer portion B.

A given SNP locus Y comprising at least two allelic variants can be queried in the same encoding ligation reaction as SNP locus X. SNP locus Y can be queried with a first probe 1 comprising a 5' addressable primer portion C, an identifying portion 1, and a target specific portion, wherein the target specific portion comprises a discriminating nucleotide 1 (here, a T), and a second probe comprising a target specific portion and a 3' addressable primer portion D. Also in the first encoding reaction, SNP locus Y can be queried with a first probe 2 comprising a 5' addressable primer portion C, an identifying portion 2, and a target specific portion, wherein the target specific portion comprises a discriminator nucleotide 2 (here, a C), and a second probe comprising a target specific portion and a 3' addressable primer portion D.

In such a scheme, the identity a given SNP locus can be encoded with the addressable primer portions, and the identity of a given variant at a given SNP locus (e.g.—the discriminating nucleotide) encoded with the identifying portion. After the encoding ligation reaction is performed, the reaction products can be split into at least two decoding amplification reactions. The decoding amplification reactions can comprise a first decoding amplification reaction (shown) comprising an address primer A, an address primer B, a labeling probe 1 and a labeling probe 2, and a second decoding amplification reaction (not shown) comprising an address primer C, address primer D, a labeling probe 1 and a labeling probe 2. Each decoding amplification reaction can result in the production of signal from labeling probe 1 and/or labeling probe 2. The quantity of signal of labeling probe 1 and/or labeling probe in any given decoding amplification reaction can provide for detection of a SNP variant at a given SNP locus in a given sample.

In the present embodiment, the first decoding amplification reaction (shown) allows for detection SNP locus X in the sample based on amplification with address primer A and address primer B. Detection of signal from labeling probe 1 indicates the presence of SNP variant 1 at SNP locus X. Detection of signal from labeling probe 2 would indicate the presence of SNP variant 2 at SNP locus X. Detection of signal from both labeling probe 1 and labeling probe 2 would indicate the presence of both SNP variant 1 and SNP variant 2 at SNP locus X. In the context of allelic variants at SNP locus X for example, detection of labeling probes in this manner can allow for the determination of a homozygote SNP variant 1 at SNP locus X, determination of homozygote SNP variant 2 at SNP locus X, or determination of a heterozygote SNP variant 1 and SNP variant 2 at SNP locus X.

In the present embodiment, the second decoding amplification reaction (not shown) allows for detection of SNP locus Y in the sample based on amplification with address primer C and address primer D. Detection of signal from labeling probe 1 indicates the presence of SNP variant 1 at SNP locus Y. Detection of signal from labeling probe 2 would indicate the presence of SNP variant 2 at SNP locus Y. Detection of signal from both labeling probe 1 and labeling probe 2 would indicate the presence of both SNP variant 1 and SNP variant 2 at SNP locus Y. In the context of allelic variants at SNP locus Y for example, detection of labeling probes in this manner can allow for the determination of a homozygote SNP variant 1 at SNP locus Y, determination of homozygote SNP variant 2 at SNP locus Y, or determination of a heterozygote SNP variant 1 and SNP variant 2 at SNP locus Y.

It will be appreciated that in the present embodiment, and in the present teachings generally, the particular identity of discriminating nucleotide "1" or "2", etc, is a not a limitation. For illustrative purposes in the context of the present embodiment depicted in FIG. 11A, discriminating nucleotide 1 of the target specific portion of the first probe 1 querying SNP locus X can be for example a cytosine, thereby allowing for determination of a guanine nucleotide as the nucleotide variant of SNP locus X. Discriminating nucleotide 2 of the target specific portion of the first probe 2 querying SNP locus X can be for example adenine, thereby allowing for determination of a thymine as the nucleotide variant of SNP locus X. Discriminating nucleotide 1 of the target specific portion of the first probe 1 querying SNP locus Y can be for example thymine, thereby allowing for determination of a adenine nucleotide as the nucleotide variant of SNP locus Y. Discriminating nucleotide 2 of the target specific portion of the first probe 2 querying SNP locus Y can be for example cytosine, thereby allowing for determination of a guanine nucleotide as the nucleotide variant of SNP locus Y. Thus, it will be appreciated that the particular identity of "discriminating nucleotide 1" can vary according to the context of the embodiment, and that the term "discriminating nucleotide 1" and the like is a convenient way of illustrating the relationship of the discriminating nucleotide to a particular identifying portion to a particular probe, as appropriate in various embodiments of the present teachings.

Comparison of SNPs in a Single Sample with a Looped-Linker Ligation Encoding Reaction The addressable primer portions of the ligation probes of the encoding reaction, and the address primers of the decoding amplification reaction, can provide for detection of the presence or absence, or quantification, of a plurality of target polynucleotides. The addressable primer portions and the battery of corresponding address primers of the present teachings can provide for increased detection of up to a large number of target polynucleotides, while minimizing unique reagent compositions, allowing for the redundant use of a battery of address primer sets, as well as potentially the redundant use of probe looped linkers, as will become more clear in the following illustrative embodiments.

Figure 11B:
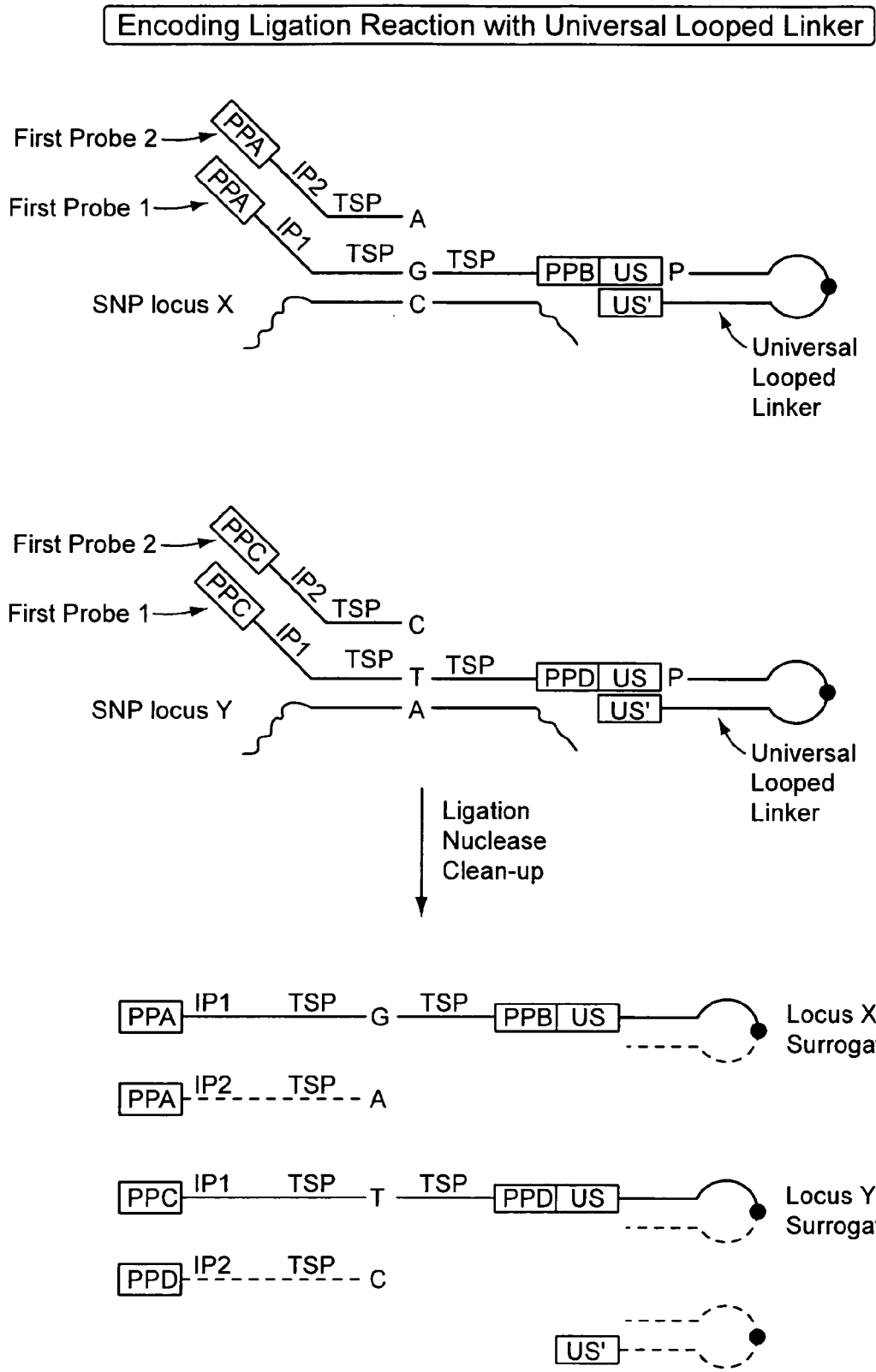

For example as shown in FIG. 11B, a given SNP locus X comprising at least two allelic variants can be queried in an encoding ligation reaction with a first probe 1 comprising a 5' addressable primer portion A, an identifying portion 1, and a target specific portion wherein the target specific portion comprises a discriminator nucleotide 1 (here, a G), a first probe 2 comprising a 5' addressable primer portion A, an identifying portion 2, and a target specific portion wherein the target specific portion comprises a discriminator nucleotide 2 (here, an A), and a second probe comprising a target specific portion, a 3' addressable primer portion B, and a universal splint portion (US).

A universal splint can hybridize to its complementary region on a looped linker, thereby allowing for the ligation of the 5' end phosphate group (here, a P) of the looped linker with the second probe. Such an approach can facilitate nuclease-mediated removal of unincorporated probes. Further, in some embodiments, by using a universal reverse linker the cost associated with the blocking group (shown as a filled circle) can be minimized, since the same blocking group on the same looped linker can be made in bulk. In some embodiments, the blocking group for the looped linker is 2'methoxy uracil, though it will be appreciated that any suitable blocker conferring the desired nuclease resistance can be employed (for example C18 spacers, and other nuclease resistant modified nucleotides, PEG (poly-ethylene glycol), TEG, and the like) and are within the scope of the present teachings.

A given SNP locus Y comprising at least two allelic variants can be queried in the same encoding ligation reaction as SNP locus X. SNP locus Y can be queried with a first probe 1 comprising a 5' addressable primer portion C, an identifying portion 1, and a target specific portion, wherein the target specific portion comprises a discriminating nucleotide 1 (here, a T), a first probe 2 comprising a 5' addressable primer portion C, an identifying portion 2, and a target specific portion, wherein the target specific portion comprises a discriminatory nucleotide 2 (here, a C), and a second probe comprising a target specific portion and a 3' addressable primer portion D, and a universal splint portion (US).

In such a scheme, the identity a given SNP locus can be encoded with the addressable primer portions, and the identity of a given variant at a given SNP locus (e.g.—the discriminating nucleotide) encoded with the identifying portion.

After the encoding ligation reaction is performed, the reaction mixture can be treated with 5' acting and 3' acting nucleases, and unligated reaction components degraded (indicated in FIG. 11 with dotted lines). For additional information regarding nuclease mediated clean-up of unligated reaction probes, and the use of looped linker compositions and unlooped linker compositions, see U.S. Provisional Application 60/517,470.

After the encoding ligation reaction is performed, and an optional nuclease-mediated removal of undesirable reaction components, the reaction products can be split into at least two decoding amplification reactions. (It will be appreciated, too, that the encoding reactions can be combined and a clean-up performed together). The decoding amplification reactions can comprise a first decoding amplification reaction comprising an address primer A, an address primer B, a labeling probe 1 and a labeling probe 2, and a second decoding amplification reaction comprising an address primer C, address primer D, a labeling probe 1 and a labeling probe 2. Each decoding amplification reaction can result in the production of signal from labeling probe 1 and/or labeling probe 2. The quantity of signal of labeling probe 1 and/or labeling probe in any given decoding amplification reaction can provide for detection of a SNP variant at a given SNP locus in a given sample.

Figure 12A:
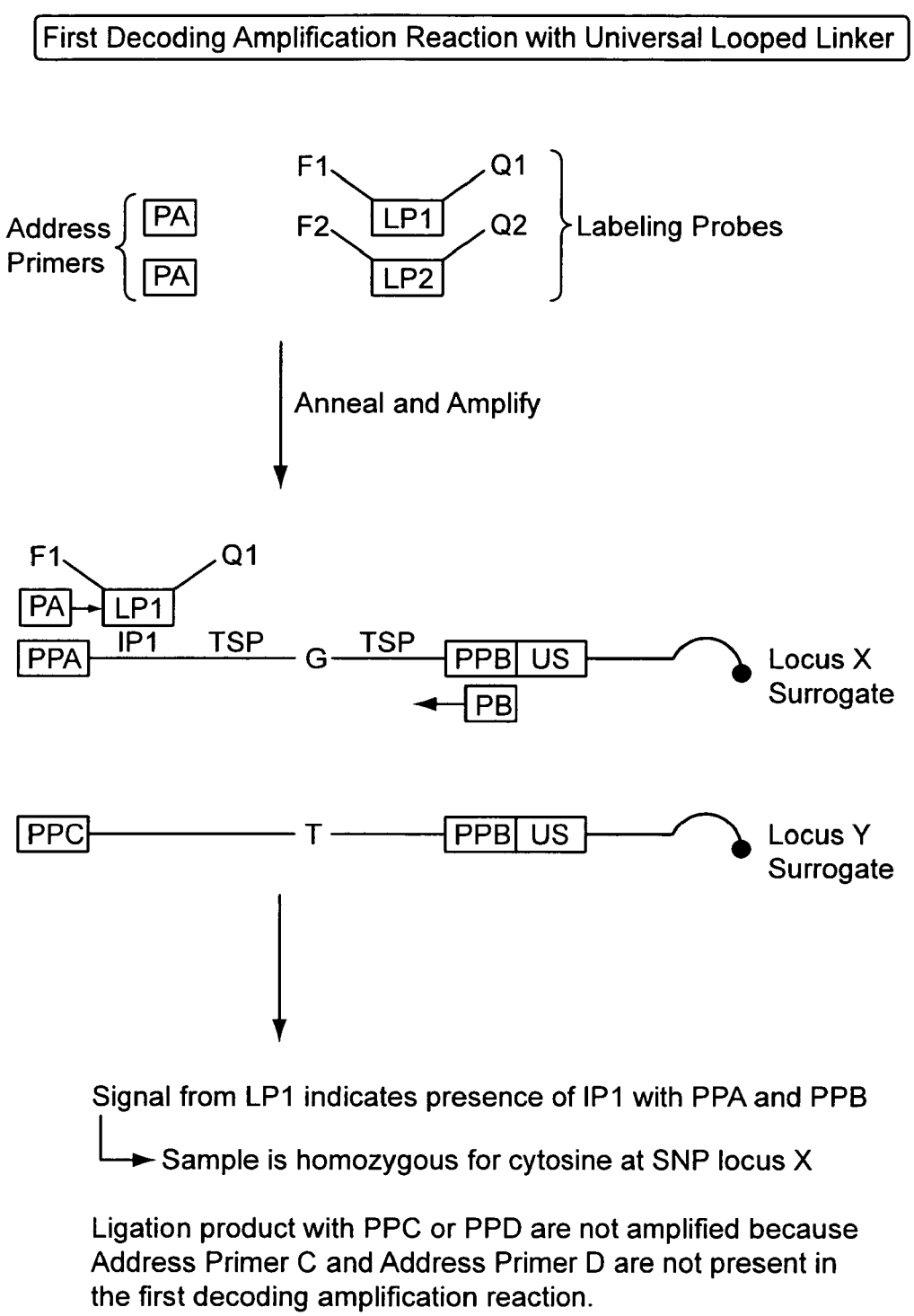
FIG. 12 depicts certain compositions and reaction interactions in accordance with some embodiments of the present teachings.

In the present embodiment, the first decoding amplification reaction (depicted in FIG. 12B) allows for detection SNP locus X in the sample based on amplification with address primer A and address primer B. Detection of signal from labeling probe 1 would indicate the presence of SNP variant 1 comprising a cytosine base at SNP locus X. Detection of signal from labeling probe 2 would indicate the presence of SNP variant 2 at SNP locus X. Detection of signal from both labeling probe 1 and labeling probe 2 would indicate the presence of both SNP variant 1 and SNP variant 2 at SNP locus X. In the context of allelic variants at SNP locus X, detection of labeling probes in this manner can allow for the determination of a homozygote SNP variant 1 at SNP locus X, determination of homozygote SNP variant 2 at SNP locus X, or determination of a heterozygote SNP variant 1 and SNP variant 2 at SNP locus X. In the context of allelic variants at SNP locus X in the present embodiment, as indicated in FIG. 12A, the presence of signal from labeling probe 1 indicates the sample comprises an allelic variant with cytosine at SNP locus X, and hence, a homozygote.

Figure 12B:
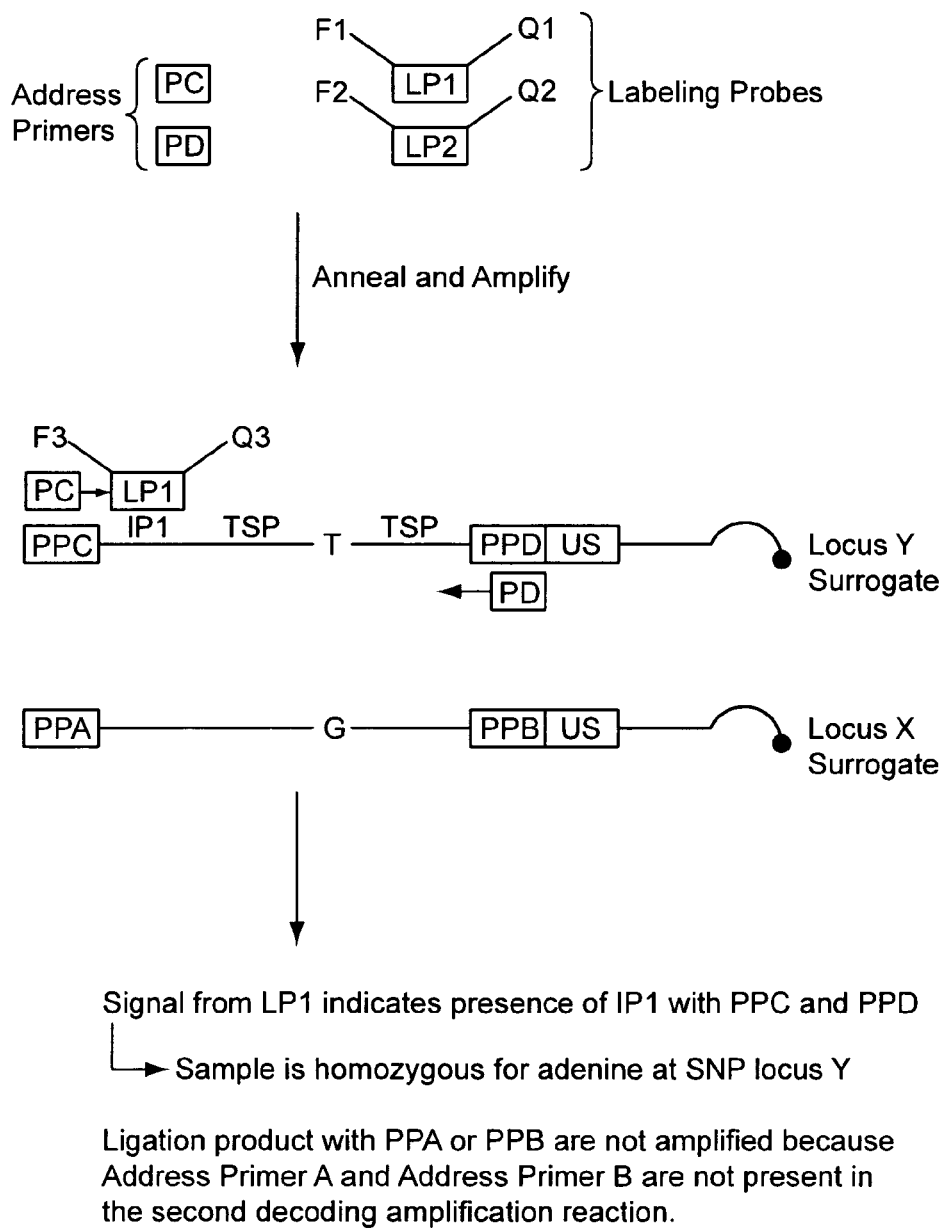

In the present embodiment depicted in FIG. 12B, the second decoding amplification reaction allows for detection of SNP locus Y in the sample based on amplification with address primer C and address primer D. Detection of signal from labeling probe 1 would indicate the presence of SNP variant 1 at SNP locus Y. Detection of signal from labeling probe 2 would indicate the presence of SNP variant 2 at SNP locus Y. Detection of signal from both labeling probe 1 and labeling probe 2 would indicate the presence of both SNP variant 1 and SNP variant 2 at SNP locus Y. In the context of allelic variants at SNP locus Y for example, detection of labeling probes in this manner can allow for the determination of a homozygote SNP variant 1 at SNP locus Y, determination of homozygote SNP variant 2 at SNP locus Y, or determination of a heterozygote SNP variant 1 and SNP variant 2 at SNP locus Y. In the context of allelic variants at SNP locus Y in the present embodiment, as indicated in FIG. 12B, the presence of signal from labeling probe 1 indicates the sample comprises an allelic variant with adenine at SNP locus Y, and hence, a homozygote.

It will be appreciated that in the present embodiment, and in the present teachings generally, the particular identity of discriminating nucleotide "1" or "2", etc, is a not a limitation. For illustrative purposes in the context of the present embodiment, discriminating nucleotide 1 of the target specific portion of first probe 1 querying SNP locus X can be for example a guanine, thereby allowing for determination of a cytosine nucleotide as the nucleotide variant of SNP locus X. Discriminating nucleotide 2 of the target specific portion of the first probe 2 querying SNP locus X can be for example adenine, thereby allowing for determination of a thymine as the nucleotide variant of SNP locus X. Discriminating nucleotide 1 of the target specific portion of the first probe 1 querying SNP locus Y can be for example thymine, thereby allowing for determination of an adenine nucleotide as the nucleotide variant of SNP locus Y. Discriminating nucleotide 2 of the target specific portion of the first probe 2 querying SNP locus Y can be for example cytosine, thereby allowing for determination of a guanine nucleotide as the nucleotide variant of SNP locus Y. Thus, it will be appreciated that the particular identity of "discriminating nucleotide 1" can vary according to the context of the embodiment, and that the term "discriminating nucleotide 1" and the like is a convenient way of illustrating the relationship of the discriminating nucleotide to a particular identifying portion to a particular probe, as appropriate in various embodiments of the present teachings.

Multi-Sample Comparison of SNPs with a Ligation Encoding Reaction Some embodiments of the present teachings provide for comparison analyses of at least one given SNP locus between at least two samples. The addressable primer portions of the ligation probes of the encoding reaction, and the address primers of the decoding amplification reaction, can provide for detection of the presence or absence, or quantification, of at least one given SNP locus between two samples. The addressable primer portions and the battery of corresponding address primers of the present teachings can provide for increased detection of target polynucleotides while minimizing unique reagent compositions, allowing for the redundant use of a battery of address primer sets as will become more clear in the following illustrative embodiments.

In some embodiments of the present teachings, the encoding ligation reaction can be performed in parallel on at least two samples. For example, genomic DNA can be acquired from a first source. Further, genomic DNA can be acquired from a second source. An encoding reaction can then be performed on each of the two samples individually. The individually performed encoding reactions can then be combined together into a single mixture, and at least one decoding amplification reaction performed. The decoding reaction can allow for a comparison of SNP loci variants between at least one SNP locus between the two samples.

Figure 13A:
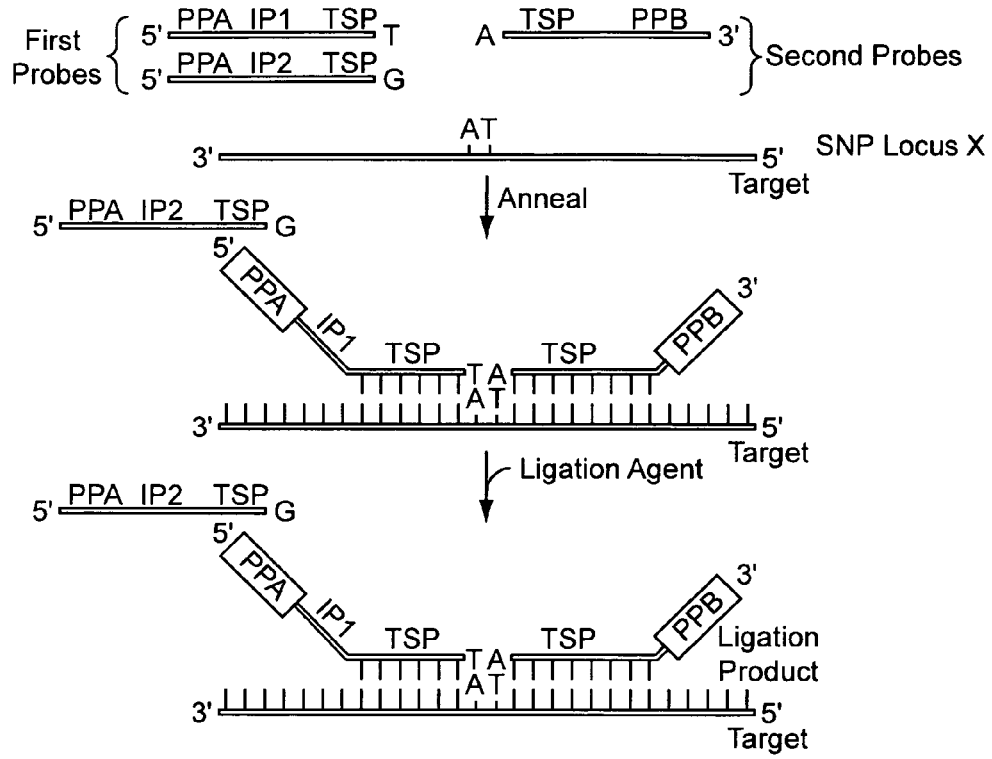
FIG. 13 depicts certain compositions and reaction interactions in accordance with some embodiments of the present teachings.

For example, as depicted in FIG. 13A (top), a given SNP locus X can be queried in a first encoding ligation reaction with a first probe 1 comprising a 5' addressable primer portion A, an identifying portion 1, and a target specific portion, wherein the target specific portion comprises a discriminating nucleotide 1 (here, a T), a first probe 2 comprising a 5' addressable primer portion A and an identifying portion 2, and a target specific portion, wherein the target specific portion comprises a discriminating nucleotide 2 (here, a G), and a second probe comprising a target specific portion and a 3' addressable primer portion B.

Also in the first encoding ligation reaction depicted in FIG. 13A (bottom), a given SNP locus Y can be queried with a first probe 1 comprising a 5' addressable primer portion C, an identifying portion 1, and a target specific portion, wherein the target specific portion comprises a discriminating nucleotide 1 (here a T), a first probe 2 comprising a 5' addressable primer portion C, an identifying portion 2, and a target specific portion, wherein the target specific portion comprises a discriminating nucleotide 2 (here a C), and a second probe comprising a target specific portion and a 3' addressable primer portion D.

Figure 13A:
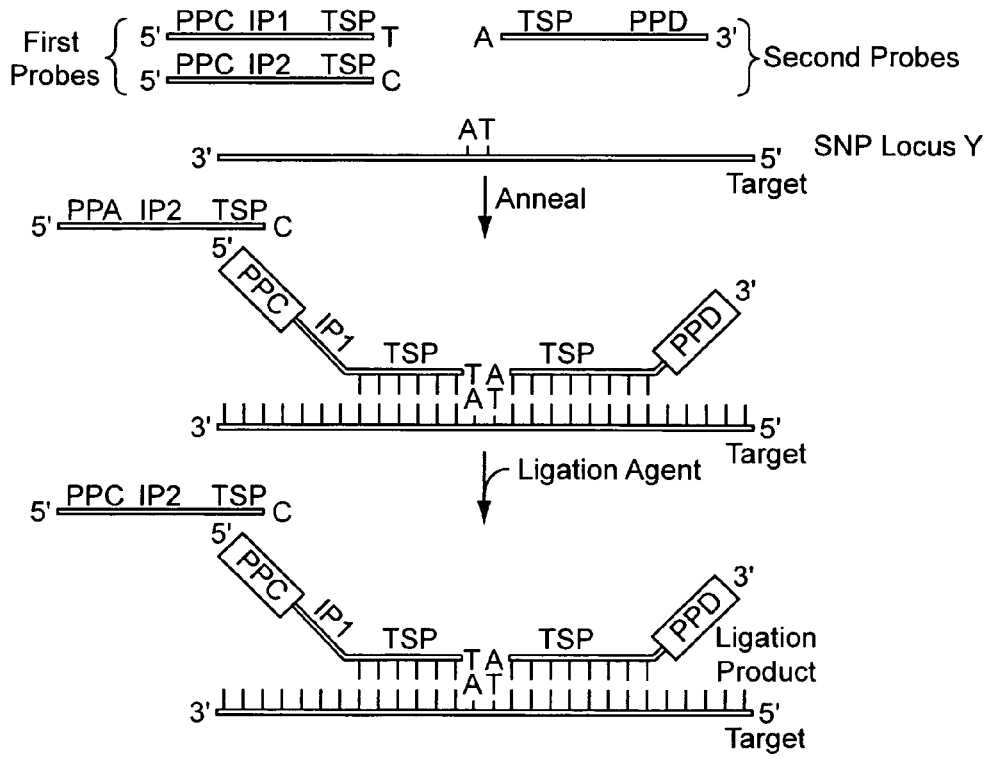
Figure 13B:
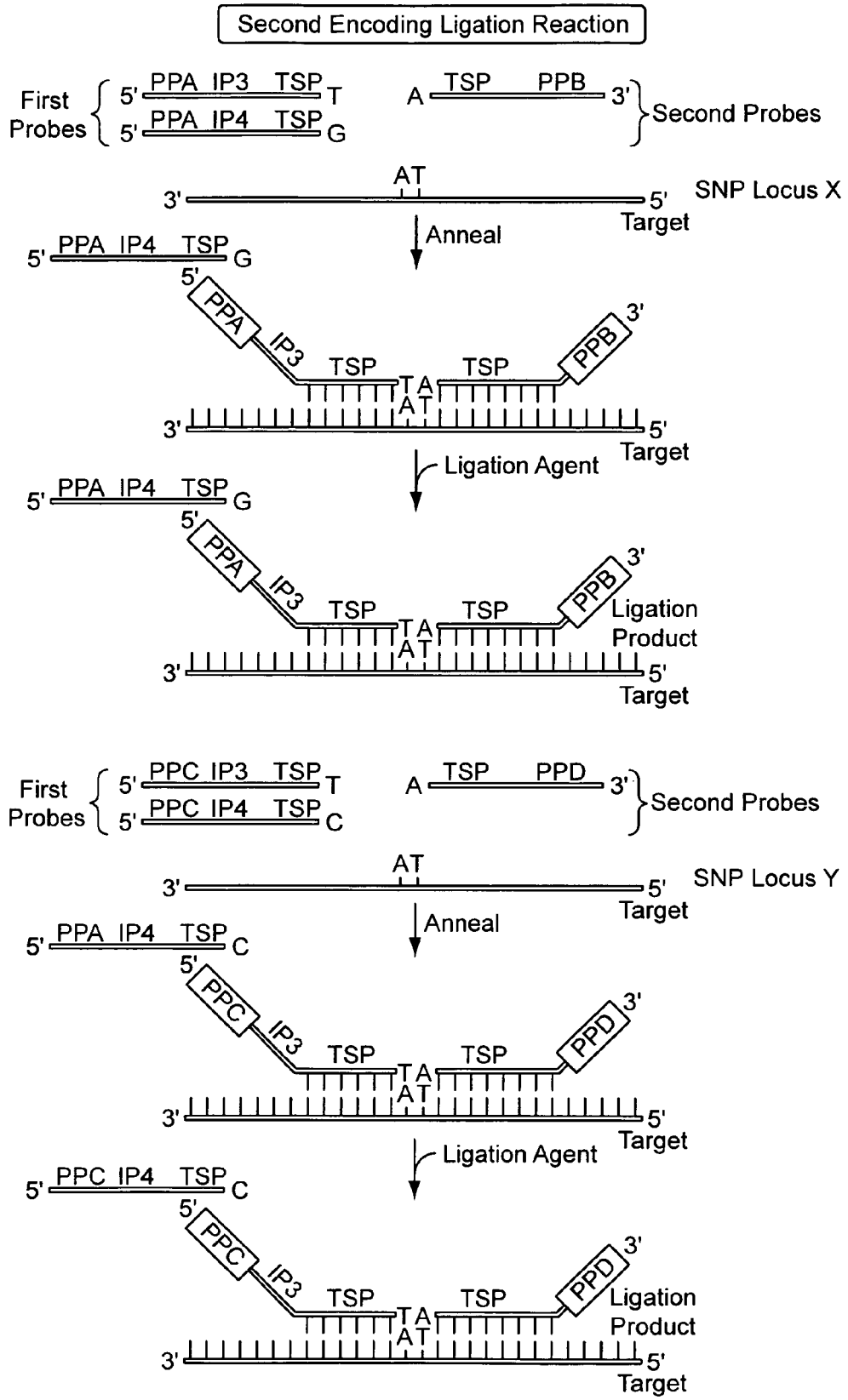

A given SNP locus X can be queried in a second encoding ligation reaction (as depicted in FIG. 13B, top) with a first probe 1 comprising a 5' addressable primer portion A, an identifying portion 3, and a target specific portion, wherein the target specific portion comprises a discriminating nucleotide 1 (here a T), a first probe 2 comprising a 5' addressable primer portion A, an identifying portion 4, and a target specific portion, wherein the target specific portion comprises a discriminating nucleotide 2 (here, a G), and a second probe comprising a target specific portion and a 3' addressable primer portion B.

Also in the second encoding ligation reaction depicted in FIG. 13B (bottom), a given SNP locus Y can be queried with a first probe 1 comprising a 5' addressable primer portion C, an identifying portion 3, and a target specific portion, wherein the target specific portion comprises a discriminating nucleotide 1 (here, a T), a first probe 2 comprising a 5' addressable primer portion C, an identifying portion 4, and a target specific portion, wherein the target specific portion comprises a discriminating nucleotide 2 (here a C), and a second probe comprising a target specific portion and a 3' addressable primer portion D.

In such a scheme, as shown in FIGS. 13A and 13B, the identity of a given SNP locus can be encoded with the addressable primer portions, and the sample of origin and a given SNP variant for a SNP locus can be encoded with the identifying portion.

After the first and second encoding ligation reactions are performed, the reaction products can be combined together. The combined encoding reaction products can then be split into at least two decoding amplification reactions. The decoding amplification reactions can comprise a first decoding amplification reaction comprising an address primer A, an address primer B, labeling probe 1, labeling probe 2, labeling probe 3, and labeling probe 4, and a second decoding amplification reaction comprising an address primer C, address primer D, labeling probe 1, labeling probe 2, labeling probe 3, and labeling probe 4. Each decoding amplification reaction can result in the production of signal from any of the labeling probes 1-4, provided that the appropriate address primers are present to amplify the appropriate target with the binding site (for example, identifying portion or identifying portion complement) for a given labeling probe. The presence of signal from a given labeling probe in a given decoding amplification reaction can provide for detection of the presence of a SNP variant difference between two samples.

Figure 14A:
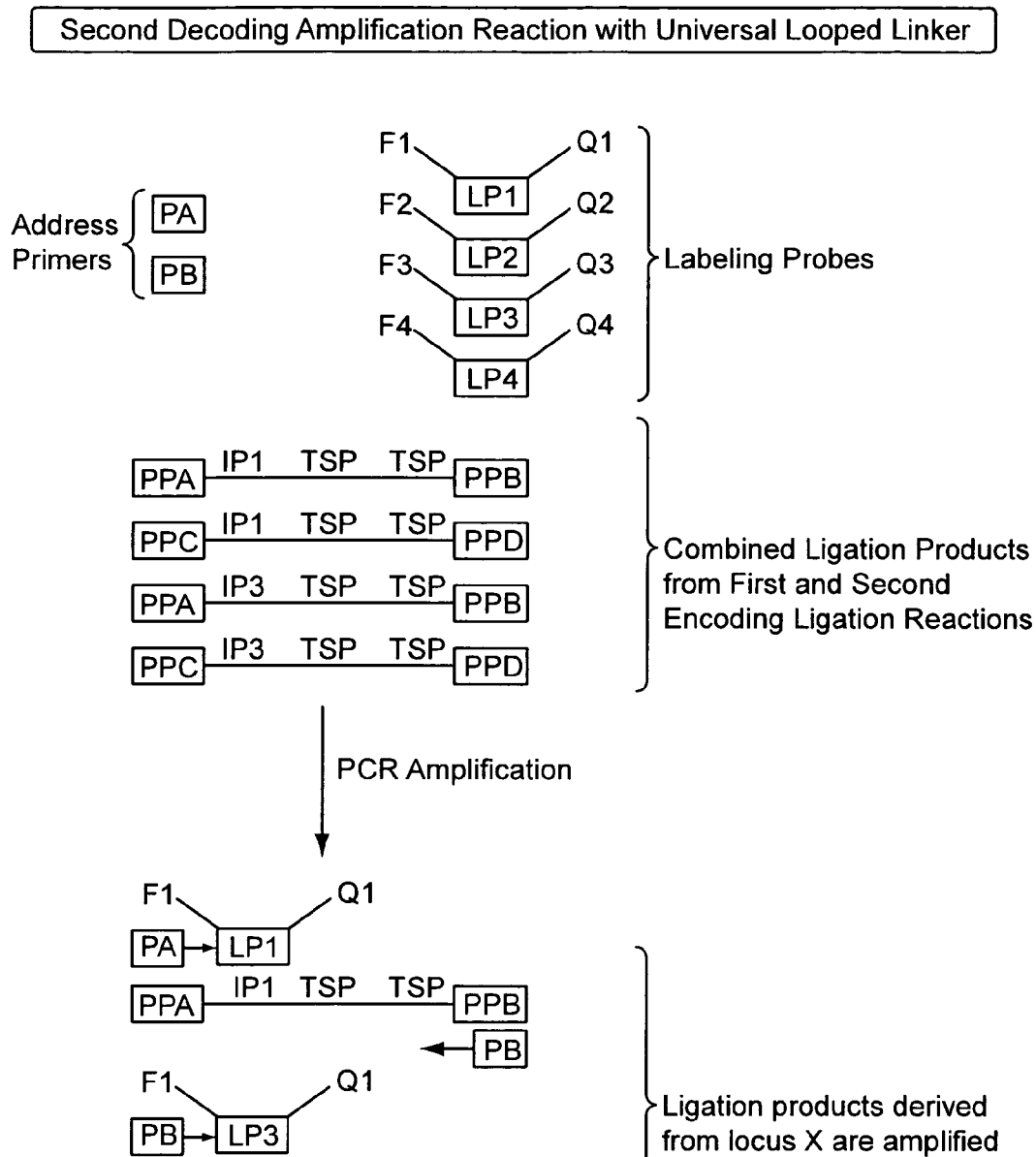
FIG. 14 depicts certain compositions and reaction interactions in accordance with some embodiments of the present teachings.

In the present embodiment, the first decoding amplification reaction (as depicted in FIG. 14A) allows for detection of variants of locus X between the first sample and the second sample based on the presence of signal from labeling probe 1 and labeling probe 3. Since only address primer A and address primer B (and not address primer C and address primer D) are present in the first decoding amplification reaction, only ligation products derived from locus X can be amplified. In the ligation encoding reactions, the locus X variants that were present were encoded with identifying portion 1 and identifying portion 3. Hence, in the first decoding amplification reaction, labeling probe 1 and labeling probe 3 will hybridize to their corresponding identifying portion, and amplification of the ligation products with address primer A and address primer B results in signal for label probe 1 and label probe 3. In the present embodiment, in the context of allelic variants for SNP locus X, signal from label probe 1 can be used to indicate the presence of homozygote adenine allele in the first sample, and signal from label probe 3 can be used to indicate the presence of a homozygote adenine allele in the second sample.

Figure 14B:
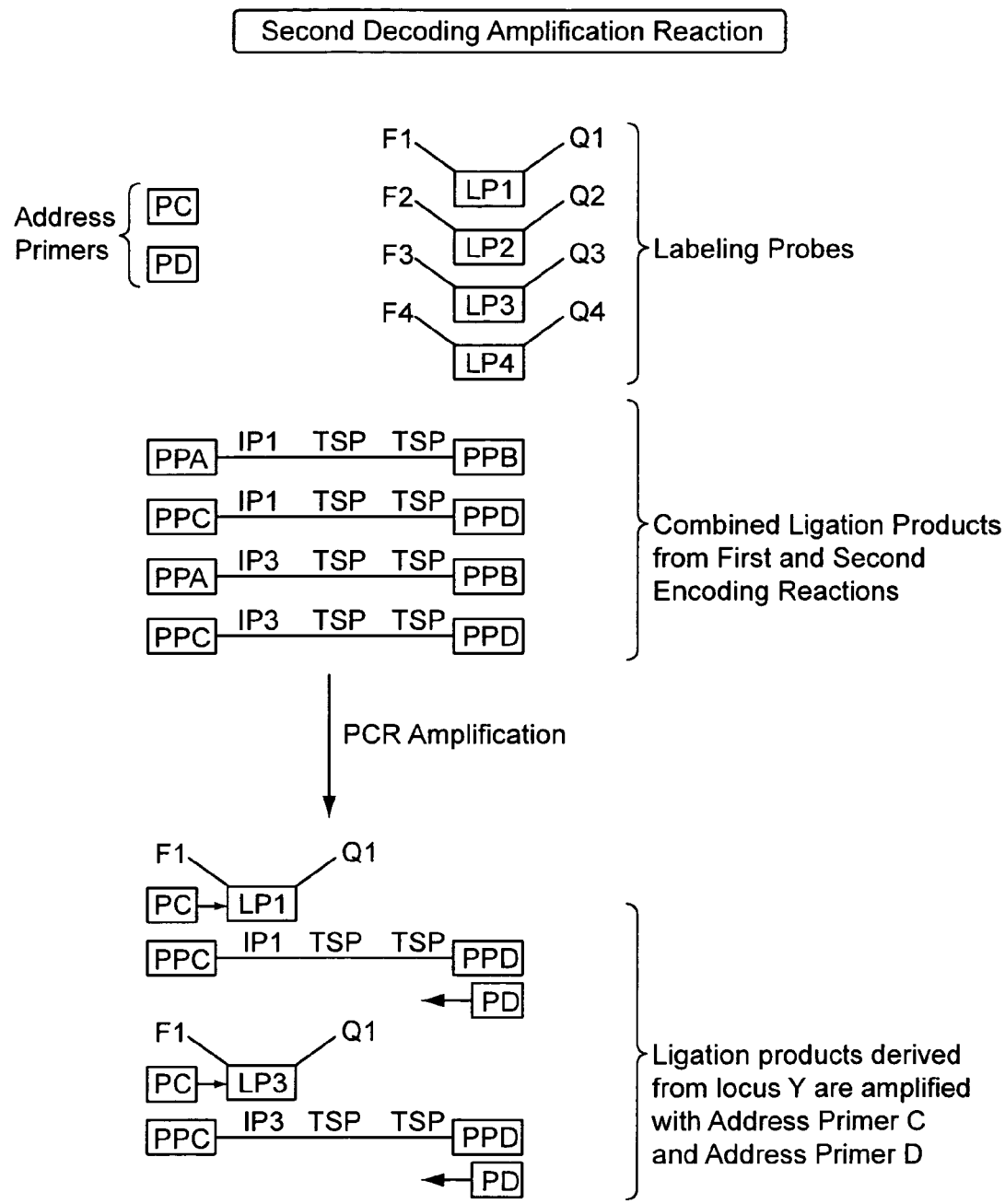

In the present embodiment, the second decoding amplification reaction (as depicted in FIG. 14B) allows for detection of variants of locus Y between the first sample and the second sample based on the presence of signal from labeling probe 1 and labeling probe 3. Since only address primer C and address primer D (and not address primer A and address primer B) are present in the second decoding amplification reaction, only ligation products derived from locus Y can be amplified. In the ligation encoding reactions, the locus Y variants that were present were encoded with identifying portion 1 and identifying portion 3. Hence, in the first decoding amplification reaction, labeling probe 1 and labeling probe 3 will hybridize to their corresponding identifying portions, and amplification of the ligation products with address primer C and address primer D results in signal for label probe 1 and label probe 3.

In the present embodiment, in the context of allelic variants for SNP locus Y, signal from label probe 1 can be used to indicate the presence of homozygote adenine allele in the first sample, and signal from label probe 3 can be used to indicate the presence of a homozygote adenine allele in the second sample.

It will be appreciated that FIGS. 13 and 14 are presented in the absence of universal looped linkers, as those presented in FIGS. 11 and 12. The present teachings contemplate the use of universal looped linkers, non-universal looped linkers, universal non-looped linkers, and non-universal non-looped linkers, in any encoding ligation reaction, as well as potentially encoding PCR reactions, as well as contemplate the use of conventional single stranded probes in any encoding reaction. Further, it will be appreciated that a universal looped linker can reside not only on the downstream probe, as depicted in FIGS. 11 and 12, but also on the upstream probe. Further, a universal looped linker can reside only on the upstream probe, and not the downstream probe. Various permutations of looper linkers and non-looped linkers, universal and non-universal linkers, on the upstream, and/or downstream probes for different target polynucleotides within a sample, as well as between samples, is also contemplated and within the scope of the present teachings. For further information on looped and non-looped linker compositions, see for example U.S. Provisional Application 60/517,470, as well as the Applied Biosystems SNPlex™ Genotyping System Chemistry Guide.

Multi-Sample Comparison of SNP Loci from Pooled Samples with a Ligation Encoding Reaction Some embodiments of the present teachings provide for comparison analyses of at least one given SNP locus between at least two samples, wherein at least one of the at least two samples is pooled from more than one source. The addressable primer portions of the ligation probes of the encoding reaction, and the address primers of the decoding amplification reaction, can provide for detection of the presence or absence, or quantification, of at least one SNP locus between two samples. The addressable primer portions and the battery of corresponding address primers of the present teachings can provide for increased detection of target polynucleotides while minimizing unique reagent compositions, allowing for the redundant use of a battery of address primer sets as will become more clear in the following illustrative embodiments.

Figure 15:
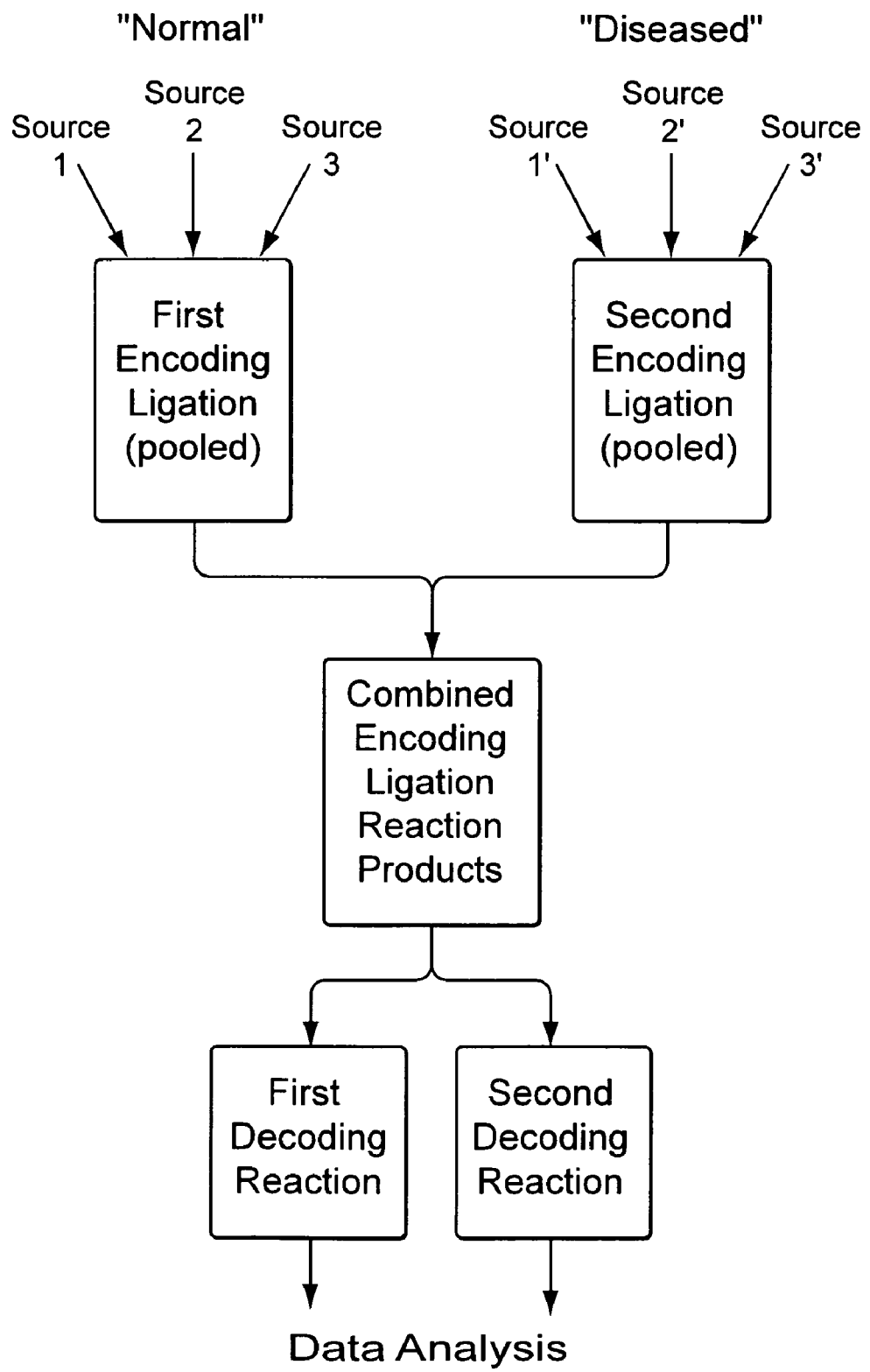
FIG. 15 depicts a flowchart in accordance with some embodiments of the present teachings.
Figure 16:
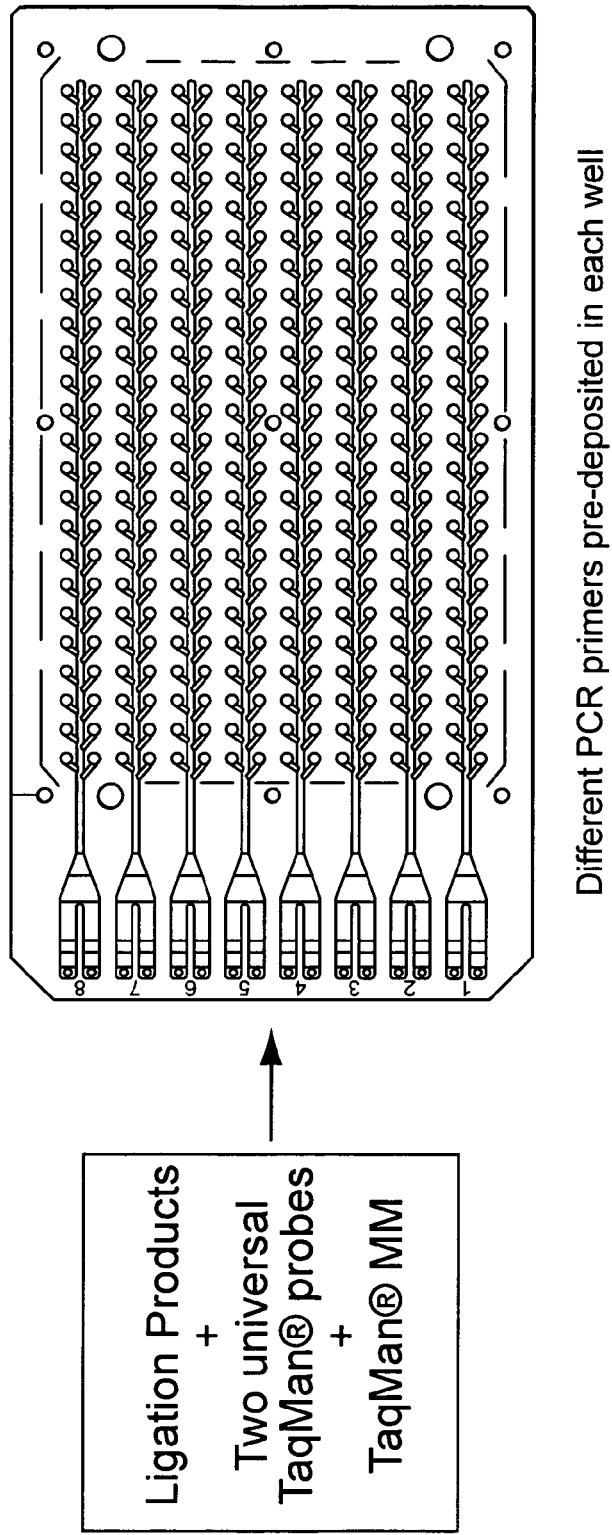
FIG. 16 depicts a flowchart in accordance with some embodiments of the present teachings.

In some embodiments of the present teachings, the encoding ligation reaction can be performed in parallel on at least two samples, wherein at least one of the two samples is pooled from at least two sources. For example, gDNA can be acquired from at least two first sources. Further, gDNA can be acquired from at least two second sources. A first encoding ligation reaction can be performed on the first pooled sample, and a second encoding ligation reaction can be performed on the second pooled sample. The products resulting from the individually performed encoding reactions can then be combined together into a single mixture, and at least one decoding amplification reaction performed. The decoding reaction can allow for a comparison of the SNP locus variants of at least one SNP locus between the two pooled samples. For a schematic of this process, see for example FIG. 15, which can be performed in a manner analogous with FIGS. 13 and 14 for non-pooled samples.

It will be appreciated that pooling need not involved multiple samples. For example, a single pooled sample can be analyzed according to the present teachings in a manner similar to the FIGS. 11 and 12 on single samples.

Exemplary Kits in Accordance with Some Embodiments of the Present Teachings

In some embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

In certain embodiments, a kit for detecting at least one target polynucleotide in a sample is provided. In some embodiments, a kit comprises: a ligation probe set for each target polynucleotide, the probe set comprising (a) at least one first probe, comprising a target-specific portion and a 5' addressable primer portion, and (b) at least one second probe, comprising a target-specific portion and a 3' primer-specific portion. The probes in each set are suitable for ligation together when hybridized adjacent to one another on a complementary target polynucleotide. One probe in each probe set can further comprise an identifying portion located between the addressable primer portion and the target-specific portion. In some embodiments, the kit further comprises at least one labeling probe comprising the sequence of the identifying portion or comprising a sequence complementary to the sequence of the identifying portion.

In some embodiments, the kit comprises a labeling probe that has a first detectable signal value when it is not hybridized to a complementary sequence and a second detectable signal value of the labeled probe can be detected at least one of during and after an amplification reaction. In some embodiments, a threshold difference between the first detectable signal value and the second detectable signal value indicates the presence of the target polynucleotide, and no threshold difference between the first detectable signal value and the second detectable signal value indicates the absence of the target polynucleotide.

In some embodiments, kits further comprise address primer affixed to a second reaction vessel. In some embodiments, kits further comprise at least one address primer set comprising (i) at least one first primer comprising the sequence of the 5' addressable primer portion of the at least one first probe, and (ii) at least one second primer comprising a sequence complementary to the sequence of the 3' addressable primer portion of the at least one second probe.

In some embodiments wherein the decoding reaction vessel comprises a 384 well microplate and the application comprises SNP locus analysis of a single sample, address primers can be provided in each well, wherein for example two address primers are employed per SNP locus, thereby resulting in 384 address primer sets (for a total of 768 address primers).

In some embodiments wherein the decoding reaction vessel comprises a 384 well microplate and the application comprises SNP locus analysis of a single sample, address primers can be provided in each well, wherein for example one address primer is employed per SNP locus for an application comprising SNP locus analysis of a single sample, thereby resulting in 384 address primers (for a total of 384 address primers).

In some embodiments wherein the decoding reaction vessel comprises a 384 well microplate and the application comprises SNP locus analysis of a single sample, distinct address primers can be provided in each well along a row, thereby resulting in 24 unique 'row' primers. Further, distinct address primers can be provided in each well along a column, thereby resulting in 16 unique 'column' primers. Such embodiments in the art are referred to as NXM schemes. In some such embodiments, two address primers are employed per SNP locus, thereby resulting in 384 address primer sets (for a total of 40 address primers). For some additional non-limiting kit configurations, see for example FIG. 17. It will be appreciated that these and other configurations are possible with other reaction vessels as well, for example 96-well microtitre plates, as well as the Applied Biosystems Low Density Gene Expression Array (formerly the Microcard).

In certain embodiments, kits comprise one or more additional components, including, without limitation, at least one of: at least one polymerase, at least one transcriptase, at least one ligation agent, at least one kinase, at least one uracil N-glycosylase, oligonucleotide triphosphates, nucleotide analogs, reaction buffers, salts, ions, and stabilizers. In certain embodiments, kits comprise one or more reagents for purifying the ligation products, including, without limitation, at least one of dialysis membranes, chromatographic compounds, supports, nucleases and oligonucleotides.

In some embodiments, kit configurations are contemplated as in accordance with the Applied Biosystems SNPlex™ Genotyping System Chemistry Guide, comprising for example, universal looped linker compositions. Illustrative further teachings of looped linker compositions can be found in U.S. application Ser. No. 10/982,619 to Chen et al., In some embodiments of the present teachings, novel master mixes are contemplated. The encoding and decoding approaches for gene and protein expression and genotyping provided by the present teachings allow for the use of universal PCR primers as well as universal labeling probes. One aspect of these approaches is that including one, or more than one, labeling probe in a master mix is now possible. Thus, in some embodiments the present teachings provide for kits comprising a master mix, wherein the master mix comprises buffer, nucleotides, appropriate salts, polymerase, or combinations thereof, and additionally comprises at least one labeling probe.

For example, a master mix can comprise 20 mM Tris-HCl (pH 8.3 @ 20C), 1.5 mM MgCl2, 25 mM KCl, 0.05% Tween 20, 100 ug/ml of autoclaved gelatin or nuclease-free bovine serum albumin, 50 uM each dNTP, 2 units of Taq DNA polymerase, or combinations thereof, and at least one labeling probe. In some embodiments, the master mix can comprise various additives known to improve the performance of PCR in certain contexts, including stutter reduction and reducing non-specific amplification, including betaine, DMSO, sorbitol, and various osmolytes, as described for example in U.S. Pat. No. 6,841,349 to Coticone and Bloch, U.S. Pat. No. 6,783,940 to McLaughlin, Coticone and Bloch, and U.S. Pat. No. 6,780,588 to Coticone and Bloch. Various master mix components can generally be found in Innis et al., PCR protocols, 1990, Academic Press, and Sambrook et al., Molecular Cloning 3$^{rd}$ Edition.

In some embodiments, for example embodiments involving gene expression in one sample, a master mix can comprise buffer, nucleotides, appropriate salts, polymerase, or combinations thereof, and additionally comprise one labeling probe.

In some embodiments, for example embodiments involving gene expression two or more samples, a master mix can comprise buffer, nucleotides, appropriate salts, polymerase, or combinations thereof, and additionally comprise two or more labeling probes. In some embodiments, the two ore more labeling probes can be similar in sequence. In some embodiments, the two or more labeling probes can differ by as little as one nucleotide. In some embodiments, the two or more labeling probes can differ by as little as two nucleotides. In some embodiments, the two or more labeling probes can differ by as little as three or more nucleotides.

In some embodiments, for example embodiments involving genotyping of a single sample, a master mix can comprise buffer, nucleotides, appropriate salts, polymerase, or combinations thereof, and additionally comprise two or more labeling probes, plus or minus a passive reference dye, such as ROX.

In some embodiments, for example embodiments involving genotyping of a two or more samples, a master mix can comprise buffer, nucleotides, appropriate salts, polymerase, or combinations thereof, and additionally comprise four or more labeling probes, plus or minus a passive reference dye, such ROX.

In some embodiments, the master mix can comprise at least one labeling probe as well as a uracil-N-glycosylase. Primers in the decoding amplification reactions can comprise uracils, located for example somewhere other than the 3' end, thereby providing a way of minimizing unwanted carryover contamination and minimizing primer formation.

In some embodiments, the master mix can comprise at least one labeling probe as well as pyrophosphate. Primers in the decoding amplification reaction can undergo a pyrophosphorylis reaction, thereby allowing for greater specificity in the PCR. In some embodiments, a DNA polymerase such as AmpliTaq FS can be employed. In some embodiments, a DNA polymerase comprising the F667Y mutation can be employed. Additonal teaching of such pyrophosphorylysis approaches that can be applied in the context of the present teachings can be found in U.S. Pat. No. 6,534,269 and Published U.S. Application 2003/0092051A1, both to Liu.

Thus, in some embodiments of the present teachings, a composition of matter is provided, comprising a master mix and at least one labeling probe.

In some embodiments, the present teachings provide kits, wherein the kit comprises a master mix comprising at least one labeling probe. In some embodiments, a kit can comprise a master mix comprising at least one labeling probe and a plurality of encoding ligation probes. In some embodiments, a kit comprise a master mix comprising at least one labeling probe and a plurality of encoding PCR primers. In some embodiments, the present teachings provide a kit comprising a master mix comprising at least one labeling probe and a plurality of encoding PCR primers or ligation probes, as well as a plurality of vessels for performing a plurality of decoding amplification reactions. In some embodiments, the plurality of vessels for performing the plurality of decoding amplification reactions can comprise a microtitre plate, for example a 96 well plate or a 384 well plate, wherein the wells in the microtitre plate comprises address primers in each well.

In some embodiments, especially those in which proteins are to be detected, the present teachings contemplate kits comprising any of the aforementioned, or combinations thereof, as well as the inclusion of binders for target proteins. Such binders can include any binder, including antibodies and aptamers. In some embodiments, antibody binders can further comprise biotin, thereby facilitating downstream detection using streptavidinylated nucleic acid probes.

Some Additional Embodiments of the Present Teachings

In some embodiments, a cDNA of interest can further comprise a SNP. In some such embodiments, probes in the at least one encoding reaction can be designed in such manner as to distinguish between expressed allelic variants of a given gene. In some such embodiments, probes in the at least one encoding reaction can be designed in such manner with universal nucleotide as to not distinguish between expressed allelic variants of a given gene.

In some embodiments, the discriminating nucleotide is an LNA. In some embodiments, the discriminating LNA nucleotide is located at the 3' terminal position of a probe.

In some embodiments, the probes of the encoding reaction can comprise universal bases to mask unwanted SNPs (see Loakes, N. A. R. 29:12:2437-2447, and U.S. patent application Ser. No. 10/982619 to Chen et al., In some embodiments, the decoding reaction is an amplification reaction, but not a PCR. For other illustrative amplification procedures, see supra.

In some embodiments, the encoding reaction is not a ligation reaction nor is the encoding reaction a PCR, but can be other kinds of amplification reactions (as described supra) that comprise primers with addressable primer portions, identifying portions, or addressable primer portions and identifying portions.

In some embodiments, the encoding reaction comprises ligation of a single oligonucleotide to itself, as is known in the art for example in U.S. Pat. No. 5,871,921, wherein a ligated circle can be nicked and amplified. The addressable primer portions can be introduced into the single oligonucleotide, thereby allowing for PCR decoding in accordance with the present teachings. In some embodiments, a single addressable primer portion can be included in the oligonucleotide, whereupon ligation the circle can replicate itself in a rolling-circle mechanism.

In some embodiments, one target polynucleotide in a sample is queried. In some embodiments, between 1 and 48 target polynucleotides in a sample is queried. In some embodiments, between 49 and 96 target polynucleotides are queried. In some embodiments, between 96 and 192 target polynucleotides are queried. In some embodiments, between 193 and 384 target polynucleotides are queried. In some embodiments, between 385 and 768 target polynucleotides are queried. In some embodiments, between 769 and 1536 target polynucleotides are queried. In some embodiments, greater than 1536 target polynucleotides are queried. It will be appreciated that the above ranges correspond both to target polynucleotides present in a single sample, target polynucleotides present in at least two samples, and target polynucleotides present in at least two samples wherein at least one of the at least two samples comprises pooled samples. It will also be appreciated that the foregoing ranges of target polynucleotides corresponds to both target expressed genes, target SNP loci, target gene copy number, target methylated genomic regions, and, in general, the nature of the target polynucleotide is not a limitation of the present teachings.

In some embodiments of the present teachings, at least one SNP locus can be queried with at least one PCR encoding reaction followed by at least one PCR decoding reaction. It will be appreciated that a PCR encoding reaction can amplify a single SNP locus, as well as possibly amplify more than one SNP locus. In some embodiments, the more than one SNP locus amplified in the at least one encoding PCR can be subsequently queried in at least two decoding amplification reactions.

In some embodiments comprising an encoding PCR (in the case for SNP loci, as well as for the case of expressed genes, etc), the encoding PCR can comprise between 2-5 cycles. In some embodiments, the encoding PCR can comprise between 6-10 cycles. In some embodiments, the encoding PCR can comprise between 11-15 cycles. In some embodiments, the encoding PCR can comprise between 16-20 cycles. In some embodiments, the encoding PCR can comprise between 11-20 cycles. In some embodiments, the encoding PCR can comprise greater than 20 cycles.

Various teachings for performing encoding PCR amplification that are contemplated in the scope of the present teachings can be found for example in U.S. Pat. No. 6,605,451 to Xtrana, and U.S. patent application Ser. No. 10/723,520 to Andersen et al., For example, a multiplexed PCR encoding reaction can be performed (a "pre-amplification reaction") wherein the reaction can be ended before exhaustion of reaction components, and the plateau-effect occurs. In some embodiments, the primers present in such a pre-amplification reactions can comprise a target specific portion, an addressable primer portion, and an identifying portion, and subsequently, a plurality of downstream decoding reaction can be employed, wherein each decoding reaction comprises address primers and a labeling probe. In some embodiments, the primers present in such a pre-amplification reaction can comprise only a target specific portion and not comprise addressable primer portions or identifying portions. Subsequently, an encoding ligation reaction can be performed on the products of the pre-amplification reaction, thereby providing an encoding reaction wherein addressable primer portions and identifying portions can be introduced, as taught supra. Decoding reactions can then be performed according to the methods of the present teachings.

In some embodiments comprising an encoding PCR, various asynchronous and asymmetric strategies can be employed to produce the desired signal (see discussion for example in Pending P.C.T. Application US 03/29693.

In some embodiments comprising an encoding PCR (in the case for SNP loci, as well as for the case of expressed genes, etc), the addressable primer portions can result in the eventual use of two address primers in the at least one decoding reaction. In some embodiments comprising an encoding PCR, the addressable primer portions can result in the eventual use of a single address primer in the at least one decoding reaction. In some embodiments comprising an encoding ligation reaction (in the case for SNP loci, as well as for the case of expressed genes, etc), the addressable primer portions can result in the eventual use of two address primers in the at least one decoding reaction. In some embodiments comprising an encoding ligation reaction, the addressable primer portions can result in the eventual use of a single address primer in the at least one decoding reaction. For additional information on various primer configurations, see description under kits, as well as FIG. 17.

It will be appreciated that primer and probe design software programs are also commercially available, for example, Primer Express, Applied Biosystems, Foster City, Calif.; Primer Premier and Beacon Designer software, PREMIER Biosoft International, Palo Alto, Calif.; Primer Designer 4, Sci-Ed Software, Durham, N.C.; Primer Detective, ClonTech, Palo Alto, Calif.; Lasergene, DNASTAR, Inc., Madison, Wis.; Oligo software, National Biosciences, Inc., Plymouth, Minn.; iOligo, Caesar Software, Portsmouth, N.H.; and RTPrimerDB on the world wide web at realtimeprimerdatabase.ht.st or at medgen31.urgent.be/primerdatabase/index. See also, Pattyn et al., Nucl. Acid Res. 31:122-23 (2003).

The skilled artisan will appreciate that the complement of the disclosed probe, target, and primer sequences, or combinations thereof, may be employed in some embodiments of the present teachings. For example, without limitation, a genomic DNA sample may comprise both the target sequence and its complement. Thus, in some embodiments, when a genomic sample is denatured, both the target sequence and its complement are present in the sample as single-stranded sequences. In some embodiments, ligation probes may be designed to specifically hybridize to an appropriate sequence, either the target sequence or its complement.

In some embodiments, a minor groove binder may be attached to at least one labeling probe. Some exemplary minor groove binders and some exemplary methods of attaching minor groove binders to oligonucleotides are discussed, e.g., in U.S. Pat. Nos. 5,801,155 and 6,084,102. Some exemplary minor groove binders are those that are available from Epoch Biosciences, Bothell, Wash.

In some embodiments, the at least two identifying portions of the at least two encoding reactions differ by two nucleobases. In some embodiments, the at least two identifying portions of the at least two encoding reactions differ by 1 nucleobase. In some embodiments, the at least two identifying portions of the at least two encoding reactions differ by three nucleobases. In some embodiments, the at least two identifying portions of the at least two encoding reactions differ by more than 3 nucleobases.

In some embodiments, a FEN-LCR approach to ligation can be employed (see for example U.S. Pat. No. 6,511,810). In some embodiments, the identifying portion can be cleaved by a Flap endonuclease, or other agents comprising cleavage activity. Detection of the cleaved identifying portion can then identify the target polynucleotide. For example, addressable primer portions can be included in the identifying portion (for example in the 5' and 3' ends), and at least one decoding reaction performed comprising address primers corresponding to the incorporated addressable primer portions. In some embodiments, the cleaved identifying portion can comprise addressable primer portions in its ends, and an internal identifying portion located between the addressable primer portions. The decoding reaction can comprise a corresponding labeling probe complementary to the identifying portion, or complementary to the complement of the identifying portion, thereby allowing detection of the target polynucleotide sequence.

In some embodiments, the present teachings provide for pre-filled devices, wherein for example each well of the device can comprise a particular address primer or address primer set. For example, a pre-spotted 96 well dish could comprise 96 wells, wherein well 1 comprises address primer A and address primer B, well 2 comprises address primer C and address primer D, well 3 comprises address primer E and address primer F. Such devices include, but are not limited too, microtitre plates of various sizes and shapes, Applied Biosystems Low Density Expression Microarray (Microcard), and other devices and solid support generally recognized in the art. In some embodiments, the pre-filled devices can further comprise at least one labeling probe.

In some embodiments, libraries of probes can be employed in the encoding reaction, as described for example in pending P.C.T. Application US03/29867. In some embodiments, probes can be designed to query particular splice variants of an expressed gene, as described for example in pending P.C.T. Application US03/29867. In some embodiments, probes can comprise identifying portions on both the first probe and the second probe, as described for example in pending P.C.T. Application US03/29867.

In some embodiments, a given target polynucleotide X can be encoded with addressable primer portion A and addressable primer portion B, while a given target polynucleotide Y can be encoded with addressable primer portion C and addressable primer portion D. It will be appreciated that a target polynucleotide need not be encoded with a completely specific set of addressable primer portions. For example, a given target polynucleotide X can be encoded with addressable primer portion A and addressable primer portion B, while a given target polynucleotide Y can be encoded with addressable primer portion A and addressable primer portion C. Also see FIG. 17 for some additional teachings on various primer configurations contemplated by the present teachings.

In some embodiments of the present teachings, rare, minority target polynucleotides in a complex heterogenous reaction mixture can be detected with a ligation encoding reaction, as discussed for example in Published P.C.T. Application WO09803673A1.

While the present teachings have been described in terms of these exemplary embodiments, the skilled artisan will readily understand that numerous variations and modifications of these exemplary embodiments are possible without undue experimentation. All such variations and modifications are within the scope of the current teachings.

We claim:

1. A kit for comparing the amount of a target polynucleotide sequence between a first sample and a second sample comprising;

A) a first reaction vessel one comprising;

a forward primer, wherein the forward primer comprises a target specific portion and an addressable forward primer portion;

a reverse primer, wherein the reverse primer comprises a target specific portion and an addressable reverse primer portion, wherein the forward primer, the reverse primer, or both, comprise a first identifying portion;

B) a first reaction vessel two comprising;

a forward primer, wherein the forward primer comprises a target specific portion and an addressable forward primer portion;

a reverse primer, wherein the reverse primer comprises a target specific portion and an addressable reverse primer portion, wherein the forward primer, the reverse primer, or both, comprise a second identifying portion, wherein the identity of the target polynucleotide sequence is encoded with the forward addressable primer portion and the reverse addressable primer portion, and wherein the identity of the first sample is encoded by the first identifying portion and the identity of the second sample is encoded by the second identifying portion;

C) a second reaction vessel comprising;

a forward address primer and a reverse address primer;

wherein the forward addressable primer portion in vessel one is different from the forward addressable primer portion in vessel two; and, D) a PCR master mix comprising;

a polymerase, dNTPs, a buffer, a first labeling probe and a second labeling probe, wherein the first labeling probe is complementary to, or complementary to the complement of, the first identifying portion, and wherein the second labeling probe is complementary to, or complementary to the complement of, the second identifying portion.

2. The kit according to claim 1 wherein the first labeling probe, the second labeling probe, or both, comprise PNA.

3. The kit according to claim 1 wherein the first labeling probe, the second labeling probe, or both, are a 5'-nuclease cleavable probe.

4. A kit for comparing the amount of a target polynucleotide sequence between two samples comprising;
   A) a first reaction vessel one comprising;
   a first ligation probe, wherein the first ligation probe comprises a target specific portion and an addressable forward primer portion;
   a second ligation probe, wherein the second ligation probe comprises a target specific portion and an addressable reverse primer portion, wherein the first ligation probe, the second ligation probe, or both, comprise a first identifying portion;
   B) a first reaction vessel two comprising;
   a first ligation probe, wherein the first ligation probe comprises a target specific portion and an addressable forward primer portion;
   a second ligation probe, wherein the second ligation probe comprises a target specific portion and an addressable reverse primer portion, wherein the first ligation probe, the second ligation probe, or both, comprise a second identifying portion, wherein the identity of the target polynucleotide sequence is encoded with the forward addressable primer portion and the reverse addressable primer portion, and wherein the identity of the first sample is encoded by the first identifying portion and wherein the identity of the second sample is encoded by the second identifying portion;
   C) a second reaction vessel comprising;
   a forward address primer and a reverse address primer;
   wherein the forward addressable primer portion in vessel one is different from the forward addressable primer portion in vessel two;
   D) a PCR master mix, wherein the PCR master mix comprises; a polymerase, dNTPs, a buffer, a first labeling probe, and a second labeling probe, wherein the first labeling probe is complementary to, or complementary to the complement of, the first identifying portion, and wherein the second labeling probe is complementary to, or complementary to the complement of, the second identifying portion.

5. The kit according to claim 4 further comprising;
   E) a ligase master mix, wherein the ligase master mix comprises a ligase and a buffer.

6. The kit according to claim 4 wherein the first labeling probe, the second labeling probe, or both the first labeling probe and the second labeling probe comprise PNA.

7. The kit according to claim 4 wherein the first labeling probe, the second labeling probe, or both, are a 5'-nuclease cleavable probe.

* * * * *

SEQUENCE LISTING

```
<160> NUMBER OF SEQ ID NOS: 12

<210> SEQ ID NO 1
<211> LENGTH: 71
<212> TYPE: DNA
<213> ORGANISM: Artificial
<220> FEATURE:
<223> OTHER INFORMATION: Synthetic DNA

<400> SEQUENCE: 1
cagtccgtgg tagggcaggt tggggtgact agcacaaaaa cggttcgaca tagtagttct      60
agtatacgag t                                                          71

<210> SEQ ID NO 2
<211> LENGTH: 67
<212> TYPE: DNA
<213> ORGANISM: Artificial
<220> FEATURE:
<223> OTHER INFORMATION: Synthetic DNA
```

<400> SEQUENCE: 2
cacattgcac tctaaggaag ggtacttgtg ctgtgactac tggttggtga ggttgggtag    60
tcacaaa                                                              67

<210> SEQ ID NO 3
<211> LENGTH: 30
<212> TYPE: DNA
<213> ORGANISM: Artificial
<220> FEATURE:
<223> OTHER INFORMATION: Synthetic DNA

<400> SEQUENCE: 3
aaagagtgca atgtgactcg tatactattt                                     30

<210> SEQ ID NO 4
<211> LENGTH: 85
<212> TYPE: DNA
<213> ORGANISM: Artificial
<220> FEATURE:
<223> OTHER INFORMATION: Synthetic DNA

<400> SEQUENCE: 4
tactcagggc actgcaagca attgtggtcc caatgggctg agtaagcaca aacttccaac    60
cgttattgta cttgaatcaa gcact                                          85

<210> SEQ ID NO 5
<211> LENGTH: 77
<212> TYPE: DNA
<213> ORGANISM: Artificial
<220> FEATURE:
<223> OTHER INFORMATION: Synthetic DNA

<400> SEQUENCE: 5
cagattccag tcttaggttc ggagatggtg cttactcagg gcactgcaag caattgtggt    60
cccaatgggc tgagtat                                                   77

<210> SEQ ID NO 6
<211> LENGTH: 30
<212> TYPE: DNA
<213> ORGANISM: Artificial
<220> FEATURE:
<223> OTHER INFORMATION: Synthetic DNA

<400> SEQUENCE: 6
aaagactgga atctgagtgc ttgattcttt                                     30

<210> SEQ ID NO 7
<211> LENGTH: 21
<212> TYPE: DNA
<213> ORGANISM: Artificial
<220> FEATURE:
<223> OTHER INFORMATION: Synthetic DNA

<400> SEQUENCE: 7
ggagcacaaa aacggttcga c                                              21

<210> SEQ ID NO 8
<211> LENGTH: 21
<212> TYPE: DNA
<213> ORGANISM: Artificial
<220> FEATURE:
<223> OTHER INFORMATION: Synthethic DNA -continued

```
<400> SEQUENCE: 8
ggagcacaag taccttcct t                                               21

<210> SEQ ID NO 9
<211> LENGTH: 16
<212> TYPE: DNA
<213> ORGANISM: Artificial
<220> FEATURE:
<223> OTHER INFORMATION: Synthetic DNA

<400> SEQUENCE: 9
acgagtcaca ttgcac                                                    16

<210> SEQ ID NO 10
<211> LENGTH: 21
<212> TYPE: DNA
<213> ORGANISM: Artificial
<220> FEATURE:
<223> OTHER INFORMATION: Synthetic DNA

<400> SEQUENCE: 10
ggagcacaaa cttccaaccg t                                              21

<210> SEQ ID NO 11
<211> LENGTH: 21
<212> TYPE: DNA
<213> ORGANISM: Artificial
<220> FEATURE:
<223> OTHER INFORMATION: Synthetic DNA

<400> SEQUENCE: 11
ggagcaccat ctccgaacct a                                              21

<210> SEQ ID NO 12
<211> LENGTH: 16
<212> TYPE: DNA
<213> ORGANISM: Artificial
<220> FEATURE:
<223> OTHER INFORMATION: Synthetic DNA

<400> SEQUENCE: 12
agcactcaga ttccag                                                    16
```